(12) United States Patent
Bevilacqua et al.

(10) Patent No.: US 6,960,439 B2
(45) Date of Patent: Nov. 1, 2005

(54) IDENTIFICATION, MONITORING AND TREATMENT OF DISEASE AND CHARACTERIZATION OF BIOLOGICAL CONDITION USING GENE EXPRESSION PROFILES

(75) Inventors: Michael Bevilacqua, Boulder, CO (US); Danute M. Bankaitis-Davis, Longmont, CO (US); John C. Cheronis, Conifer, CO (US); Victor Tryon, Loveland, CO (US)

(73) Assignee: Source Precision Medicine, Inc., Boulder, CO (US)

( * ) Notice: Subject to any disclaimer, the term of this patent is extended or adjusted under 35 U.S.C. 154(b) by 297 days.

(21) Appl. No.: 10/291,225

(22) Filed: Nov. 8, 2002

(65) Prior Publication Data

US 2004/0133352 A1 Jul. 8, 2004

Related U.S. Application Data

(63) Continuation-in-part of application No. 09/821,850, filed on Mar. 29, 2001, now Pat. No. 6,692,916, which is a continuation-in-part of application No. 09/605,581, filed on Jun. 28, 2000, now abandoned.

(60) Provisional application No. 60/348,213, filed on Nov. 9, 2001, provisional application No. 60/340,881, filed on Dec. 7, 2001, provisional application No. 60/369,633, filed on Apr. 3, 2002, provisional application No. 60/376,997, filed on Apr. 30, 2002, provisional application No. 60/141,542, filed on Jun. 28, 1999, and provisional application No. 60/195,522, filed on Apr. 7, 2000.

(51) Int. Cl.[7] ............................ C12Q 1/68; G06F 19/00
(52) U.S. Cl. ................................ 435/6; 702/19; 702/20
(58) Field of Search ............................. 435/6; 702/19, 702/20

(56) References Cited

U.S. PATENT DOCUMENTS

| | | | |
|---|---|---|---|
| 5,643,765 A | 7/1997 | Willey ........................ | 435/91.2 |
| 5,696,130 A | 12/1997 | Jones et al. ................... | 514/291 |
| 5,811,231 A | 9/1998 | Farr et al. ...................... | 435/6 |
| 5,846,720 A | 12/1998 | Foulkes et al. ................ | 435/6 |
| 5,866,330 A | 2/1999 | Kinzier et al. ................. | 435/6 |
| 5,955,269 A | 9/1999 | Ghai et al. ..................... | 435/6 |
| 5,968,784 A | 10/1999 | Spinella et al. ............ | 435/91.1 |
| 5,994,076 A | 11/1999 | Chenchik et al. .............. | 435/6 |
| 6,132,969 A | 10/2000 | Stoughton et al. ............. | 435/6 |
| 6,146,828 A | 11/2000 | Lapidus et al. ................ | 435/6 |
| 6,150,169 A | 11/2000 | Smith et al. ................. | 435/455 |
| 6,165,709 A | 12/2000 | Friend et al. ................... | 435/6 |
| 6,185,561 B1 | 2/2001 | Balaban et al. ................ | 707/6 |
| 6,203,987 B1 | 3/2001 | Friend et al. ................... | 435/6 |
| 6,203,988 B1 | 3/2001 | Kambara et al. .............. | 435/6 |
| 6,218,122 B1 | 4/2001 | Friend et al. ................... | 435/6 |
| 6,222,093 B1 | 4/2001 | Marton et al. ................. | 800/3 |
| 6,232,065 B1 | 5/2001 | Robinson et al. .............. | 435/6 |
| 6,245,517 B1 | 6/2001 | Chen et al. ..................... | 435/6 |
| 2001/0018182 A1 | 8/2001 | Friend et al. ................... | 435/6 |
| 2001/0029018 A1 | 10/2001 | Danenberg et al. ............ | 435/6 |
| 2001/0051344 A1 | 12/2001 | Shalon et al. ................... | 435/6 |
| 2002/0012932 A1 | 1/2002 | Wang ............................. | 435/6 |
| 2002/0045197 A1 | 4/2002 | Friend et al. ............... | 435/7.21 |

FOREIGN PATENT DOCUMENTS

| | | | |
|---|---|---|---|
| JP | 10-261029 | 9/1998 | |
| WO | WO 94/23023 | 10/1994 | .......... C12N/15/00 |
| WO | WO 97/41261 | 6/1997 | ............ C12Q/1/68 |
| WO | WO 98/24935 | 6/1998 | ............ C12Q/1/68 |
| WO | WO 98/24935 | 11/1998 | ............ C12Q/1/68 |
| WO | WO 99/04251 | 1/1999 | .......... G01N/27/26 |
| WO | WO 99/44063 | 2/1999 | .......... G01N/33/50 |
| WO | WO 99/46403 | 9/1999 | ............ C12Q/1/68 |
| WO | WO 99/54510 A3 | 10/1999 | ............ C12Q/1/68 |
| WO | WO 99/54510 A2 | 10/1999 | ............ C12Q/1/68 |
| WO | WO 99/11822 | 11/1999 | ............ C12Q/1/68 |
| WO | WO 99/57130 | 11/1999 | .......... C07H/21/04 |
| WO | WO 99/58720 | 11/1999 | ............ C12Q/1/68 |
| WO | WO 00/11208 | 2/2000 | ............ C12Q/1/68 |
| WO | WO 00/22172 | 4/2000 | ............ C12Q/1/68 |
| WO | WO 00/28092 | 5/2000 | ............ C12Q/1/68 |
| WO | WO 00/71756 A2 | 11/2000 | ............ C12Q/1/68 |
| WO | WO 01/11082 A2 | 2/2001 | ............ C12Q/1/68 |
| WO | WO 01/12851 A2 | 2/2001 | ............ C12Q/1/68 |
| WO | WO 01/20998 A1 | 3/2001 | .......... A01N/63/00 |
| WO | WO 01/23614 A1 | 4/2001 | ............ C12Q/1/68 |
| WO | WO 01/25473 A1 | 4/2001 | ............ C12Q/1/00 |
| WO | WO 01/27321 A2 | 4/2001 | ............ C12Q/1/68 |
| WO | WO 01/29261 A2 | 4/2001 | ............ C12Q/1/68 |
| WO | WO 01/29269 A2 | 4/2001 | ............ C12Q/1/68 |
| WO | WO 01/30972 A2 | 5/2001 | |
| WO | WO 01/32928 | 5/2001 | |
| WO | WO 03/040404 A1 | 5/2003 | ............ C12Q/1/00 |

OTHER PUBLICATIONS

Imai, S., et al., High Levels of Expression of Collagenase–3 (MMP–13) in Pathological Conditions Associated with a Foreign–Body Reaction; *J Bone Joint Surg*, vol. 80–B, pp. 701–710, Jul. 1998.

Humbert, M., et al., Relationship Between IL–4 and IL–5 mRNA Expression and Disease Severity in Atopic Asthma; *Am J Respir Crit Care Med*, vol. 156, pp. 704–708, 1997.

Ono, K., et al., Cytokine Gene Expression After Myocardial Infarction in Rat Hearts (Possible Implication in Left Ventricular Remodeling); *Circulation* vol. 98, pp. 149–156, Jul. 14, 1998.

(Continued)

Primary Examiner—Marianne P. Allen
(74) Attorney, Agent, or Firm—Bromberg & Sunstein LLP

(57) ABSTRACT

Gene expression data, in particular gene expression profiles, are created and used in the identification, monitoring and treatment of disease and characterization of biological conditions. Profile data sets are derived from subject samples and include quantitative substantially repeatable measures of a distinct amount of RNA or protein constituent in a panel selected to enable evaluation of a biological condition. Such profile data sets may be used to provide an index indicative of the biological state of a subject, which may be compared to a normative value of the index determined with respect to a relevant population of subjects.

27 Claims, 44 Drawing Sheets

OTHER PUBLICATIONS

Skedinger, M., et al., Eosinophil Activity Reflects Clinical Status in Patients with Asthma Before and During a Prednisolone Course; *Ann Allergy Asthma Immunol*, vol. 75, pp. 250–255, Sep. 1995.

Buchwald, D., et al., Markers of Inflammation and Immune Activation in Chronic Fatigue and Chronic Fatigue Syndrome; *J Rheumatol*, vol. 24, pp. 372–376; 1997.

Asthana, D., et al., Differential Effects of IFN-γ on Kidney Cell Expression of MHC Class II Molecules, Kidney Cell Associated Molecules and Their Stimulatory Capacity in Mixed Lymphocyte Kidney Cell Culture; *Transpl Immunol*, vol. 1, pp. 282–293; 1993.

PE Applied Biosystems Manual, "The TaqMan™ PCR Reagent Kit Protocol", May 1996.

Beasley, Ellen M., et al., "Statistical Refinement of Primer Design Parameters," Academic Press, PCR Applications, 1999, pp., 59–71.

Beer, David G., et al., "Gene–Expression Profiles Predict Survival of Patients With Lung Adenocarcinoma," *Nature Medicine*, Aug. 2002, vol. 8, No. 8, pp. 816–824.

Cheronis, J.C., et al., "Utility of High Precision QPCR in the Assessment of Anti–Inflammatory Drug Action," *Clinical Chemistry*, vol. 48, No. 6, Supplement, Jun. 2002, p. A172.

Coenen, et al, "A quantitative PCR measurement of messenger RNA expression of IGF–I, IGF–II and IGFBP–5 in human skeletal muscle", *Growth Hormone & IGF Research* 1999,9, 179–186 Article No.ghir.1999.0104.

Cole, et al., "The genetics of cancer–a 3D model", Nature Genetics Supplement, vol. 21, Jan. 1999.

Eisenberg, et al., "Protein Function in the Post–Genomic Era," *Nature*, vol. 405:823–826, Jun. 15, 2000.

Guan–Chiun Lee, et al, Analysis of the Gene Family Encoding Lipases in *candid rugisa* by Competitive Reverse Transcription–PCR, *Applied and Environmental Microbiology*, Sep. 1999, pp. 3888–3895.

Jensen, et al, "Competitive reverse transcription polymerase chain reaction for quantifying pre–MRNA and mRNA of major acute phase proteins", *Journal of Immunological Methods*, 215 (1998), pp. 45–58.

Kim, et al., "Strong Feature Sets from Small Samples", Journal of Computational Biology, vol. 9, No. 1, 2002, Mary Ann Liebert, Inc. pp. 1127–1146.

Korenberg, "Prediction of Treatment Response Using Gene Expression Profiles", Journal of Proteome Research 2002, 1, 55–61.

Lockhart, et al., "Genomics, Gene expression and DNA Arrays," *Nature*, vol. 405:827–836, Jun. 15, 2000.

Loitsch, et al, "Reverse Transcription–Competitive Multiplex PCR Improves Quantification of mRNA in Clinical Samples–Application to the Low Abundance CFTR mRNA", *Clinical Chemistry* 45:5, (1999), pp. 619–624.

Mangalam, et al., "GeneX: An open source gene expression database and integrated tool set", IBM Systems Journal, (2001), 40 (2), 552–569, 79 refs. ISSN: 0018–8670.

Meijers–Heijboer, M.D., et al., "Breast Cancer after Prophylactic Bilateral Mastectomy in Women with a BRCA1 or BRCA2 Mutation", The New England Journal of Medicine, vol. 345:159–164, Jul. 19, 2001, No. 3.

Pandey, et al., "Proteomics to Study Genes and Genomes," *Nature*, vol. 405:837–846, Jun. 15, 2000.

Paradis, Valerie, et al., "Expression Profiling of Hepatocellular Carcinomas (HCC) Using a Large Scale Real–Time RT–PCR Approach: Determination of a Molecular Diagnostic Index," *Hepatology*, vol. 36, No. 4, Part 2, Oct. 2002, p. 302A.

PCT/US 00/17846, International Search Report, Jun. 28, 1999, PCT/ISA/210.

Pfeffer, U., "One–Tube RT–PCR With Sequence–Specific Primers," *Methods of Molecular Biology*, vol. 86, pp. 149–151.

Rafalski, et al., "New experimental and computational approaches to the analysis of gene expression", Acta Biochimica Polonica, vol. 45, No. 4/1998, 929–934.

Reinke, P., et al., "Immune Monitoring of Glucocorticoid Therapy," *Ernst Schering Research Foundation Workshop*. Germany 2002, No. 40, pp. 25–37.

Risch, "Searching for Genetic Determinants in the New Millennium," *Nature*, vol. 405:847–856, Jun. 15, 2000.

Rosenwald, M.D., et al, "The Use of Molecular Profiling to Predict Survival after Chemotherapy for Diffuse Large–B–Cell Lymphoma", The New England Journal of Medicine, vol. 346:1937–1947, Jun. 20, 2002, No. 25.

Roses, Pharmacogenetics and the Pratice of Medicine, *Nature*, vol. 405:857–865, Jun. 15, 2000.

Staunton, et al., "Chemosensitivity predication by transcriptional profiling", Proc. Natl. Acad. Sci. USA, vol. 98, Issue 19, 10787–10792, Sep. 11, 2001.

Takahashi, et al., "Gene expression profiling of clear cell renal cell carcinoma: Gene identification and prognostic classification", Proc. Natl. Acad. Sci. USA, vol. 98, Issue 17, 9754–9759, Aug. 14, 2001.

Teague, et al, "Activation changes the spectrum but not the diversity of genes expressed by T cells", Proc. Natl. Acad. Sci. USA, vol. 96, Issue 22, 12691–12696, Oct. 26, 1999.

Van 't Veer, et al., "Gene expression profiling predicts clinical outcome of breast cancer", Nature, vol. 415, Jan. 31, 2002.

Vukmirovic, et al., "Exploring Genome Space," *Nature*, vol. 405:820–822, Jun. 15, 2000.

Wiedbrauk, Danny L, et al., "Nucleic Acid Detection Methods," *Molecular Methods for Virus Detection*, Academic Press, 1995, pp. 1–26.

Wittwer, Carl T., et al., "Rapid Thermal Cycling and PCR Kinetics," Academic Press, PCR Applications, 1999, pp. 211–231.

Zajchowski, et al., "Identification of Gene Expression Profiles That Predict the Aggressive Behavior of Breast Cancer Cells", Cancer Research 6, 5168–5178, Jul. 1, 2001.

Zhan, et al., "Gloral Gene Expression Profiles Can be Used to Accurately Predict Chromosome 13 Deletion in Multiple Myeloma", Abstract #1553, Poster Board #–Session: 658–II.

Zhang, et al, "A Novel Highly Reproducible Quantitative Competitive RT PCR System",*J. Mol. Biol* (1997) 274, pp. 338–352.

Zhang, et al., "Recursive partitioning for tumor classification with gene expression microarray data", Proc. Natl. Acad. Sci, USA, vol. 98, Issue 12, 6730–6735, Jun. 5, 2001.

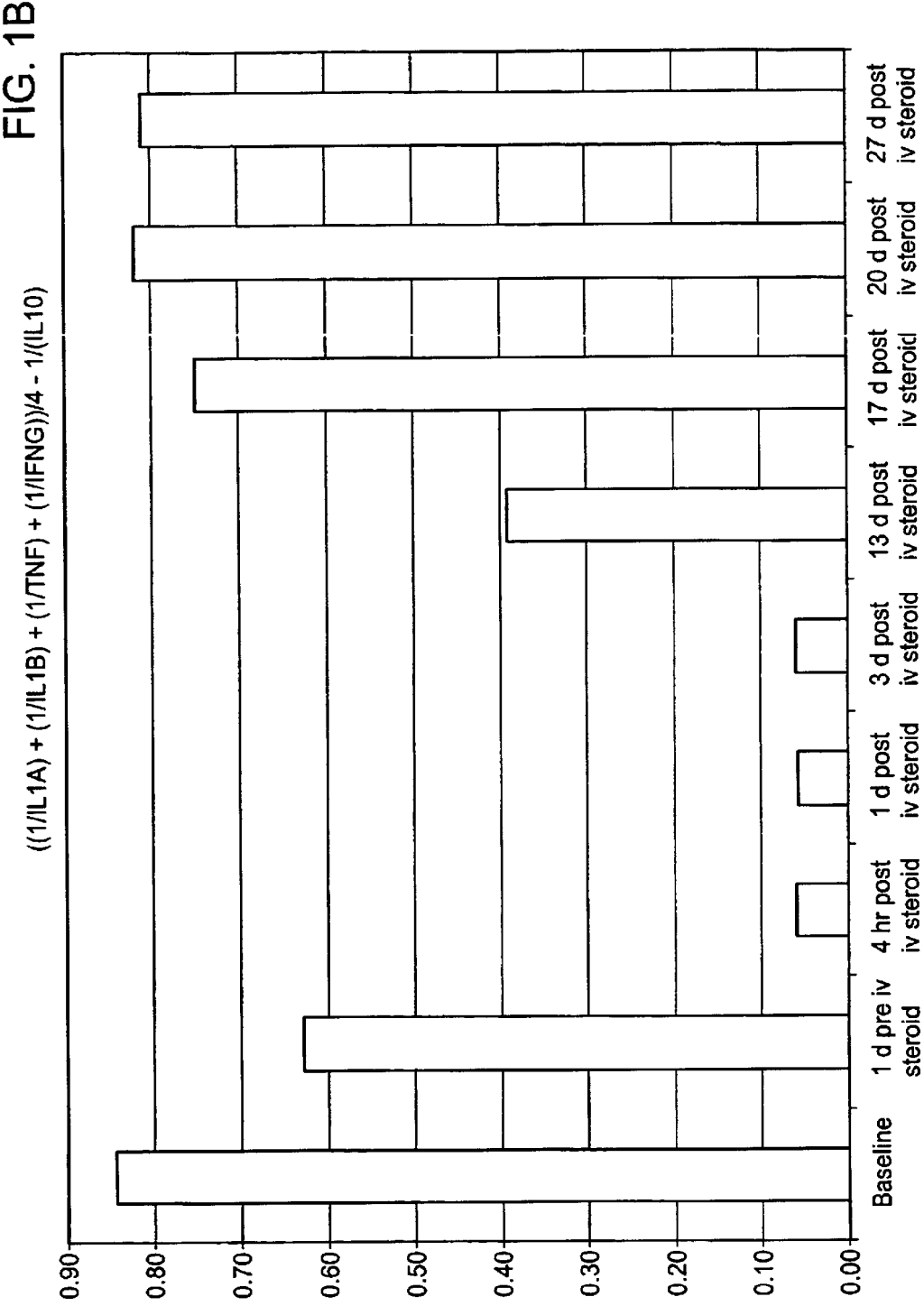

IDENTIFICATION, MONITORING AND TREATMENT OF DISEASE AND CHARACTERIZATION OF BIOLOGICAL CONDITION USING GENE EXPRESSION PROFILES

RELATED APPLICATIONS

The present application claims priority from a series of provisional patent applications, by inventors herein, as follows: Ser. No. 60/348,213, filed Nov. 9, 2001; Ser. No. 60/340,881, filed Dec. 7, 2001; Ser. No. 60/369,633, filed Apr. 3, 2002; and Ser. No. 60/376,997, filed Apr. 30, 2002. The present application is also a continuation in part of application Ser. No. 09/821,850, filed Mar. 29, 2001 now U.S. Pat. No. 6,692,916, which in turn is a continuation in part of application Ser. No. 09/605,581, filed Jun. 28, 2000 now abandoned, by the same inventors herein, which application claims priority from provisional application Ser. No. 60/141,542, filed Jun. 28, 1999 and provisional application Ser. No. 60/195,522 filed Apr. 7, 2000.

TECHNICAL FIELD AND BACKGROUND ART

The present invention relates to use of gene expression data, and in particular to use of gene expression data in identification, monitoring and treatment of disease and in characterization of biological condition of a subject.

The prior art has utilized gene expression data to determine the presence or absence of particular markers as diagnostic of a particular condition, and in some circumstances have described the cumulative addition of scores for over expression of particular disease markers to achieve increased accuracy or sensitivity of diagnosis. Information on any condition of a particular patient and a patient's response to types and dosages of therapeutic or nutritional agents has become an important issue in clinical medicine today not only from the aspect of efficiency of medical practice for the health care industry but for improved outcomes and benefits for the patients.

SUMMARY OF THE INVENTION

In a first embodiment, there is provided a method, for evaluating a biological condition of a subject, based on a sample from the subject. The method includes:

deriving from the sample a profile data set, the profile data set including a plurality of members, each member being a quantitative measure of the amount of a distinct RNA or protein constituent in a panel of constituents selected so that measurement of the constituents enables evaluation of the biological condition; and in deriving the profile data set, achieving such measure for each constituent under measurement conditions that are substantially repeatable.

There is a related embodiment for providing an index that is indicative of the state of a subject, as to a biological condition, based on a sample from the subject. This embodiment includes:

deriving from the sample a profile data set, the profile data set including a plurality of members, each member being a quantitative measure of the amount of a distinct RNA or protein constituent in a panel of constituents selected so that measurement of the constituents enables evaluation of the biological condition; and in deriving the profile data set, achieving such measure for each constituent under measurement conditions that are substantially repeatable; and applying values from the profile data set to an index function that provides a mapping from an instance of a profile data set into a single-valued measure of biological condition, so as to produce an index pertinent to the biological condition of the subject. In further embodiments related to the foregoing, there is also included, in deriving the profile data set, achieving such measure for each constituent under measurement conditions wherein specificity and efficiencies of amplification for all constituents are substantially similar. Similarly further embodiments include alternatively or in addition, in deriving the profile data set, achieving such measure for each constituent under measurement conditions wherein specificity and efficiencies of amplification for all constituents are substantially similar.

In embodiments relating to providing the index a further embodiment also includes providing with the index a normative value of the index function, determined with respect to a relevant population, so that the index may be interpreted in relation to the normative value. Optionally providing the normative value includes constructing the index function so that the normative value is approximately 1. Also optionally, the relevant population has in common a property that is at least one of age group, gender, ethnicity, geographic location, diet, medical disorder, clinical indicator, medication, physical activity, body mass, and environmental exposure.

In another related embodiment, efficiencies of amplification, expressed as a percent, for all constituents lie within a range of approximately 2 percent, and optionally, approximately 1 percent.

In another related embodiment, measurement conditions are repeatable so that such measure for each constituent has a coefficient of variation, on repeated derivation of such measure from the sample, that is less than approximately 3 percent. In further embodiments, the panel includes at least three constituents and optionally fewer than approximately 500 constituents.

In another embodiment, the biological condition being evaluated is with respect to a localized tissue of the subject and the sample is derived from tissue or fluid of a type distinct from that of the localized tissue. In related embodiments, the biological condition may be any of the conditions identified in Tables 1 through 12 herein, in which case there are measurements conducted corresponding to constituents of the corresponding Gene Expression Panel. The panel in each case includes at least two, and optionally at least three, four, five, six, seven, eight, nine or ten, of the constituents of the corresponding Gene Expression Panel.

In another embodiment, there is provided a method of providing an index that is indicative of the inflammatory state of a subject based on a sample from the subject that includes: deriving from the sample a first profile data set, the first profile data set including a plurality of members, each member being a quantitative measure of the amount of a distinct RNA or protein constituent in a panel of constituents, the panel including at least two of the constituents of the Inflammation Gene Expression Panel of Table 1; (although in other embodiments, at least three, four, five, six or ten constituents of the panel of Table 1 may be used in a panel) wherein, in deriving the first profile data set, such measure is performed for each constituent both under conditions wherein specificity and efficiencies of amplification for all constituents are substantially similar and under substantially repeatable conditions; and applying values from the first profile data set to an index function that provides a mapping from an instance of a profile data set into a single-valued measure of biological condition (in an embodiment, this may be an inflammatory condition), so as to produce an index pertinent to the biological condition of the sample or the subject. The biological condition may be any condition that is assessable using an appropriate Gene Expression Panel; the measurement of the extent of inflammation using the Inflammation Gene Expression Panel is merely an example.

In additional embodiments, the mapping by the index function may be further based on an instance of a relevant baseline profile data set and values may be applied from a corresponding baseline profile data set from the same subject or from a population of subjects or samples with a similar or different biological condition. Additionally, the index function may be constructed to deviate from a normative value generally upwardly in an instance of an increase in expression of a constituent whose increase is associated with an increase of inflammation and also in an instance of a decrease in expression of a constituent whose decrease is associated with an increase of inflammation. The index function alternatively be constructed to weigh the expression value of a constituent in the panel generally in accordance with the extent to which its expression level is determined to be correlated with extent of inflammation. The index function may be alternatively constructed to take into account clinical insight into inflammation biology or to take into account experimentally derived data or to take into account relationships derived from computer analysis of profile data sets in a data base associating profile data sets with clinical and demographic data. In this connection, the construction of the index function may be achieved using statistical methods, which evaluate such data, to establish a model of constituent expression values that is an optimized predictor of extent of inflammation.

In another embodiment, the panel includes at least one constituent that is associated with a specific inflammatory disease.

The methods described above may further utilize the step wherein (i) the mapping by the index function is also based on an instance of at least one of demographic data and clinical data and (ii) values are applied from the first profile data set including applying a set of values associated with at least one of demographic data and clinical data.

In another embodiment of the above methods, a portion of deriving the first profile data set is performed at a first location and applying the values from the first profile data set is performed at a second location, and data associated with performing the portion of deriving the first profile data set are communicated to the second location over a network to enable, at the second location, applying the values from the first profile data set.

In an embodiment of the methods, the index function is a linear sum of terms, each term being a contribution function of a member of the profile data set. Moreover, the contribution function may be a weighted sum of powers of one of the member or its reciprocal, and the powers may be integral, so that the contribution function is a polynomial of one of the member or its reciprocal. Optionally, the polynomial is a linear polynomial. The profile data set may include at least three, four or all members corresponding to constituents selected from the group consisting of IL1A, IL1B, TNF, IFNG and IL10. The index function may be proportional to $\frac{1}{4}\{IL1A\}+\frac{1}{4}\{IL1B\}+\frac{1}{4}\{TNF\}+\frac{1}{4}\{INFG\}-1/\{IL10\}$ and braces around a constituent designate measurement of such constituent.

In an additional embodiment, a method is provided of analyzing complex data associated with a sample from a subject for information pertinent to inflammation, the method that includes: deriving a Gene Expression Profile for the sample, the Gene Expression Profile being based on a Signature Panel for Inflammation; and using the Gene Expression Profile to determine a Gene Expression Profile Inflammatory Index for the sample.

In an additional embodiment, a method is provided of monitoring the biological condition of a subject, that includes deriving a Gene Expression Profile for each of a series of samples over time from the subject, the Gene Expression Profile being based on a Signature Panel for Inflammation; and for each of the series of samples, using the corresponding Gene Expression Profile to determine a Gene Expression Profile Inflammatory Index.

In an additional embodiment, there is provided a method of determining at least one of (i) an effective dose of an agent to be administered to a subject and (ii) a schedule for administration of an agent to a subject, the method including: deriving a Gene Expression Profile for a sample from the subject, the Gene Expression Profile being based on a Signature Panel for Inflammation; using the Gene Expression Profile to determine a Gene Expression Profile Inflammatory Index for the sample; and using the Gene Expression Profile Inflammatory Index as an indicator in establishing at least one of the effective dose and the schedule.

In an additional embodiment, a method of guiding a decision to continue or modify therapy for a biological condition of a subject, is provided that includes: deriving a Gene Expression Profile for a sample from the subject, the Gene Expression Profile being based on a Signature Panel for Inflammation; and using the Gene Expression Profile to determine a Gene Expression Profile Inflammatory Index for the sample.

A method of predicting change in biological condition of a subject as a result of exposure to an agent, is provided that includes: deriving a first Gene Expression Profile for a first sample from the subject in the absence of the agent, the first Gene Expression Profile being based on a Signature Panel for Inflammation; deriving a second Gene Expression Profile for a second sample from the subject in the presence of the agent, the second Gene Expression Profile being based on the same Signature Panel; and using the first and second Gene Expression Profiles to determine correspondingly a first Gene Expression Profile Inflammatory Index and a second Gene Expression Profile Inflammatory Index. Accordingly, the agent may be a compound and the compound may be therapeutic.

In an additional embodiment, a method of evaluating a property of an agent is provided where the property is at least one of purity, potency, quality, efficacy or safety, the method including: deriving a first Gene Expression Profile from a sample reflecting exposure to the agent of (i) the sample, or (ii) a population of cells from which the sample is derived, or (iii) a subject from which the sample is derived; using the Gene Expression Profile to determine a Gene Expression Profile Inflammatory Index; and using the Gene Expression Profile Inflammatory Index in determining the property.

In accordance with another embodiment there is provided a method of providing an index that is indicative of the biological state of a subject based on a sample from the subject. The method of this embodiment includes:

deriving from the sample a first profile data set, the first profile data set including a plurality of members, each member being a quantitative measure of the amount of a distinct RNA or protein constituent in a panel of constituents, the panel including at least two of the constituents of the Inflammation Gene Expression Panel of Table 1; and applying values from the first profile data set to an index function that provides a mapping from an instance of a profile data set into a single-valued measure of biological condition, so as to produce an index pertinent to the biological condition of the sample or the subject.

In carrying out this method the index function also uses data from a baseline profile data set for the panel. Each member of the baseline data set is a normative measure, determined with respect to a relevant population of subjects, of the amount of one of the constituents in the panel. In addition, in deriving the first profile data set and the baseline data set, such measure is performed for each constituent both under conditions wherein specificity and efficiencies of amplification for all constituents are substantially similar and under substantially repeatable conditions.

In another type of embodiment, there is provided a method, for evaluating a biological condition of a subject, based on a sample from the subject. In this embodiment, the method includes:

deriving from the sample a first profile data set, the first profile dataset including a plurality of members, each member being a quantitative measure of the amount of a distinct RNA or protein constituent in a panel of constituents selected so that measurement of the constituents enables measurement of the biological condition; and producing a calibrated profile data set for the panel, wherein each member of the calibrated profile data set is a function of a corresponding member of the first profile data set and a corresponding member of a baseline profile data set for the panel.

In this embodiment, each member of the baseline data set is a normative measure, determined with respect to a relevant population of subjects, of the amount of one of the constituents in the panel, and the calibrated profile data set provides a measure of the biological condition of the subject.

In a similar type of embodiment, there is provided a method, for evaluating a biological condition of a subject, based on a sample from the subject, and the method of this embodiment includes:

applying the first sample or a portion thereof to a defined population of indicator cells;

obtaining from the indicator cells a second sample containing at least one of RNAs or proteins;

deriving from the second sample a first profile data set, the first profile data set including a plurality of members, each member being a quantitative measure of the amount of a distinct RNA or protein constituent in a panel of constituents selected so that measurement of the constituents enables measurement of the biological condition; and producing a calibrated profile data set for the panel, wherein each member of the calibrated profile data set is a function of a corresponding member of the first profile data set and a corresponding member of a baseline profile data set for the panel, wherein each member of the baseline data set is a normative measure, determined with respect to a relevant population of subjects, of the amount of one of the constituents in the panel, the calibrated profile data set providing a measure of the biological condition of the subject.

Furthermore, another and similar, type of embodiment provides a method, for evaluating a biological condition affected by an agent. The method of this embodiment includes:

obtaining, from a target population of cells to which the agent has been administered, a sample having at least one of RNAs and proteins;

deriving from the sample a first profile data set, the first profile data set including a plurality of members, each member being a quantitative measure of the amount of a distinct RNA or protein constituent in a panel of constituents selected so that measurement of the constituents enables measurement of the biological condition; and producing a calibrated profile data set for the panel, wherein each member of the calibrated profile data set is a function of a corresponding member of the first profile data set and a corresponding member of a baseline profile data set for the panel, wherein each member of the baseline data set is a normative measure, determined with respect to a relevant population of subjects, of the amount of one of the constituents in the panel, the calibrated profile data set providing a measure of the biological condition as affected by the agent.

In further embodiments based on these last three embodiments, the relevant population may be a population of healthy subjects. Alternatively, or in addition, the relevant population is has in common a property that is at least one of age group, gender, ethnicity, geographic location, diet, medical disorder, clinical indicator, medication, physical activity, body mass, and environmental exposure.

Alternatively or in addition, the panel includes at least two of the constituents of the Inflammation Gene Expression Panel of Table 1. (Other embodiments employ at least three, four, five, six, or ten of such constituents.) Also alternatively or in addition, in deriving the first profile data set, such measure is performed for each constituent both under conditions wherein specificity and efficiencies of amplification for all constituents are substantially similar and under substantially repeatable conditions. Also alternatively, when such measure is performed for each constituent both under conditions wherein specificity and efficiencies of amplification for all constituents are substantially similar and under substantially repeatable conditions, optionally one need not produce a calibrated profile data set, but may instead work directly with the first data set.

In another embodiment, there is provided a method, for evaluating the effect on a biological condition by a first agent in relation to the effect by a second agent. The method of this embodiment includes:

obtaining, from first and second target populations of cells to which the first and second agents have been respectively administered, first and second samples respectively, each sample having at least one of RNAs and proteins;

deriving from the first sample a first profile data set and from the second sample a second profile data set, the profile data sets each including a plurality of members, each member being a quantitative measure of the amount of a distinct RNA or protein constituent in a panel of constituents selected so that measurement of the constituents enables measurement of the biological condition; and producing for the panel a first calibrated profile data set and a second profile data set, wherein (i) each member of the first calibrated profile data set is a function of a corresponding member of the first profile data set and a corresponding member of a baseline profile data set for the panel, wherein each member of the baseline data set is a normative measure, determined with respect to a relevant population of subjects, of the amount of one of the constituents in the panel, and (ii) each member of the second calibrated profile data set is a function of a corresponding member of the second profile data set and a corresponding member of the baseline profile data set, the calibrated profile data sets providing a measure of the effect by the first agent on the biological condition in relation to the effect by the second agent.

In this embodiment, in deriving the first and second profile data sets, such measure is performed for each constituent both under conditions wherein specificity and efficiencies of amplification for all constituents are substantially similar and under substantially repeatable conditions. In a further related embodiment, the first agent is a first drug and the second agent is a second drug. In another related embodiment, the first agent is a drug and the second agent is a complex mixture. In yet another related embodiment, the first agent is a drug and the second agent is a nutriceutical.

BRIEF DESCRIPTION OF THE DRAWINGS

The foregoing features of the invention will be more readily understood by reference to the following detailed description, taken with reference to the accompanying drawings, in which:

FIG. 1B illustrates use of an inflammation index in relation to the data of FIG. 1A, in accordance with an embodiment of the present invention.

Figure 21:
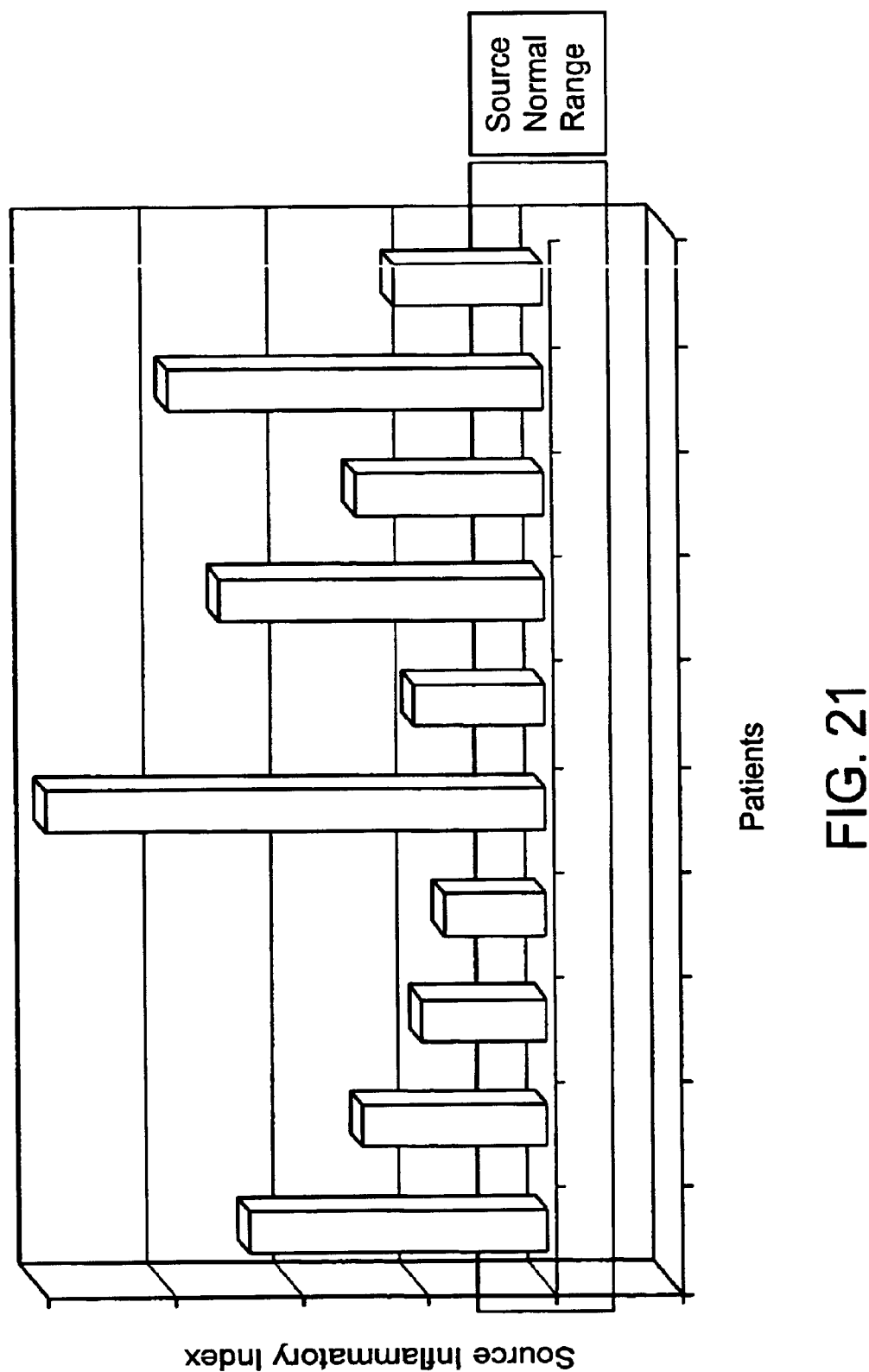
Figure 22:
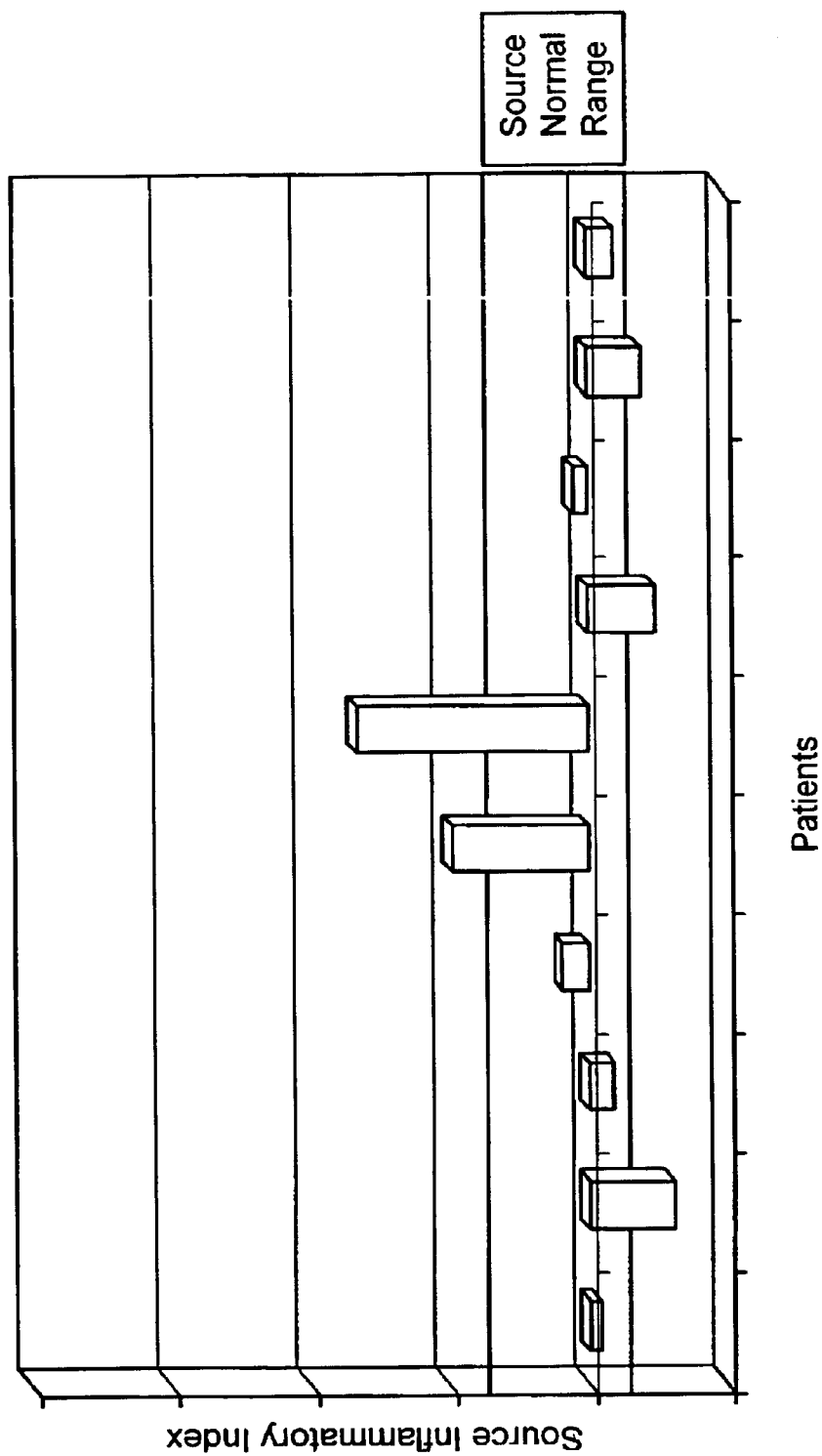
Figure 23:
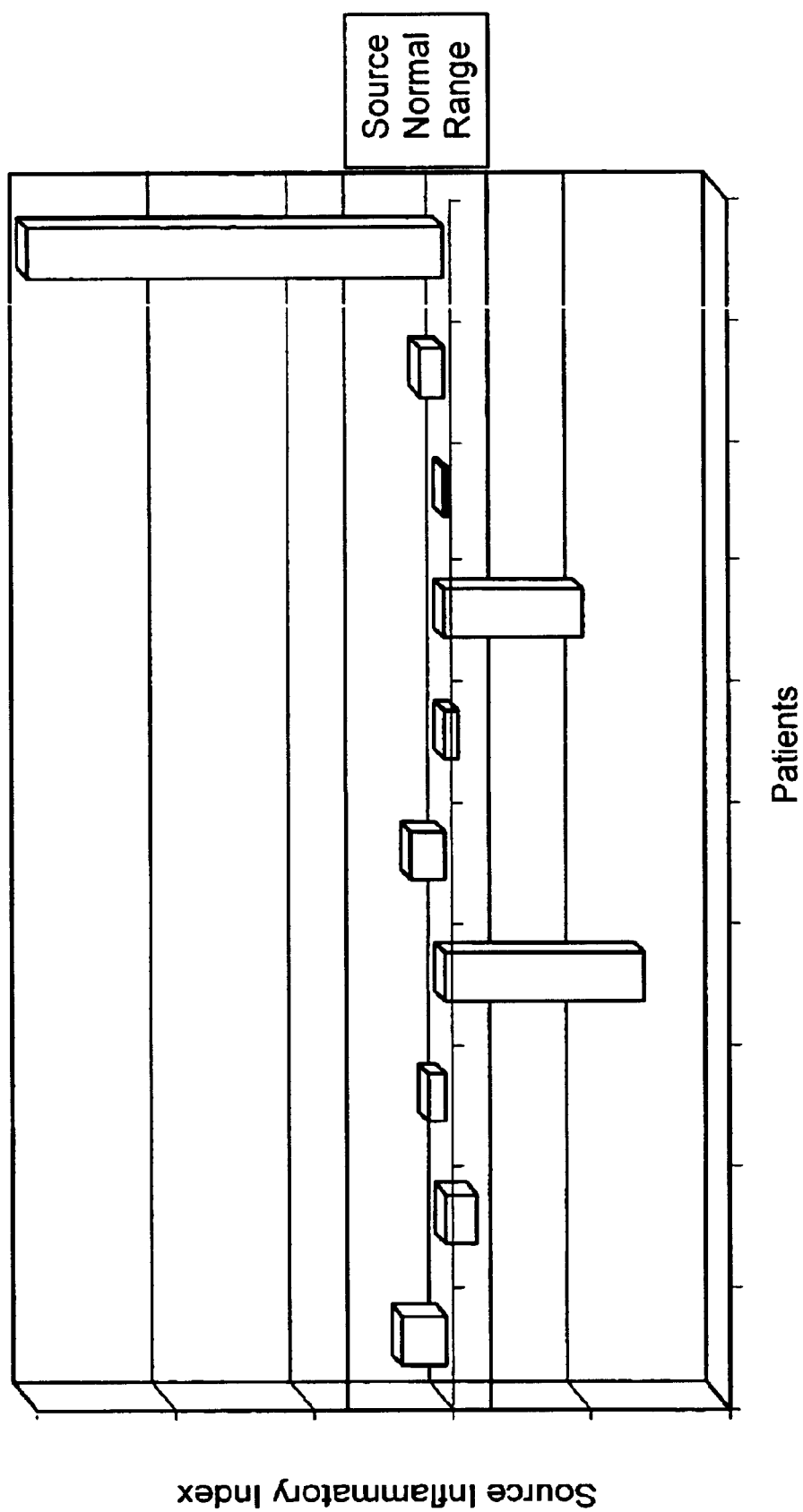

Each of FIGS. 21–23 shows the inflammation index for an international group of subjects, suffering from rheumatoid arthritis, undergoing three separate treatment regimens.

Figure 24:
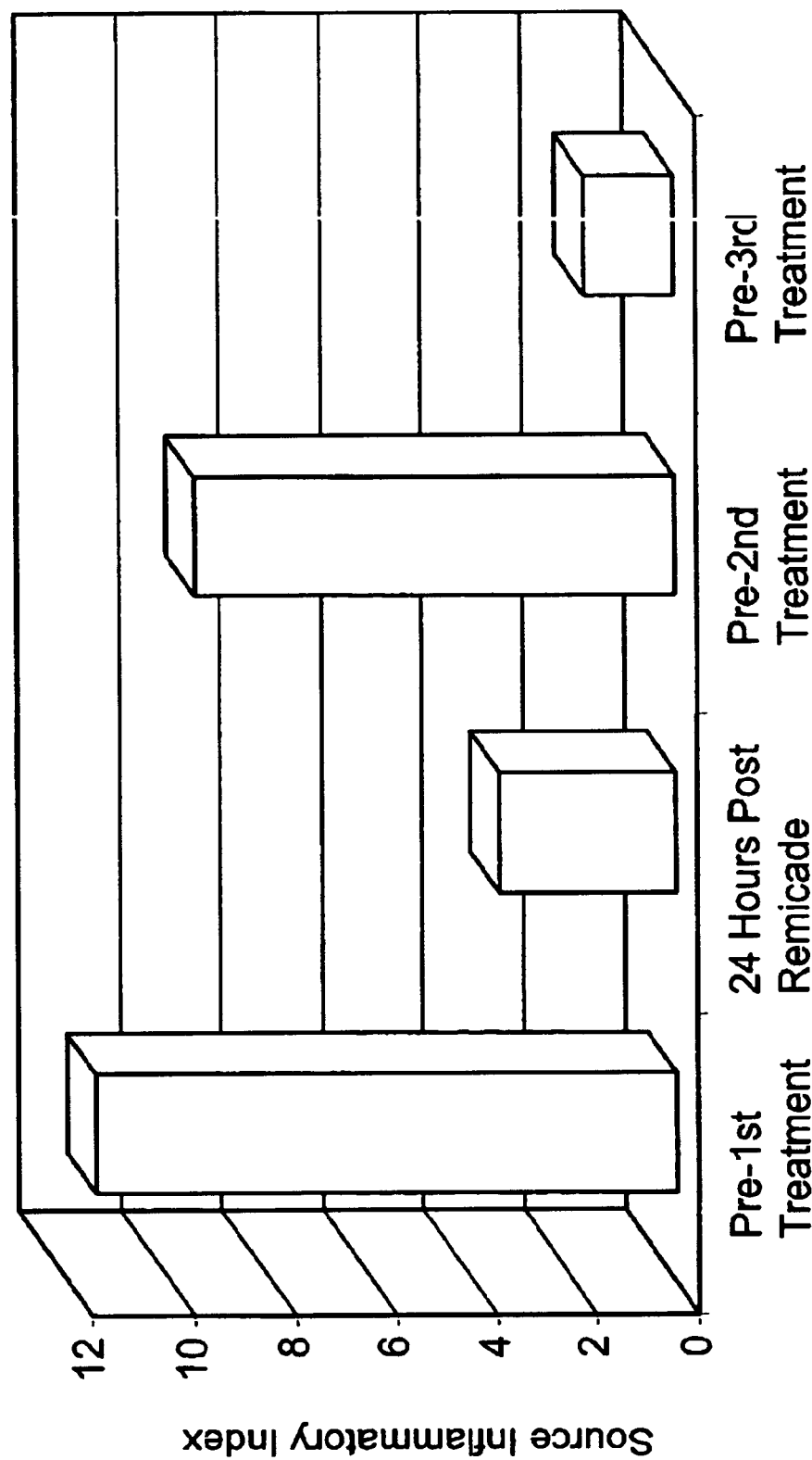

FIG. 24 illustrates use of the inflammation index for assessment of a single subject suffering from inflammatory bowel disease.

Figure 25:
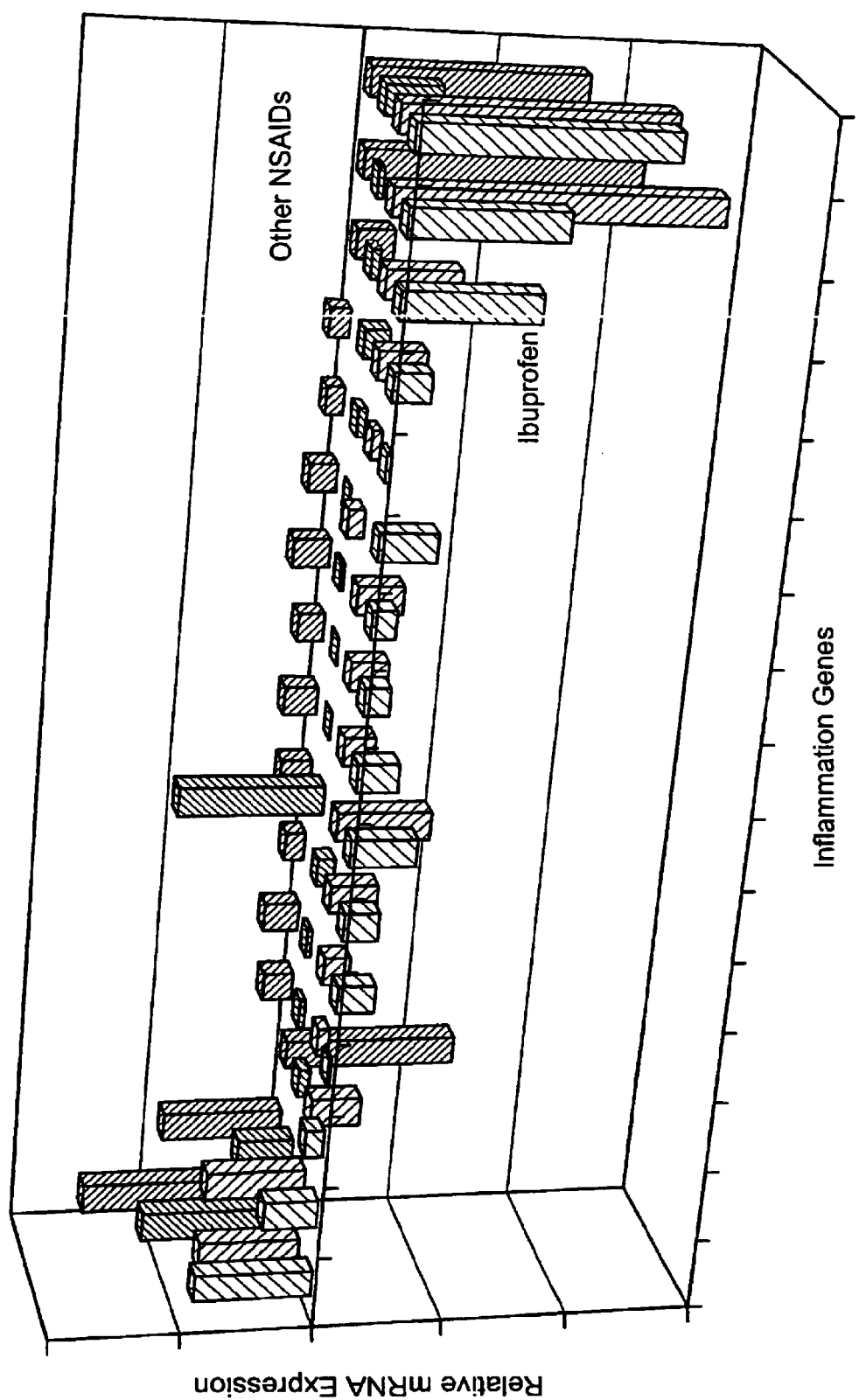
Figure 26A:
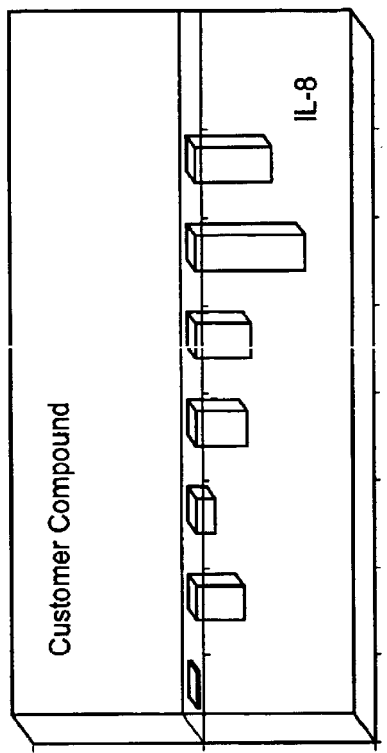
Figure 26C:
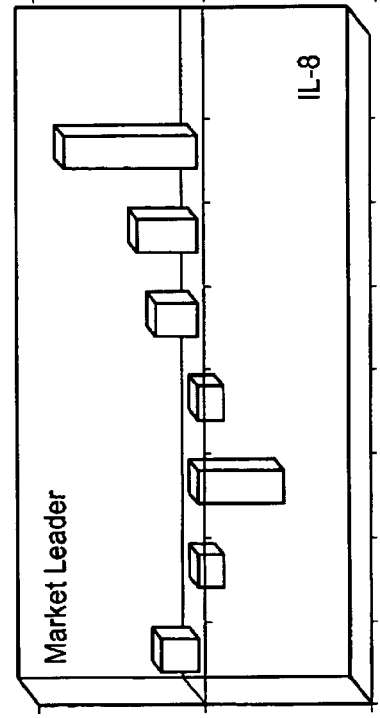
Figure 26B:
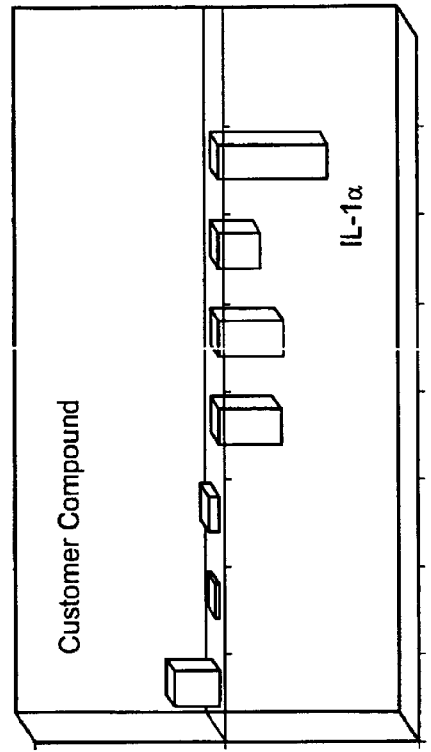
Figure 26D:
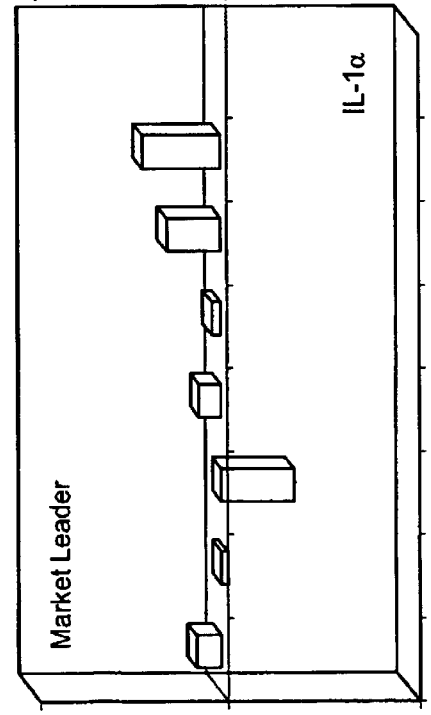

FIG. 25 shows Gene Expression Profiles with respect to 24 loci (of the Inflammation Gene Expression Panel of Table 1) for whole blood treated with Ibuprofen in vitro in relation to other non-steroidal anti-inflammatory drugs (NSAIDs).

FIG. 26 illustrates how the effects of two competing anti-inflammatory compounds can be compared objectively, quantitatively, precisely, and reproducibly.

FIGS. 27 through 41 illustrate the use of gene expression panels in early identification and monitoring of infectious disease.

Figure 27:
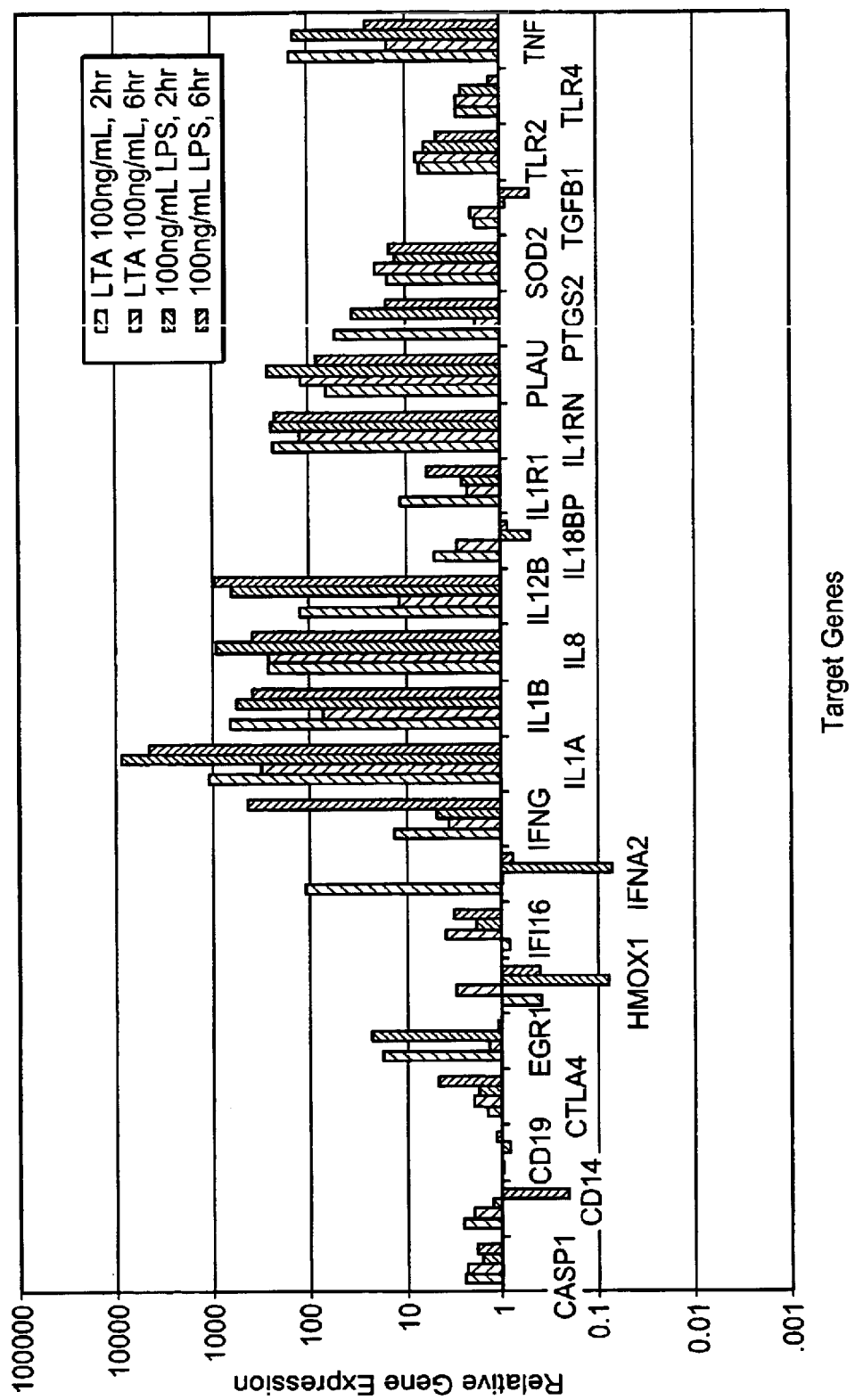

FIG. 27 uses a novel bacterial Gene Expression Panel of 24 genes, developed to discriminate various bacterial conditions in a host biological system.

Figure 28:
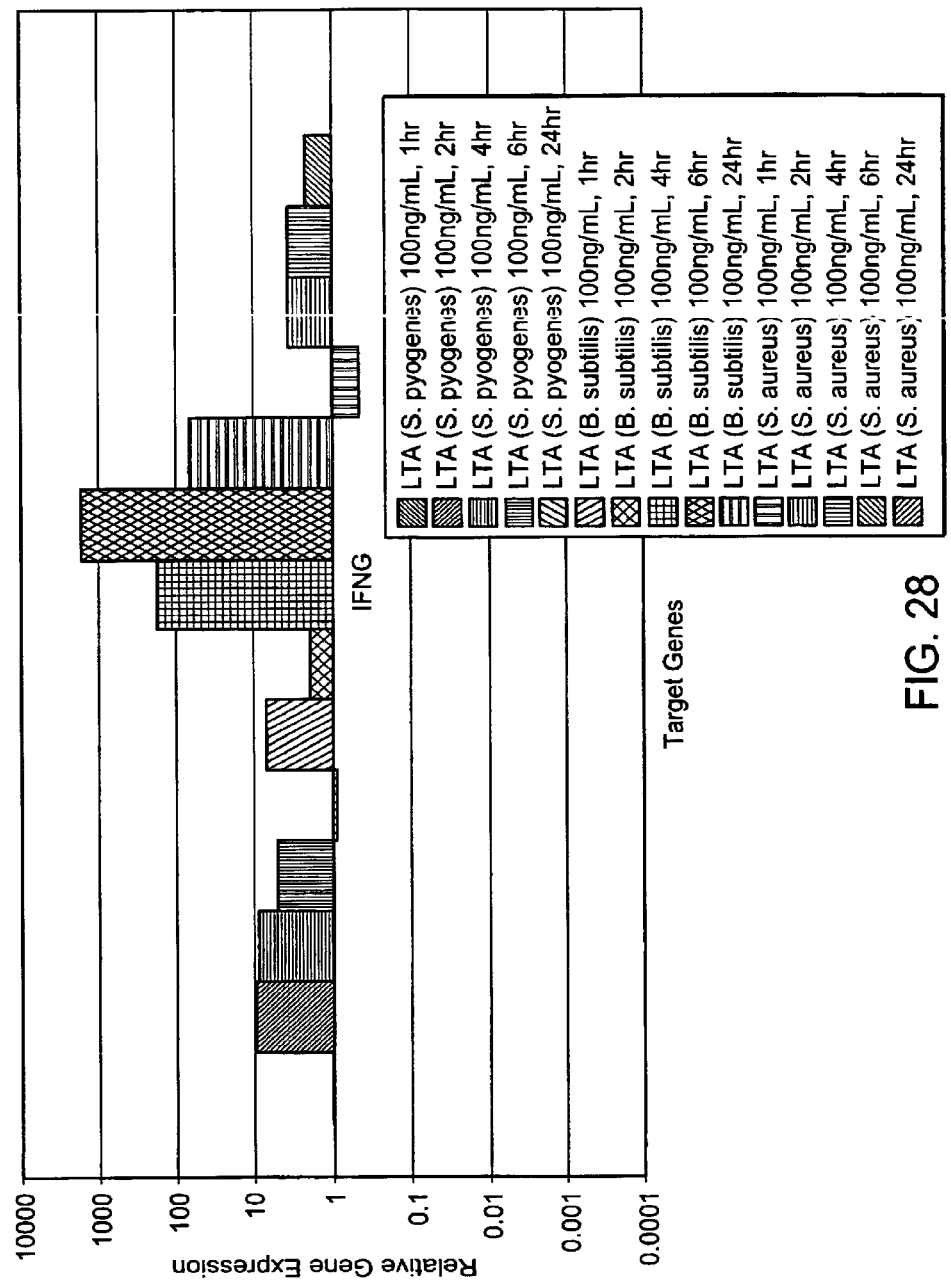

FIG. 28 shows differential expression for a single locus, IFNG, to LTA derived from three distinct sources: *S. pyogenes, B. subtilis,* and *S. aureus.*

Figure 29:
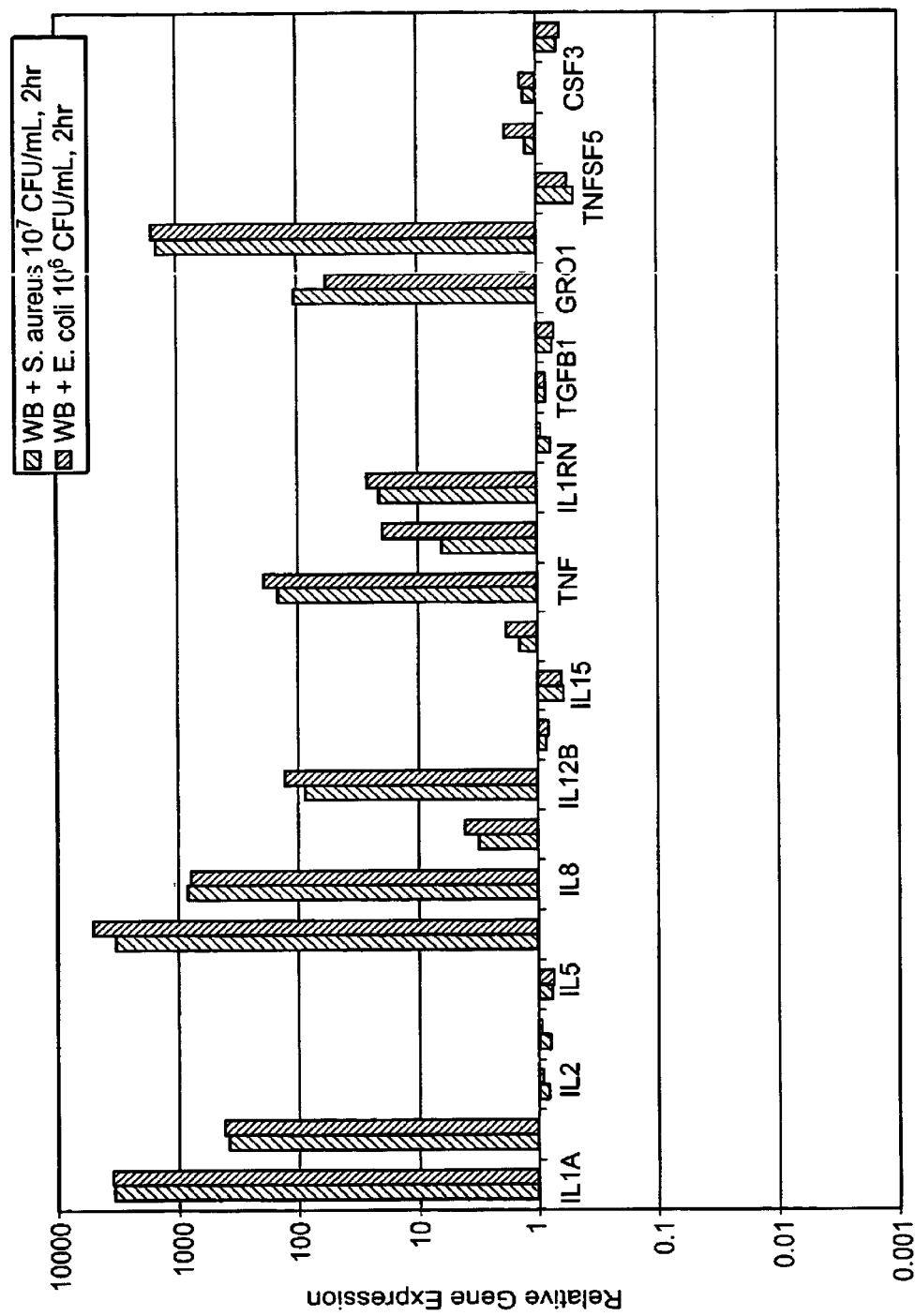
Figure 30:
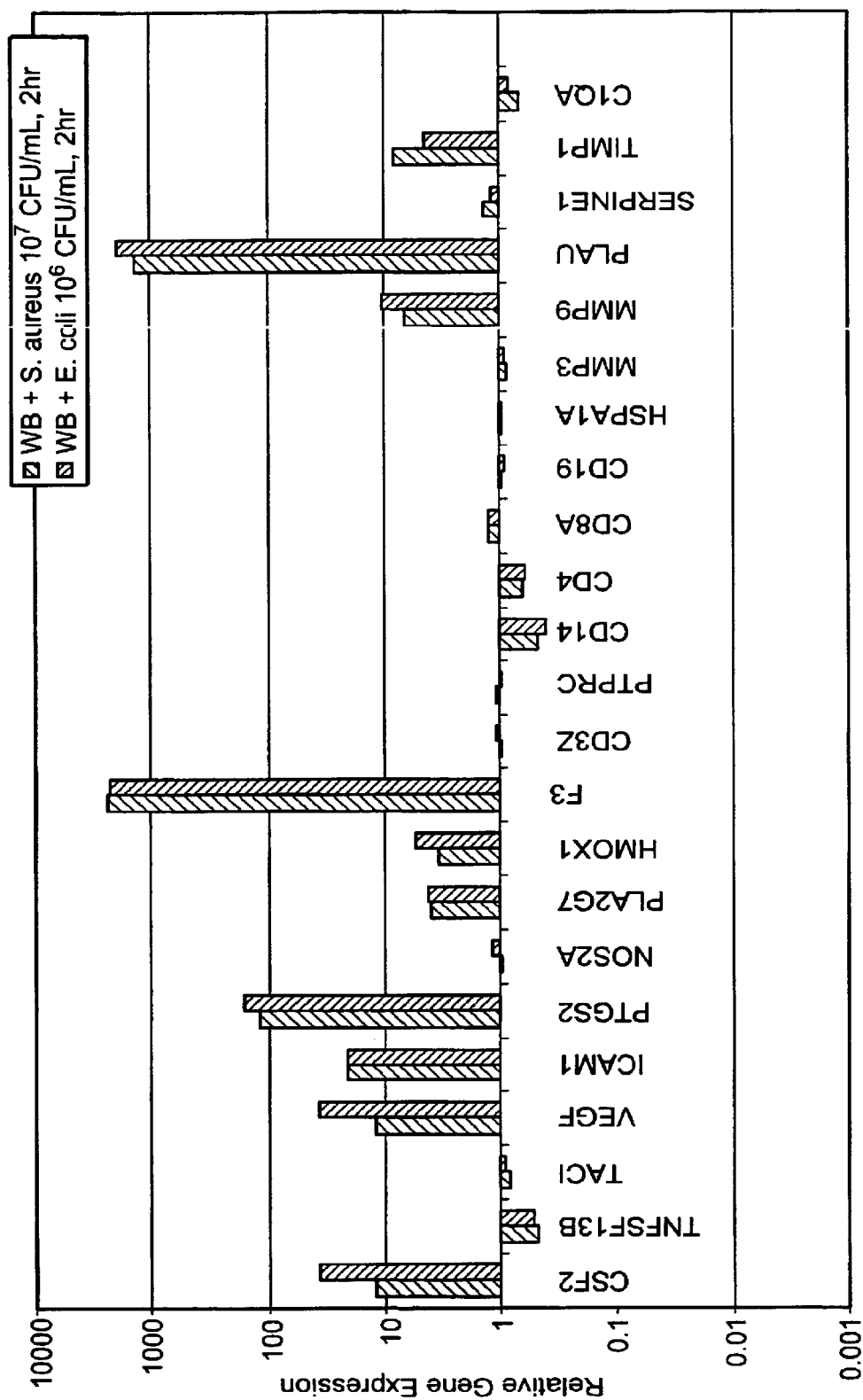

FIGS. 29 and 30 show the response after two hours of the Inflammation 48A and 48B loci respectively (discussed above in connection with FIGS. 6 and 7 respectively) in whole blood to administration of a Gram-positive and a Gram-negative organism.

Figure 31:
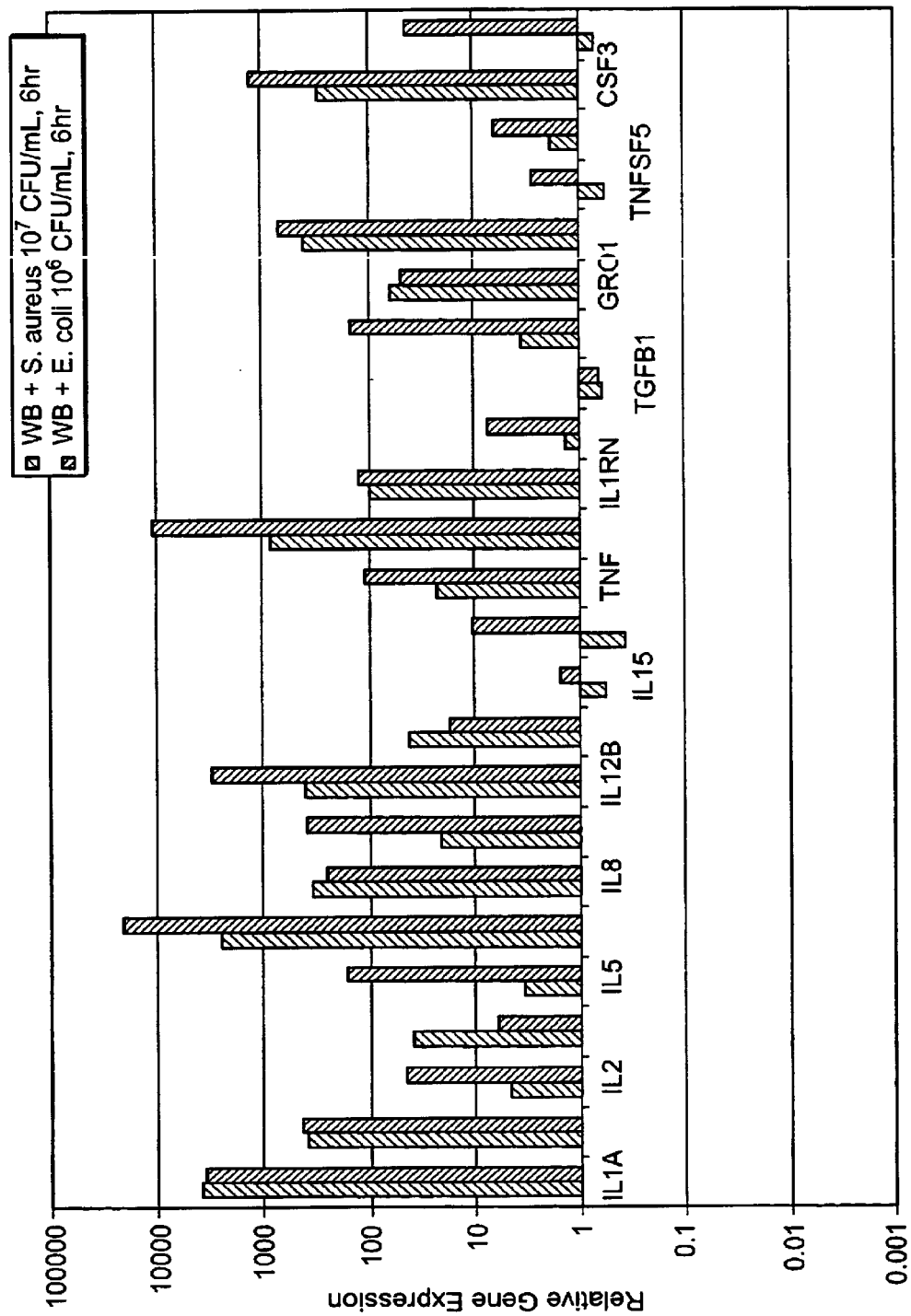
Figure 32:
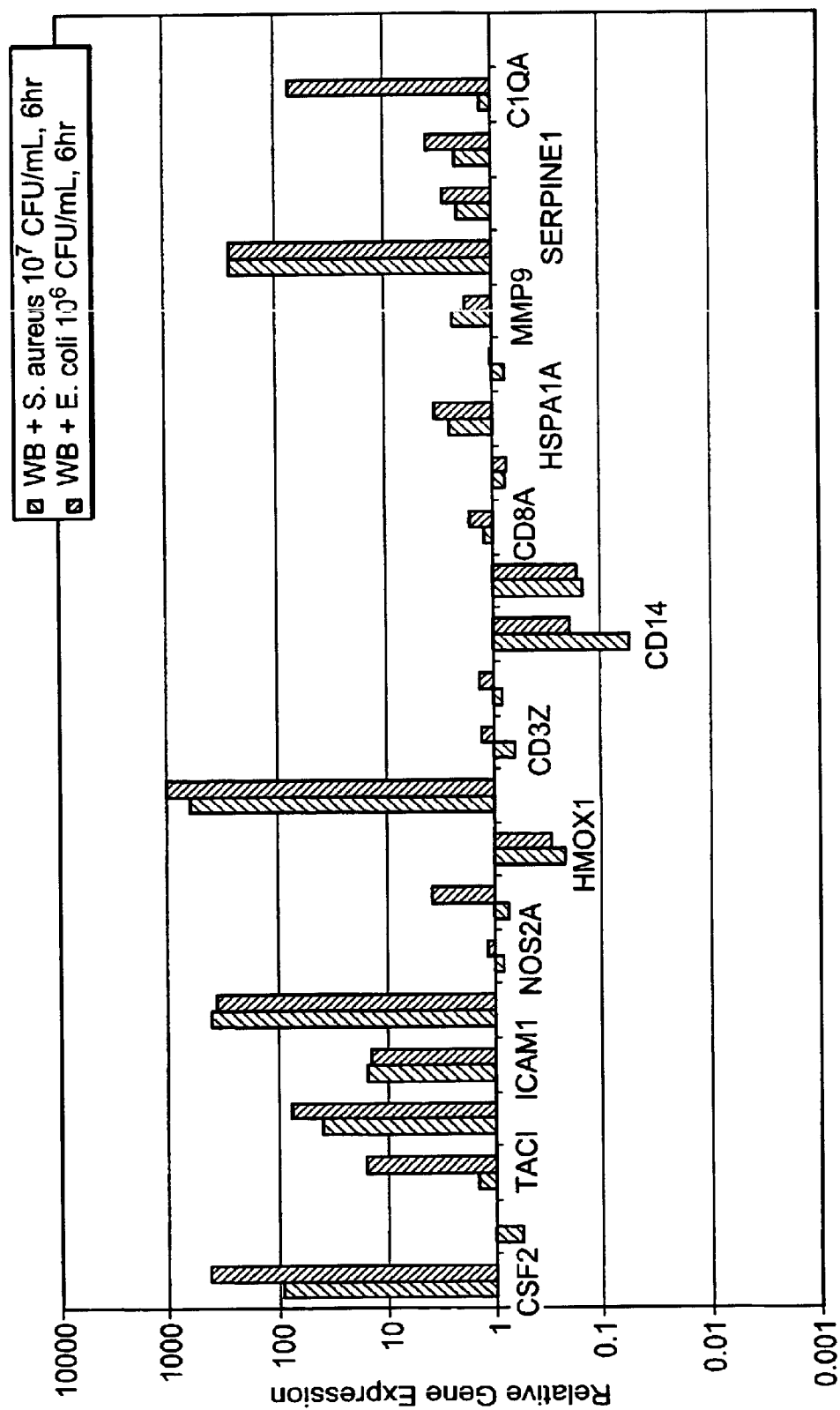

FIGS. 31 and 32 correspond to FIGS. 29 and 30 respectively and are similar to them, with the exception that the monitoring here occurs 6 hours after administration.

Figure 33:
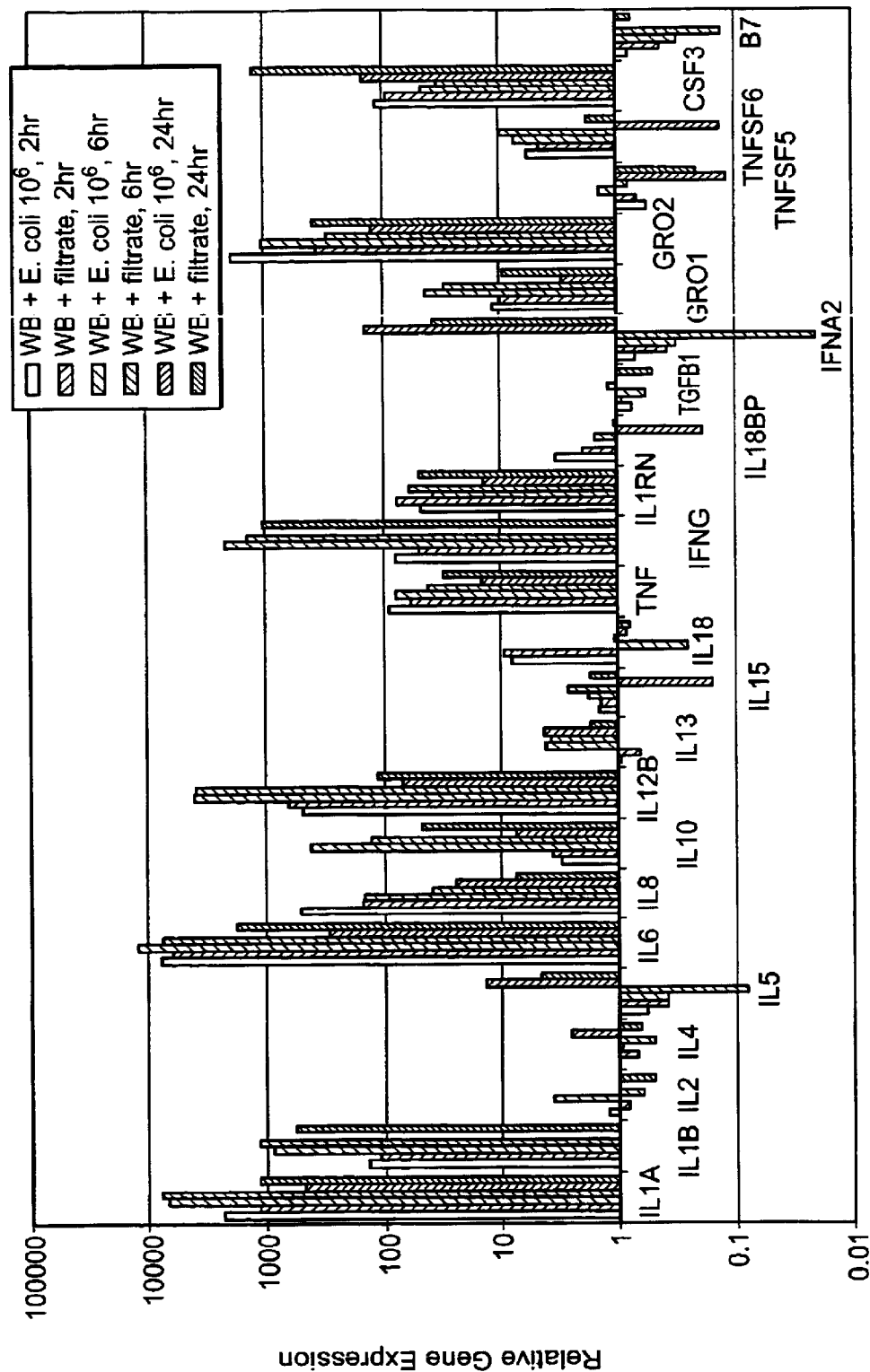

FIG. 33 compares the gene expression response induced by *E. coli* and by an organism-free *E. coli* filtrate.

Figure 34:
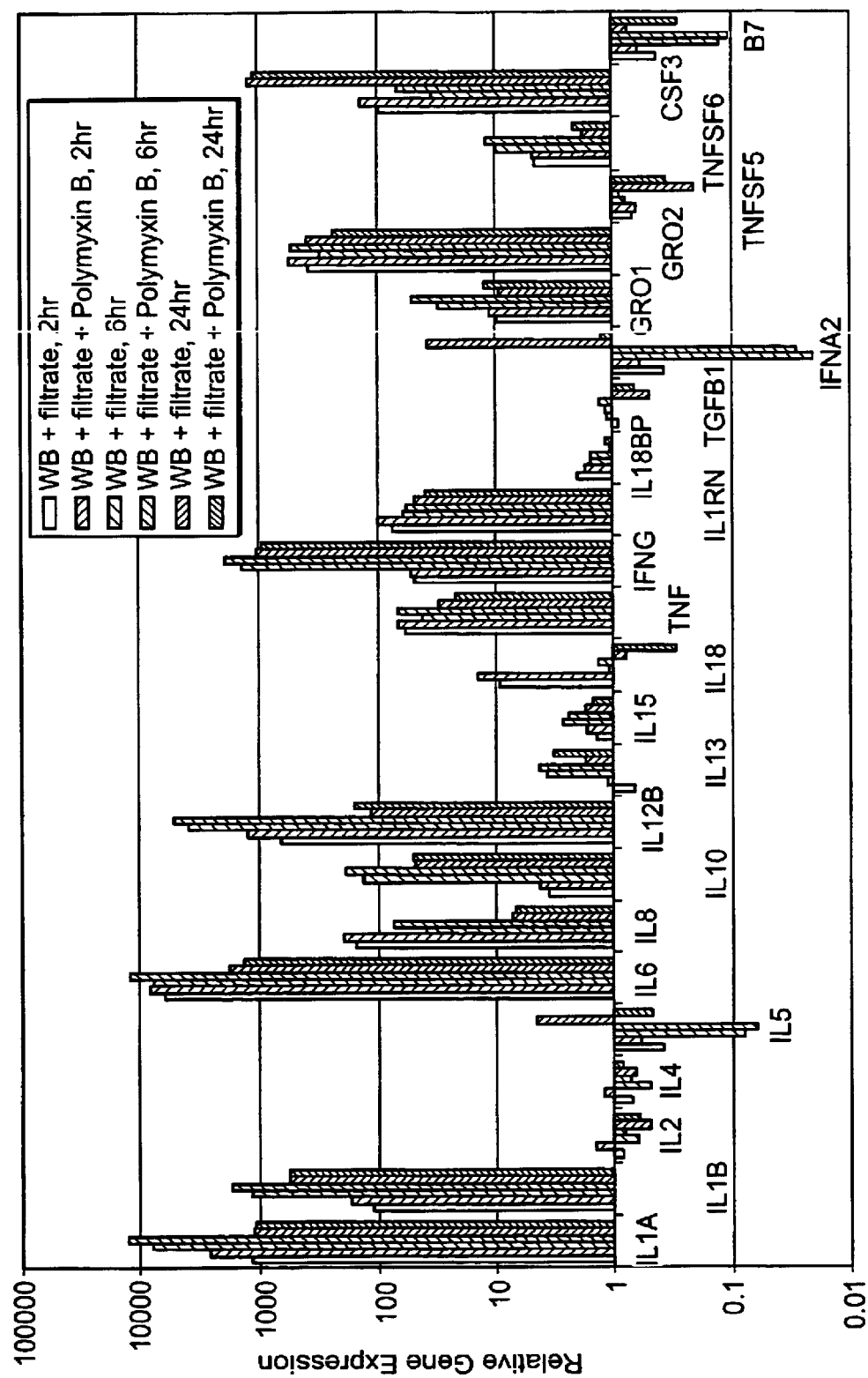

FIG. 34 is similar to FIG. 33, but here the compared responses are to stimuli from *E. coli* filtrate alone and from *E. coli* filtrate to which has been added polymyxin B.

Figure 35:
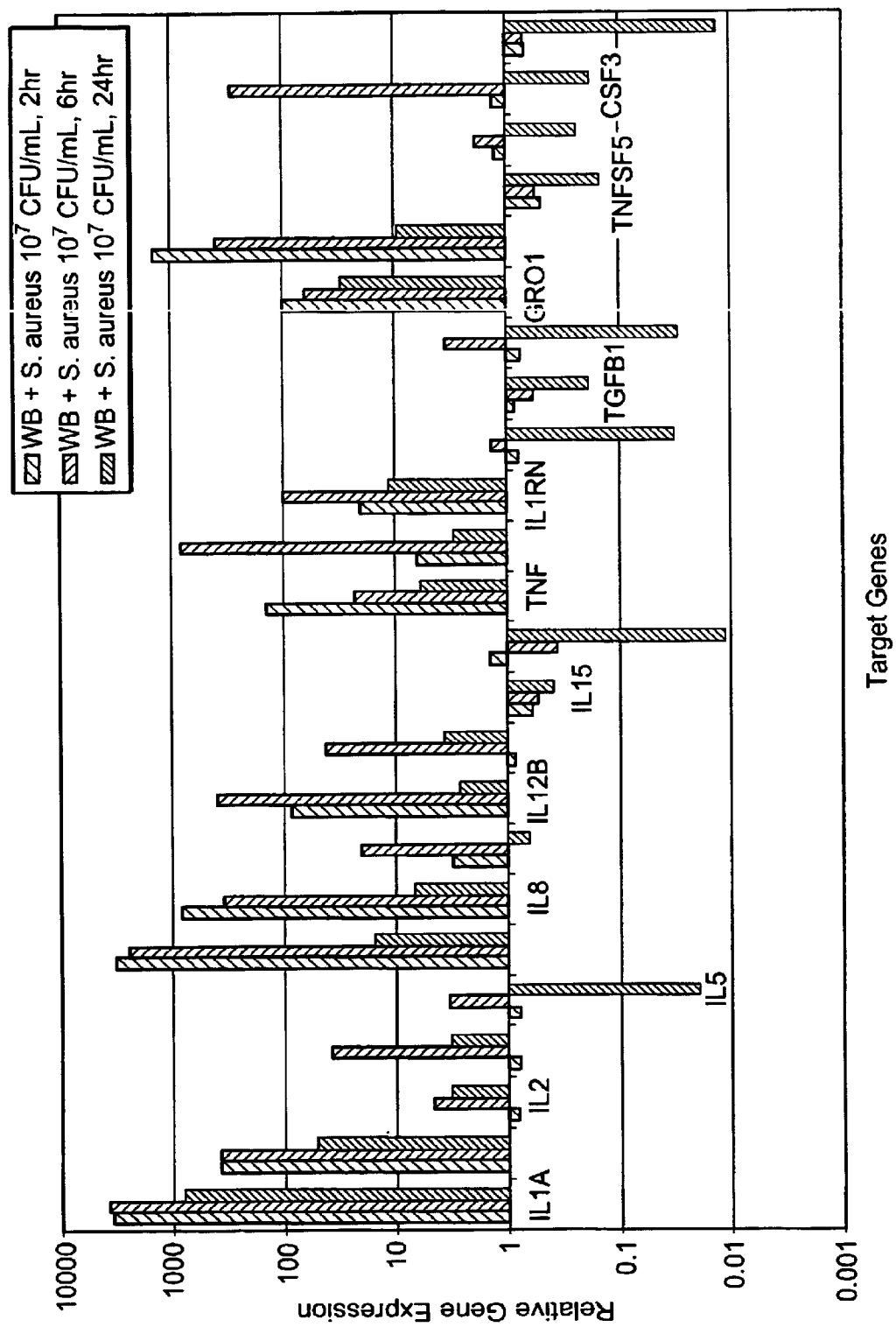

FIG. 35 illustrates the gene expression responses induced by *S. aureus* at 2, 6, and 24 hours after administration.

FIGS. 36 through 41 compare the gene expression induced by *E. coli* and *S. aureus* under various concentrations and times.

DETAILED DESCRIPTION OF SPECIFIC EMBODIMENTS

Definitions

For purposes of this description and the following claims, the following terms shall have the meanings indicated unless the context otherwise requires:

"Algorithm" is a set of rules for describing a biological condition. The rule set may be defined exclusively algebraically but may also include alternative or multiple decision points requiring domain-specific knowledge, expert interpretation or other clinical indicators.

An "agent" is a "composition" or a "stimulus", as those terms are defined herein, or a combination of a composition and a stimulus.

"Amplification" in the context of a quantitative RT-PCR assay is a function of the number of DNA replications that are tracked to provide a quantitative determination of its concentration. "Amplification" here refers to a degree of sensitivity and specificity of a quantitative assay technique. Accordingly, amplification provides a measurement of concentrations of constituents that is evaluated under conditions wherein the efficiency of amplification and therefore the degree of sensitivity and reproducibility for measuring all constituents is substantially similar.

A "baseline profile data set" is a set of values associated with constituents of a Gene Expression Panel resulting from evaluation of a biological sample (or population of samples) under a desired biological condition that is used for mathematically normative purposes. The desired biological condition may be, for example, the condition of a subject (or population of subjects) before exposure to an agent or in the presence of an untreated disease or in the absence of a disease. Alternatively, or in addition, the desired biological condition may be health of a subject or a population of subjects. Alternatively, or in addition, the desired biological condition may be that associated with a population subjects selected on the basis of at least one of age group, gender, ethnicity, geographic location, diet, medical disorder, clinical indicator, medication, physical activity, body mass, and environmental exposure.

A "biological condition" of a subject is the condition of the subject in a pertinent realm that is under observation, and such realm may include any aspect of the subject capable of being monitored for change in condition, such as health, disease including cancer; trauma; aging; infection; tissue degeneration; developmental steps; physical fitness; obesity, and mood. As can be seen, a condition in this context may be chronic or acute or simply transient. Moreover, a targeted biological condition may be manifest throughout the organism or population of cells or may be restricted to a specific organ (such as skin, heart, eye or blood), but in either case, the condition may be monitored directly by a sample of the affected population of cells or indirectly by a sample derived elsewhere from the subject. The term "biological condition" includes a "physiological condition".

"Bodyfluid" of a subject includes blood, urine, spinal fluid, lymph, mucosal secretions, prostatic fluid, semen, haemolymph or any other body fluid known in the art for a subject.

"Calibrated profile data set" is a function of a member of a first profile data set and a corresponding member of a baseline profile data set for a given constituent in a panel.

A "clinical indicator" is any physiological datum used alone or in conjunction with other data in evaluating the physiological condition of a collection of cells or of an organism. This term includes pre-clinical indicators.

A "composition" includes a chemical compound, a nutriceutical, a pharmaceutical, a homeopathic formulation, an allopathic formulation, a naturopathic formulation, a combination of compounds, a toxin, a food, a food supplement, a mineral, and a complex mixture of substances, in any physical state or in a combination of physical states.

To "derive" a profile data set from a sample includes determining a set of values associated with constituents of a Gene Expression Panel either (i) by direct measurement of such constituents in a biological sample or (ii) by measurement of such constituents in a second biological sample that has been exposed to the original sample or to matter derived from the original sample.

"Distinct RNA or protein constituent" in a panel of constituents is a distinct expressed product of a gene, whether RNA or protein. An "expression" product of a gene includes the gene product whether RNA or protein resulting from translation of the messenger RNA.

A "Gene Expression Panel" is an experimentally verified set of constituents, each constituent being a distinct expressed product of a gene, whether RNA or protein, wherein constituents of the set are selected so that their measurement provides a measurement of a targeted biological condition.

A "Gene Expression Profile" is a set of values associated with constituents of a Gene Expression Panel resulting from evaluation of a biological sample (or population of samples).

A "Gene Expression Profile Inflammatory Index" is the value of an index function that provides a mapping from an instance of a Gene Expression Profile into a single-valued measure of inflammatory condition.

The "health" of a subject includes mental, emotional, physical, spiritual, allopathic, naturopathic and homeopathic condition of the subject.

"Index" is an arithmetically or mathematically derived numerical characteristic developed for aid in simplifying or disclosing or informing the analysis of more complex quantitative information. A disease or population index may be determined by the application of a specific algorithm to a plurality of subjects or samples with a common biological condition.

"Inflammation" is used herein in the general medical sense of the word and may be an acute or chronic; simple or supporative; localized or disseminated; cellular and tissue response, initiated or sustained by any number of chemical, physical or biological agents or combination of agents.

"Inflammatory state" is used to indicate the relative biological condition of a subject resulting from inflammation, or characterizing the degree of inflammation A "large number" of data sets based on a common panel of genes is a number of data sets sufficiently large to permit a statistically significant conclusion to be drawn with respect to an instance of a data set based on the same panel.

A "normative" condition of a subject to whom a composition is to be administered means the condition of a subject before administration, even if the subject happens to be suffering from a disease.

A "panel" of genes is a set of genes including at least two constituents.

A "sample" from a subject may include a single cell or multiple cells or fragments of cells or an aliquot of body fluid, taken from the subject, by means including venipuncture, excretion, ejaculation, massage, biopsy, needle aspirate, lavage sample, scraping, surgical incision or intervention or other means known in the art.

A "Signature Profile" is an experimentally verified subset of a Gene Expression Profile selected to discriminate a biological condition, agent or physiological mechanism of action.

A "Signature Panel" is a subset of a Gene Expression Panel, the constituents of which are selected to permit discrimination of a biological condition, agent or physiological mechanism of action.

A "subject" is a cell, tissue, or organism, human or non-human, whether in vivo, ex vivo or in vitro, under observation. When we refer to evaluating the biological condition of a subject based on a sample from the subject, we include using blood or other tissue sample from a human subject to evaluate the human subject's condition; but we also include, for example, using a blood sample itself as the subject to evaluate, for example, the effect of therapy or an agent upon the sample.

A "stimulus" includes (i) a monitored physical interaction with a subject, for example ultraviolet A or B, or light therapy for seasonal affective disorder, or treatment of psoriasis with psoralen or treatment of melanoma with embedded radioactive seeds, other radiation exposure, and (ii) any monitored physical, mental, emotional, or spiritual activity or inactivity of a subject.

"Therapy" includes all interventions whether biological, chemical, physical, metaphysical, or combination of the foregoing, intended to sustain or alter the monitored biological condition of a subject.

The PCT patent application publication number WO 01/25473, published Apr. 12, 2001, entitled "Systems and Methods for Characterizing a Biological Condition or Agent Using Calibrated Gene Expression Profiles," filed for an invention by inventors herein, and which is herein incorporated by reference, discloses the use of Gene Expression Panels for the evaluation of (i) biological condition (including with respect to health and disease) and (ii) the effect of one or more agents on biological condition (including with respect to health, toxicity, therapeutic treatment and drug interaction).

In particular, Gene Expression Panels may be used for measurement of therapeutic efficacy of natural or synthetic compositions or stimuli that may be formulated individually or in combinations or mixtures for a range of targeted physiological conditions; prediction of toxicological effects and dose effectiveness of a composition or mixture of compositions for an individual or in a population; determination of how two or more different agents administered in a single treatment might interact so as to detect any of synergistic, additive, negative, neutral or toxic activity; performing pre-clinical and clinical trials by providing new criteria for pre-selecting subjects according to informative profile data sets for revealing disease status; and conducting preliminary dosage studies for these patients prior to conducting phase 1 or 2 trials. These Gene Expression Panels may be employed with respect to samples derived from subjects in order to evaluate their biological condition.

A Gene Expression Panel is selected in a manner so that quantitative measurement of RNA or protein constituents in the Panel constitutes a measurement of a biological condition of a subject. In one kind of arrangement, a calibrated profile data set is employed. Each member of the calibrated profile data set is a function of (i) a measure of a distinct constituent of a Gene Expression Panel and (ii) a baseline quantity.

We have found that valuable and unexpected results may be achieved when the quantitative measurement of constituents is performed under repeatable conditions (within a degree of repeatability of measurement of better than twenty percent, and preferably five percent or better, and more preferably three percent or better). For the purposes of this description and the following claims, we regard a degree of repeatability of measurement of better than twenty percent as providing measurement conditions that are "substantially repeatable". In particular, it is desirable that, each time a measurement is obtained corresponding to the level of expression of a constituent in a particular sample, substantially the same measurement should result for the substantially the same level of expression. In this manner, expression levels for a constituent in a Gene Expression Panel may be meaningfully compared from sample to sample. Even if the expression level measurements for a particular constituent are inaccurate (for example, say, 30% too low), the criterion of repeatability means that all measurements for this constituent, if skewed, will nevertheless be skewed systematically, and therefore measurements of expression level of the constituent may be compared meaningfully. In this fashion valuable information may be obtained and compared concerning expression of the constituent under varied circumstances.

In addition to the criterion of repeatability, it is desirable that a second criterion also be satisfied, namely that quantitative measurement of constituents is performed under conditions wherein efficiencies of amplification for all constituents are substantially similar (within one to two percent and typically one percent or less). When both of these criteria are satisfied, then measurement of the expression level of one constituent may be meaningfully compared with measurement of the expression level of another constituent in a given sample and from sample to sample.

Present embodiments relate to the use of an index or algorithm resulting from quantitative measurement of constituents, and optionally in addition, derived from either expert analysis or computational biology (a) in the analysis of complex data sets; (b) to control or normalize the influence of uninformative or otherwise minor variances in gene expression values between samples or subjects; (c) to simplify the characterization of a complex data set for comparison to other complex data sets, databases or indices or algorithms derived from complex data sets; (d) to monitor a biological condition of a subject; (e) for measurement of therapeutic efficacy of natural or synthetic compositions or stimuli that may be formulated individually or in combinations or mixtures for a range of targeted physiological conditions; (f) for predictions of toxicological effects and dose effectiveness of a composition or mixture of compositions for an individual or in a population; (g) for determination of how two or more different agents administered in a single treatment might interact so as to detect any of synergistic, additive, negative, neutral of toxic activity (h) for performing pre-clinical and clinical trials by providing new criteria for pre-selecting subjects according to informative profile data sets for revealing disease status and conducting preliminary dosage studies for these patients prior to conducting phase 1 or 2 trials.

Gene expression profiling and the use of index characterization for a particular condition or agent or both may be used to reduce the cost of phase 3 clinical trials and may be used beyond phase 3 trials; labeling for approved drugs; selection of suitable medication in a class of medications for a particular patient that is directed to their unique physiology; diagnosing or determining a prognosis of a medical condition or an infection which may precede onset of symptoms or alternatively diagnosing adverse side effects associated with administration of a therapeutic agent; managing the health care of a patient; and quality control for different batches of an agent or a mixture of agents.

The Subject

The methods disclosed here may be applied to cells of humans, mammals or other organisms without the need for undue experimentation by one of ordinary skill in the art because all cells transcribe RNA and it is known in the art how to extract RNA from all types of cells.

Selecting Constituents of a Gene Expression Panel

The general approach to selecting constituents of a Gene Expression Panel has been described in PCT application publication number WO 01/25473. We have designed and experimentally verified a wide range of Gene Expression Panels, each panel providing a quantitative measure, of biological condition, that is derived from a sample of blood or other tissue. For each panel, experiments have verified that a Gene Expression Profile using the panel's constituents is informative of a biological condition. (We show elsewhere that in being informative of biological condition, the Gene Expression Profile can be used to used, among other things, to measure the effectiveness of therapy, as well as to provide a target for therapeutic intervention.) Examples of Gene Expression Panels, along with a brief description of each panel constituent, are provided in tables attached hereto as follows:

Table 1. Inflammation Gene Expression Panel

Table 2. Diabetes Gene Expression Panel

Table 3. Prostate Gene Expression Panel

Table 4. Skin Response Gene Expression Panel

Table 5. Liver Metabolism and Disease Gene Expression Panel

Table 6. Endothelial Gene Expression Panel

Table 7. Cell Health and Apoptosis Gene Expression Panel

Table 8. Cytokine Gene Expression Panel

Table 9. TNF/IL1 Inhibition Gene Expression Panel

Table 10. Chemokine Gene Expression Panel

Table 11. Breast Cancer Gene Expression Panel

Table 12. Infectious Disease Gene Expression Panel

Other panels may be constructed and experimentally verified by one of ordinary skill in the art in accordance with the principles articulated in the present application.

Design of Assays

We commonly run a sample through a panel in quadruplicate; that is, a sample is divided into aliquots and for each aliquot we measure concentrations of each constituent in a Gene Expression Panel. Over a total of 900 constituent assays, with each assay conducted in quadruplicate, we found an average coefficient of variation, (standard deviation/average)*100, of less than 2 percent, typically less than 1 percent, among results for each assay. This figure is a measure of what we call "intra-assay variability". We have also conducted assays on different occasions using the same sample material. With 72 assays, resulting from concentration measurements of constituents in a panel of 24 members, and such concentration measurements determined on three different occasions over time, we found an average coefficient of variation of less than 5 percent, typically less than 2 percent. We regard this as a measure of what we call "inter-assay variability".

We have found it valuable in using the quadruplicate test results to identify and eliminate data points that are statistical "outliers"; such data points are those that differ by a percentage greater, for example, than 3% of the average of all four values and that do not result from any systematic skew that is greater, for example, than 1%. Moreover, if more than one data point in a set of four is excluded by this procedure, then all data for the relevant constituent is discarded.

Measurement of Gene Expression for a Constituent in the Panel

For measuring the amount of a particular RNA in a sample, we have used methods known to one of ordinary skill in the art to extract and quantify transcribed RNA from a sample with respect to a constituent of a Gene Expression Panel. (See detailed protocols below. Also see PCT application publication number WO 98/24935 herein incorporated by reference for RNA analysis protocols). Briefly, RNA is extracted from a sample such as a tissue, body fluid, or culture medium in which a population of a subject might be growing. For example, cells may be lysed and RNA eluted in a suitable solution in which to conduct a DNAse reaction. First strand synthesis may be performed using a reverse transcriptase. Gene amplification, more specifically quantitative PCR assays, can then conducted and the gene of interest size calibrated against a marker such as 18S rRNA (Hirayama et al., Blood 92, 1998: 46–52). Samples are measured in multiple duplicates, for example, 4 replicates. Relative quantitation of the mRNA is determined by the difference in threshhold cycles between the internal control and the gene of interest. In an embodiment of the invention, quantitative PCR is performed using amplification, reporting agents and instruments such as those supplied commercially by Applied Biosystems (Foster City, Calif.). Given a defined efficiency of amplification of target transcripts, the point (e.g., cycle number) that signal from amplified target template is detectable may be directly related to the amount of specific message transcript in the measured sample. Similarly, other quantifiable signals such as fluorescence, enzyme activity, disintegrations per minute, absorbance, etc., when correlated to a known concentration of target templates (e.g., a reference standard curve) or normalized to a standard with limited variability can be used to quantify the number of target templates in an unknown sample.

Although not limited to amplification methods, quantitative gene expression techniques may utilize amplification of the target transcript. Alternatively or in combination with amplification of the target transcript, amplification of the reporter signal may also be used. Amplification of the target template may be accomplished by isothermic gene amplification strategies, or by gene amplification by thermal cycling such as PCR.

It is desirable to obtain a definable and reproducible correlation between the amplified target or reporter and the concentration of starting templates. We have discovered that this objective can be achieved by careful attention to, for example, consistent primer-template ratios and a strict adherence to a narrow permissible level of experimental amplification efficiencies (for example 99.0 to 100% relative efficiency, typically 99.8 to 100% relative efficiency). For example, in determining gene expression levels with regard to a single Gene Expression Profile, it is necessary that all constituents of the panels maintain a similar and limited range of primer template ratios (for example, within a 10-fold range) and amplification efficiencies (within, for example, less than 1%) to permit accurate and precise relative measurements for each constituent. We regard amplification efficiencies as being "substantially similar", for the purposes of this description and the following claims, if they differ by no more than approximately 10%. Preferably they should differ by less than approximately 2% and more preferably by less than approximately 1%. These constraints should be observed over the entire range of concentration levels to be measured associated with the relevant biological condition. While it is thus necessary for various embodiments herein to satisfy criteria that measurements are achieved under measurement conditions that are substantially repeatable and wherein specificity and efficiencies of amplification for all constituents are substantially similar, nevertheless, it is within the scope of the present invention as claimed herein to achieve such measurement conditions by adjusting assay results that do not satisfy these criteria directly, in such a manner as to compensate for errors, so that the criteria are satisfied after suitable adjustment of assay results.

In practice, we run tests to assure that these conditions are satisfied. For example, we typically design and manufacture a number of primer-probe sets, and determine experimentally which set gives the best performance. Even though primer-probe design and manufacture can be enhanced using computer techniques known in the art, and notwithstanding common practice, we still find that experimental validation is useful. Moreover, in the course of experimental validation, we associate with the selected primer-probe combination a set of features:

The reverse primer should be complementary to the coding DNA strand. In one embodiment, the primer should be located across an intron-exon junction, with not more than three bases of the three-prime end of the reverse primer complementary to the proximal exon. (If more than three bases are complementary, then it would tend to competitively amplify genomic DNA.)

In an embodiment of the invention, the primer probe should amplify cDNA of less than 110 bases in length and should not amplify genomic DNA or transcripts or cDNA from related but biologically irrelevant loci.

A suitable target of the selected primer probe is first strand cDNA, which may be prepared, in one embodiment, is described as follows:

(a) Use of whole blood for ex vivo assessment of a biological condition affected by an agent.

Human blood is obtained by venipuncture and prepared for assay by separating samples for baseline, no stimulus, and stimulus with sufficient volume for at least three time points. Typical stimuli include lipopolysaccharide (LPS), phytohemagglutinin (PHA) and heat-killed *staphylococci* (HKS) or carrageean and may be used individually (typically) or in combination. The aliquots of heparinized, whole blood are mixed without stimulus and held at 37° C. in an atmosphere of 5% CO2 for 30 minutes. Stimulus is added at varying concentrations, mixed and held loosely capped at 37° C. for 30 min. Additional test compounds may be added at this point and held for varying times depending on the expected pharmacokinetics of the test compound. At defined times, cells are collected by centrifugation, the plasma removed and RNA extracted by various standard means.

Nucleic acids, RNA and or DNA are purified from cells, tissues or fluids of the test population or indicator cell lines. RNA is preferentially obtained from the nucleic acid mix using a variety of standard procedures (or RNA Isolation Strategies, pp. 55–104, in *RNA Methodologies, A laboratory guide for isolation and characterization*, 2nd edition, 1998, Robert E. Farrell, Jr., Ed., Academic Press), in the present using a filter-based RNA isolation system from Ambion (RNAqueous™, Phenol-free Total RNA Isolation Kit, Catalog #1912, version 9908; Austin, Tex.).

In accordance with one procedure, the whole blood assay for Gene Expression Profiles determination was carried out as follows: Human whole blood was drawn into 10 mL Vacutainer tubes with Sodium Heparin. Blood samples were mixed by gently inverting tubes 4–5 times. The blood was used within 10–15 minutes of draw. In the experiments, blood was diluted 2-fold, i.e. per sample per time point, 0.6 mL whole blood +0.6 mL stimulus. The assay medium was prepared and the stimulus added as appropriate.

A quantity (0.6 mL) of whole blood was then added into each 12×75 mm polypropylene tube. 0.6 mL of 2× LPS (from *E. coli* serotye 0127:B8, Sigma#L3880 or serotype 055, Sigma #L4005, 10 ng/ml, subject to change in different lots) into LPS tubes was added. Next, 0.6 mL assay medium was added to the "control" tubes with duplicate tubes for each condition. The caps were closed tightly. The tubes were inverted 2–3 times to mix samples. Caps were loosened to first stop and the tubes incubated @ 37° C., 5% CO2 for 6 hours. At 6 hours, samples were gently mixed to resuspend blood cells, and 1 mL was removed from each tube (using a micropipettor with barrier tip), and transfered to a 2 mL "dolphin" microfuge tube (Costar #3213).

The samples were then centrifuged for 5 min at 500×g, ambient temperature (IEC centrifuge or equivalent, in microfuge tube adapters in swinging bucket), and as much serum from each tube was removed as possible and discarded. Cell pellets were placed on ice; and RNA extracted as soon as possible using an Ambion RNAqueous kit.

(b) Amplification Strategies.

Specific RNAs are amplified using message specific primers or random primers. The specific primers are synthesized from data obtained from public databases (e.g., Unigene, National Center for Biotechnology Information, National Library of Medicine, Bethesda, Md.), including information from genomic and cDNA libraries obtained from humans and other animals. Primers are chosen to preferentially amplify from specific RNAs obtained from the test or indicator samples, see, for example, RT PCR, Chapter 15 in *RNA Methodologies, A laboratory guide for isolation and characterization*, 2nd edition, 1998, Robert E. Farrell, Jr., Ed., Academic Press; or Chapter 22 pp.143–151, *RNA isolation and characterization protocols*, Methods in molecular biology, Volume 86, 1998, R. Rapley and D. L. Manning Eds., Human Press, or 14 in Statistical refinement of primer design parameters, Chapter 5, pp.55–72, PCR applications: protocols for functional genomics, M. A. Innis, D. H. Gelfand and J. J. Sninsky, Eds., 1999, Academic Press). Amplifications are carried out in either isothermic conditions or using a thermal cycler (for example, a ABI 9600 or 9700 or 7700 obtained from Applied Biosystems, Foster City, Calif.; see Nucleic acid detection methods, pp. 1–24, in *Molecular methods for virus detection*, D. L. Wiedbrauk and D. H., Farkas, Eds., 1995, Academic Press). Amplified nucleic acids are detected using fluorescent-tagged detection primers (see, for example, Taqman™ PCR Reagent Kit, Protocol, part number 402823 revision A, 1996, Applied Biosystems, Foster City Calif.) that are identified and synthesized from publicly known databases as described for the amplification primers. In the present case, amplified DNA is detected and quantified using the ABI Prism 7700 Sequence Detection System obtained from Applied Biosystems (Foster City, Calif.). Amounts of specific RNAs contained in the test sample or obtained from the indicator cell lines can be related to the relative quantity of fluorescence observed (see for example, Advances in quantitative PCR technology: 5' nuclease assays, Y. S. Lie and C. J. Petropolus, Current Opinion in Biotechnology, 1998, 9:43–48, or Rapid thermal cycling and PCR kinetics, pp. 211–229, chapter 14 in PCR applications: protocols for functional genomics, M. A. Innis, D. H. Gelfand and J. J. Sninsky, Eds., 1999, Academic Press).

As a particular implementation of the approach described here, we describe in detail a procedure for synthesis of first strand cDNA for use in PCR. This procedure can be used for both whole blood RNA and RNA extracted from cultured cells (i.e. THP-1 cells).

Materials

1. Applied Biosystems TAQMAN Reverse Transcription Reagents Kit (P/N 808-0234). Kit Components: 10× TaqMan RT Buffer, 25 mM Magnesium chloride, deoxyNTPs mixture, Random Hexamers, RNase Inhibitor, MultiScribe Reverse Transcriptase (50 U/mL) (2) RNase/DNase free water (DEPC Treated Water from Ambion (P/N 9915G), or equivalent)

Methods

1. Place RNase Inhibitor and MultiScribe Reverse Transcriptase on ice immediately. All other reagents can be thawed at room temperature and then placed on ice.

2. Remove RNA samples from −80° C. freezer and thaw at room temperature and then place immediately on ice.

3. Prepare the following cocktail of Reverse Transcriptase Reagents for each 100 mL RT reaction (for multiple samples, prepare extra cocktail to allow for pipetting error):

|  | 1 reaction (mL) | 11X, e.g. 10 samples (mL) |
| --- | --- | --- |
| 10X RT Buffer | 10.0 | 110.0 |
| 25 mM MgCl2 | 22.0 | 242.0 |
| dNTPs | 20.0 | 220.0 |
| Random Hexamers | 5.0 | 55.0 |
| RNAse Inhibitor | 2.0 | 22.0 |
| Reverse Transcriptase | 2.5 | 27.5 |
| Water | 18.5 | 203.5 |
| Total: | 80.0 | 880.0 (80 mL per sample) |

4. Bring each RNA sample to a total volume of 20 mL in a 1.5 mL microcentrifuge tube (for example, for THP-1 RNA, remove 10 mL RNA and dilute to 20 mL with RNase/DNase free water, for whole blood RNA use 20 mL total RNA) and add 80 mL RT reaction mix from step 5, 2, 3. Mix by pipetting up and down.

5. Incubate sample at room temperature for 10 minutes.

6. Incubate sample at 37° C. for 1 hour.

7. Incubate sample at 90° C. for 10 minutes.

8. Quick spin samples in microcentrifuge.

9. Place sample on ice if doing PCR immediately, otherwise store sample at 20° C. for future use.

10. PCR QC should be run on all RT samples using 18S and b-actin (see SOP 200-020).

The use of the primer probe with the first strand cDNA as described above to permit measurement of constituents of a Gene Expression Panel is as follows:

Set up of a 24-gene Human Gene Expression Panel for Inflammation.

Materials 1. 20× Primer/Probe Mix for each gene of interest.
2. 20× Primer/Probe Mix for 18S endogenous control.
3. 2× Taqman Universal PCR Master Mix.
4. cDNA transcribed from RNA extracted from cells.
5. Applied Biosystems 96-Well Optical Reaction Plates.
6. Applied Biosystems Optical Caps, or optical-clear film.
7. Applied Biosystem Prism 7700 Sequence Detector.

Methods

1. Make stocks of each Primer/Probe mix containing the Primer/Probe for the gene of interest, Primer/Probe for 18S endogenous control, and 2× PCR Master Mix as follows. Make sufficient excess to allow for pipetting error e.g. approximately 10% excess. The following example illustrates a typical set up for one gene with quadruplicate samples testing two conditions (2 plates).

|  | 1X (1 well) | 9X (2 plates worth) |
| --- | --- | --- |
| 2X Master Mix | 12.50 | 112.50 |
| 20X 18S Primer/Probe Mix | 1.25 | 11.25 |
| 20X Gene of interest Primer/Probe Mix | 1.25 | 11.25 |
| Total | 15.00 | 135.00 |

2. Make stocks of cDNA targets by diluting 95 µl of cDNA into 2000 µl of water. The amount of cDNA is adjusted to give Ct values between 10 and 18, typically between 12 and 13.

3. Pipette 15 µl of Primer/Probe mix into the appropriate wells of an Applied Biosystems 96-Well Optical Reaction Plate.

4. Pipette 10 µl of cDNA stock solution into each well of the Applied Biosystems 96-Well Optical Reaction Plate.

5. Seal the plate with Applied Biosystems Optical Caps, or optical-clear film.

6. Analyze the plate on the AB Prism 7700 Sequence Detector.

Methods herein may also be applied using proteins where sensitive quantitative techniques, such as an Enzyme Linked ImmunoSorbent Assay (ELISA) or mass spectroscopy, are available and well-known in the art for measuring the amount of a protein constituent. (see WO 98/24935 herein incorporated by reference).

Baseline Profile Data Sets

The analyses of samples from single individuals and from large groups of individuals provide a library of profile data sets relating to a particular panel or series of panels. These profile data sets may be stored as records in a library for use as baseline profile data sets. As the term "baseline" suggests, the stored baseline profile data sets serve as comparators for providing a calibrated profile data set that is informative about a biological condition or agent. Baseline profile data sets may be stored in libraries and classified in a number of cross-referential ways. One form of classification may rely on the characteristics of the panels from which the data sets are derived. Another form of classification may be by particular biological condition. The concept of biological condition encompasses any state in which a cell or population of cells may be found at any one time. This state may reflect geography of samples, sex of subjects or any other discriminator. Some of the discriminators may overlap. The libraries may also be accessed for records associated with a single subject or particular clinical trial. The classification of baseline profile data sets may further be annotated with medical information about a particular subject, a medical condition, a particular agent etc.

The choice of a baseline profile data set for creating a calibrated profile data set is related to the biological condition to be evaluated, monitored, or predicted, as well as, the intended use of the calibrated panel, e.g., as to monitor drug development, quality control or other uses. It may be desirable to access baseline profile data sets from the same subject for whom a first profile data set is obtained or from different subject at varying times, exposures to stimuli, drugs or complex compounds; or may be derived from like or dissimilar populations.

Figure 5:
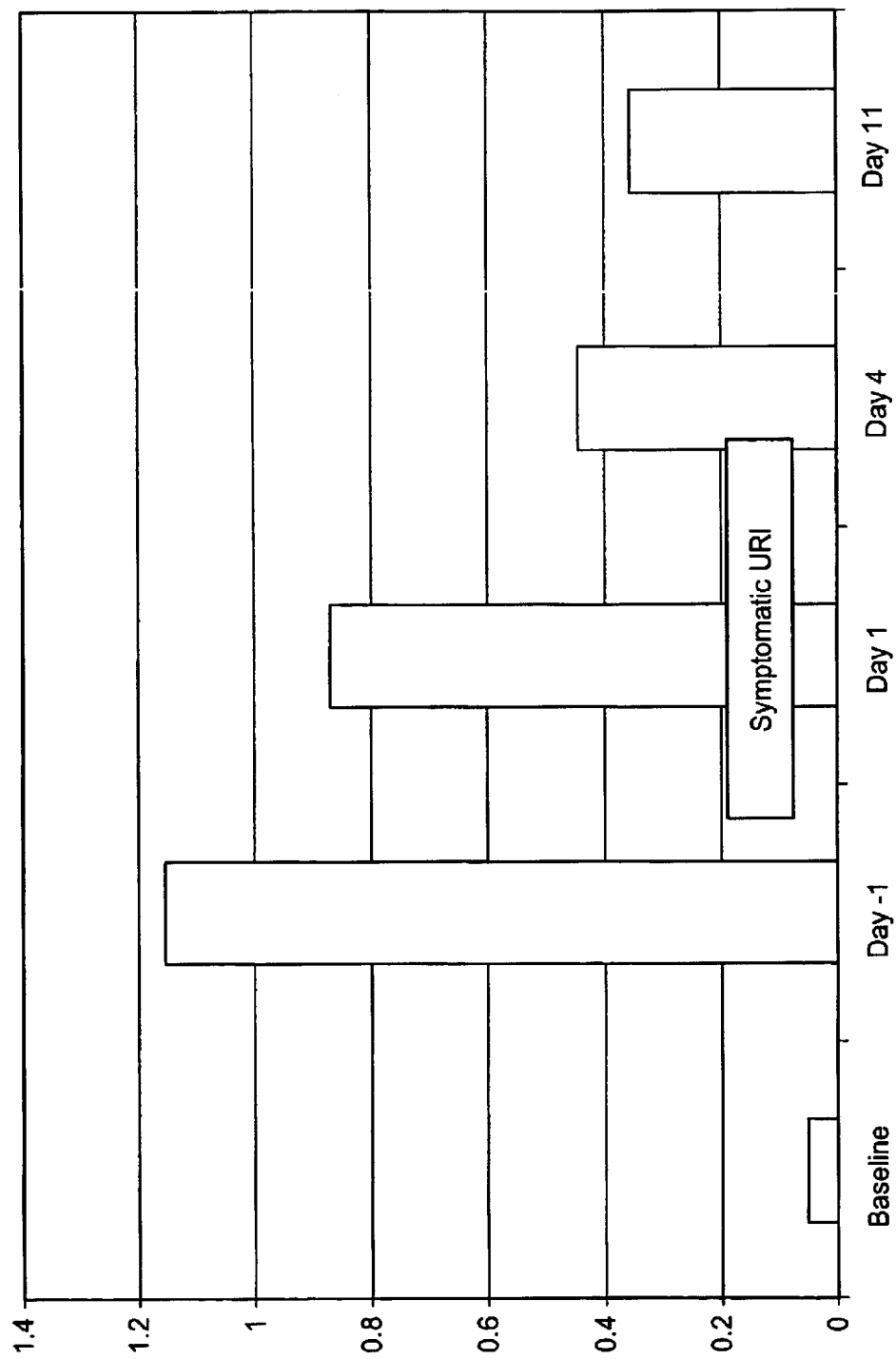
FIG. 5 shows a Viral Response Index for monitoring the progress of an upper respiratory infection (URI).

The profile data set may arise from the same subject for which the first data set is obtained, where the sample is taken at a separate or similar time, a different or similar site or in a different or similar physiological condition. For example, FIG. 5 provides a protocol in which the sample is taken before stimulation or after stimulation. The profile data set obtained from the unstimulated sample may serve as a baseline profile data set for the sample taken after stimulation. The baseline data set may also be derived from a library containing profile data sets of a population of subjects having some defining characteristic or biological condition. The baseline profile data set may also correspond to some ex vivo or in vitro properties associated with an in vitro cell culture. The resultant calibrated profile data sets may then be stored as a record in a database or library (FIG. 6) along with or separate from the baseline profile data base and optionally the first profile data set although the first profile data set would normally become incorporated into a baseline profile data set under suitable classification criteria. The remarkable consistency of Gene Expression Profiles associated with a given biological condition makes it valuable to store profile data, which can be used, among other things for normative reference purposes. The normative reference can serve to indicate the degree to which a subject conforms to a given biological condition (healthy or diseased) and, alternatively or in addition, to provide a target for clinical intervention.

Selected baseline profile data sets may be also be used as a standard by which to judge manufacturing lots in terms of efficacy, toxicity, etc. Where the effect of a therapeutic agent is being measured, the baseline data set may correspond to Gene Expression Profiles taken before administration of the agent. Where quality control for a newly manufactured product is being determined, the baseline data set may correspond with a gold standard for that product. However, any suitable normalization techniques may be employed. For example, an average baseline profile data set is obtained from authentic material of a naturally grown herbal nutriceutical and compared over time and over different lots in order to demonstrate consistency, or lack of consistency, in lots of compounds prepared for release.

Calibrated Data

Given the repeatability we have achieved in measurement of gene expression, described above in connection with "Gene Expression Panels" and "gene amplification", we conclude that where differences occur in measurement under such conditions, the differences are attributable to differences in biological condition. Thus we have found that calibrated profile data sets are highly reproducible in samples taken from the same individual under the same conditions. We have similarly found that calibrated profile data sets are reproducible in samples that are repeatedly tested. We have also found repeated instances wherein calibrated profile data sets obtained when samples from a subject are exposed ex vivo to a compound are comparable to calibrated profile data from a sample that has been exposed to a sample in vivo. We have also found, importantly, that an indicator cell line treated with an agent can in many cases provide calibrated profile data sets comparable to those obtained from in vivo or ex vivo populations of cells. Moreover, we have found that administering a sample from a subject onto indicator cells can provide informative calibrated profile data sets with respect to the biological condition of the subject including the health, disease states, therapeutic interventions, aging or exposure to environmental stimuli or toxins of the subject.

Calculation of Calibrated Profile Data Sets and Computational Aids

The calibrated profile data set may be expressed in a spreadsheet or represented graphically for example, in a bar chart or tabular form but may also be expressed in a three dimensional representation. The function relating the baseline and profile data may be a ratio expressed as a logarithm. The constituent may be itemized on the x-axis and the logarithmic scale may be on the y-axis. Members of a calibrated data set may be expressed as a positive value representing a relative enhancement of gene expression or as a negative value representing a relative reduction in gene expression with respect to the baseline.

Each member of the calibrated profile data set should be reproducible within a range with respect to similar samples taken from the subject under similar conditions. For example, the calibrated profile data sets may be reproducible within one order of magnitude with respect to similar samples taken from the subject under similar conditions. More particularly, the members may be reproducible within 50%, more particularly reproducible within 20%, and typically within 10%. In accordance with embodiments of the invention, a pattern of increasing, decreasing and no change in relative gene expression from each of a plurality of gene loci examined in the Gene Expression Panel may be used to prepare a calibrated profile set that is informative with regards to a biological condition, biological efficacy of an agent treatment conditions or for comparison to populations. Patterns of this nature may be used to identify likely candidates for a drug trial, used alone or in combination with other clinical indicators to be diagnostic or prognostic with respect to a biological condition or may be used to guide the development of a pharmaceutical or nutriceutical through manufacture, testing and marketing.

Figure 8:
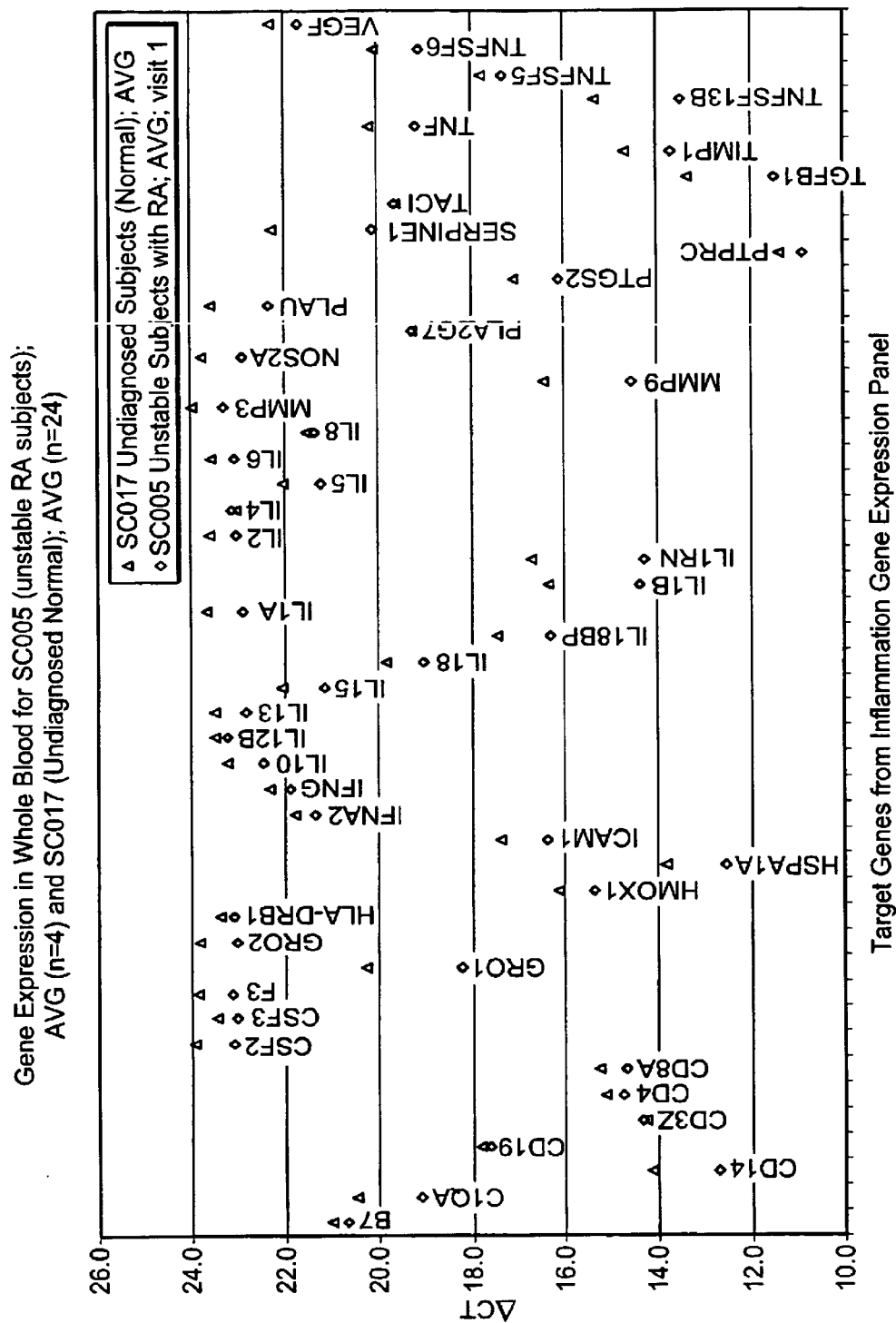
FIG. 8 compares a normal population with a rheumatoid arthritis population derived from a longitudinal study.

The numerical data obtained from quantitative gene expression and numerical data from calibrated gene expression relative to a baseline profile data set may be stored in databases or digital storage mediums and may retrieved for purposes including managing patient health care or for conducting clinical trials or for characterizing a drug. The data may be transferred in physical or wireless networks via the World Wide Web, email, or internet access site for example or by hard copy so as to be collected and pooled from distant geographic sites (FIG. 8).

In an embodiment of the present invention, a descriptive record is stored in a single database or multiple databases where the stored data includes the raw gene expression data (first profile data set) prior to transformation by use of a baseline profile data set, as well as a record of the baseline profile data set used to generate the calibrated profile data set including for example, annotations regarding whether the baseline profile data set is derived from a particular Signature Panel and any other annotation that facilitates interpretation and use of the data.

Because the data is in a universal format, data handling may readily be done with a computer. The data is organized so as to provide an output optionally corresponding to a graphical representation of a calibrated data set.

For example, a distinct sample derived from a subject being at least one of RNA or protein may be denoted as $P_j$. The first profile data set derived from sample $P_j$ is denoted $M_j$, where $M_j$ is a quantitative measure of a distinct RNA or protein constituent of $P_j$. The record Ri is a ratio of M and P and may be annotated with additional data on the subject relating to, for example, age, diet, ethnicity, gender, geographic location, medical disorder, mental disorder, medication, physical activity, body mass and environmental exposure. Moreover, data handling may further include accessing data from a second condition database which may contain additional medical data not presently held with the calibrated profile data sets. In this context, data access may be via a computer network.

The above described data storage on a computer may provide the information in a form that can be accessed by a user. Accordingly, the user may load the information onto a second access site including downloading the information. However, access may be restricted to users having a password or other security device so as to protect the medical records contained within. A feature of this embodiment of the invention is the ability of a user to add new or annotated records to the data set so the records become part of the biological information.

The graphical representation of calibrated profile data sets pertaining to a product such as a drug provides an opportunity for standardizing a product by means of the calibrated profile, more particularly a signature profile. The profile may be used as a feature with which to demonstrate relative efficacy, differences in mechanisms of actions, etc. compared to other drugs approved for similar or different uses.

The various embodiments of the invention may be also implemented as a computer program product for use with a computer system. The product may include program code for deriving a first profile data set and for producing calibrated profiles. Such implementation may include a series of computer instructions fixed either on a tangible medium, such as a computer readable medium (for example, a diskette, CD-ROM, ROM, or fixed disk), or transmittable to a computer system via a modem or other interface device, such as a communications adapter coupled to a network. The network coupling may be for example, over optical or wired communications lines or via wireless techniques (for example, microwave, infrared or other transmission techniques) or some combination of these. The series of computer instructions preferably embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (for example, shrink wrapped software), preloaded with a computer system (for example, on system ROM or fixed disk), or distributed from a server or electronic bulletin board over a network (for example, the Internet or World Wide Web). In addition, a computer system is further provided including derivative modules for deriving a first data set and a calibration profile data set.

The calibration profile data sets in graphical or tabular form, the associated databases, and the calculated index or derived algorithm, together with information extracted from the panels, the databases, the data sets or the indices or algorithms are commodities that can be sold together or separately for a variety of purposes as described in WO 01/25473.

Index Construction

In combination, (i) the remarkable consistency of Gene Expression Profiles with respect to a biological condition across a population and (ii) the use of procedures that provide substantially reproducible measurement of constituents in a Gene Expression Panel giving rise to a Gene Expression Profile, under measurement conditions wherein specificity and efficiencies of amplification for all constituents of the panel are substantially similar, make possible the use of an index that characterizes a Gene Expression Profile, and which therefore provides a measurement of a biological condition.

An index may be constructed using an index function that maps values in a Gene Expression Profile into a single value that is pertinent to the biological condition at hand. The values in a Gene Expression Profile are the amounts of each constituent of the Gene Expression Panel that corresponds to the Gene Expression Profile. These constituent amounts form a profile data set, and the index function generates a single value—the index—from the members of the profile data set.

The index function may conveniently be constructed as a linear sum of terms, each term being what we call a "contribution function" of a member of the profile data set. For example, the contribution function may be a constant times a power of a member of the profile data set. So the index function would have the form $$I = \Sigma C_i M_i^{P(i)},$$

where I is the index, $M_i$ is the value of the member i of the profile data set, $C_i$ is a constant, and P(i) is a power to which $M_i$ is raised, the sum being formed for all integral values of i up to the number of members in the data set. We thus have a linear polynomial expression.

The values $C_i$ and P(i) may be determined in a number of ways, so that the index I is informative of the pertinent biological condition. One way is to apply statistical techniques, such as latent class modeling, to the profile data sets to correlate clinical data or experimentally derived data, or other data pertinent to the biological condition. In this connection, for example, may be employed the software from Statistical Innovations, Belmont, Mass., called Latent Gold®. See the web pages at statisticalinnovations.com/lg/, which are hereby incorporated herein by reference.

Alternatively, other simpler modeling techniques may be employed in a manner known in the art. The index function for inflammation may be constructed, for example, in a manner that a greater degree of inflammation (as determined by the a profile data set for the Inflammation Gene Expression Profile) correlates with a large value of the index function. In a simple embodiment, therefore, each P(i) may be +1 or −1, depending on whether the constituent increases or decreases with increasing inflammation. As discussed in further detail below, we have constructed a meaningful inflammation index that is proportional to the expression $$\tfrac{1}{4}\{IL1A\}+\tfrac{1}{4}\{IL1B\}+\tfrac{1}{4}\{TNF\}+\tfrac{1}{4}\{INFG\}-1/\{IL10\},$$

where the braces around a constituent designate measurement of such constituent and the constituents are a subset of the Inflammation Gene Expression Panel of Table 1.

Just as a baseline profile data set, discussed above, can be used to provide an appropriate normative reference, and can even be used to create a Calibrated profile data set, as discussed above, based on the normative reference, an index that characterizes a Gene Expression Profile can also be provided with a normative value of the index function used to create the index. This normative value can be determined with respect to a relevant population, so that the index may be interpreted in relation to the normative value. The relevant population may have in common a property that is at least one of age group, gender, ethnicity, geographic location, diet, medical disorder, clinical indicator, medication, physical activity, body mass, and environmental exposure.

As an example, the index can be constructed, in relation to a normative Gene Expression Profile for a population of healthy subjects, in such a way that a reading of approximately 1 characterizes normative Gene Expression Profiles of healthy subjects. Let us further assume that the biological condition that is the subject of the index is inflammation; a reading of 1 in this example thus corresponds to a Gene Expression Profile that matches the norm for healthy subjects. A substantially higher reading then may identify a subject experiencing an inflammatory condition. The use of 1 as identifying a normative value, however, is only one possible choice; another logical choice is to use 0 as identifying the normative value. With this choice, deviations in the index from zero can be indicated in standard deviation units (so that values lying between −1 and +1 encompass 90% of a normally distributed reference population. Since we have found that Gene Expression Profile values (and accordingly constructed indices based on them) tend to be normally distributed, the 0-centered index constructed in this manner is highly informative. It therefore facilitates use of the index in diagnosis of disease and setting objectives for treatment. The choice of 0 for the normative value, and the use of standard deviation units, for example, are illustrated in FIG. 17B, discussed below.

EXAMPLES

Example 1

Acute inflammatory index to assist in analysis of large, complex data sets.

In one embodiment of the invention the index value or algorithm can be used to reduce a complex data set to a single index value that is informative with respect to the inflammatory state of a subject. This is illustrated in FIGS. 1A and 1B.

Figure 1A:
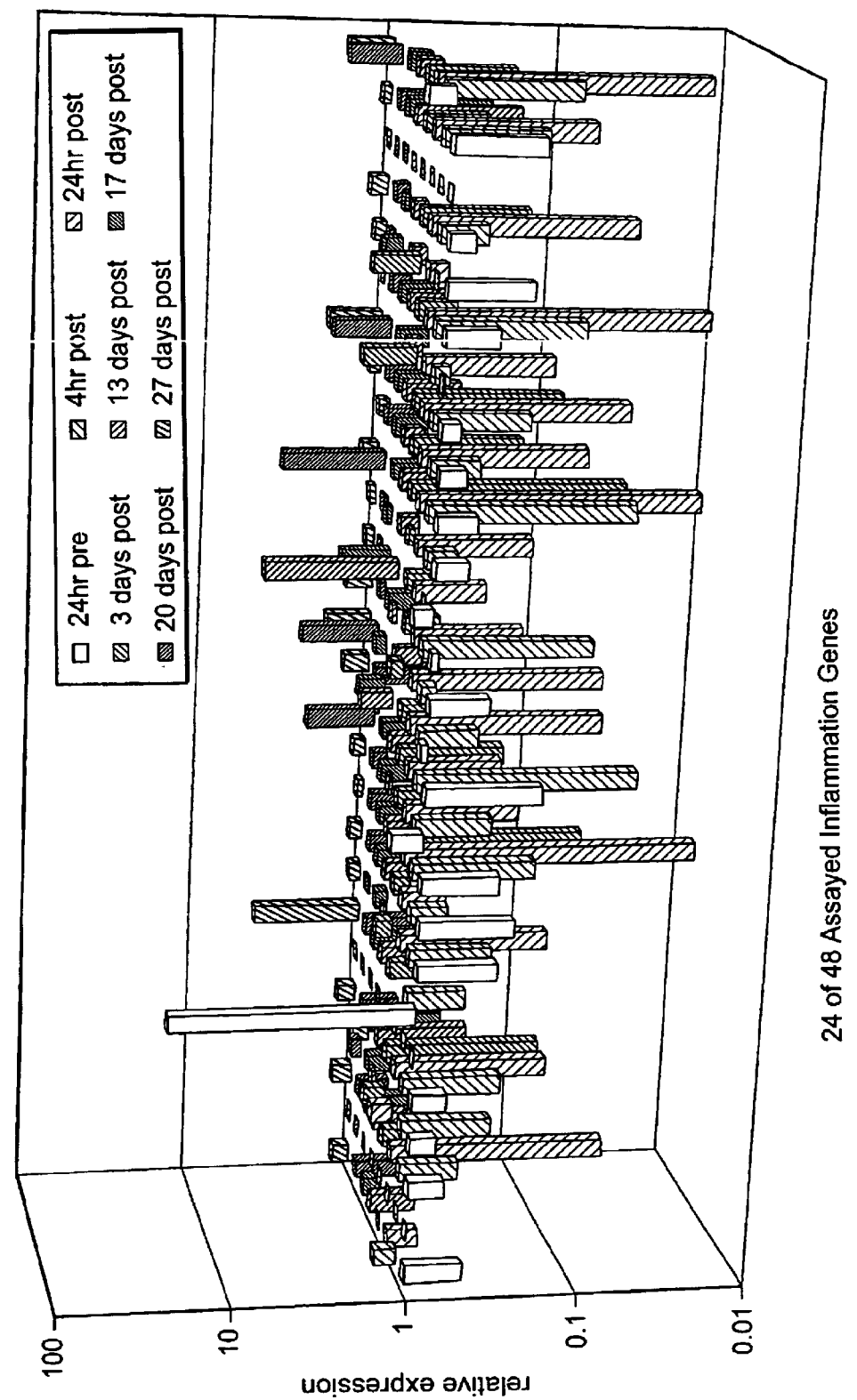
FIG. 1A shows the results of assaying 24 genes from the Source Inflammation Gene Panel (shown in Table 1) on eight separate days during the course of optic neuritis in a single male subject.

FIG. 1A is entitled Source Precision Inflammation Profile Tracking of A Subject Results in a Large, Complex Data Set. The figure shows the results of assaying 24 genes from the Inflammation Gene Expression Panel (shown in Table 1) on eight separate days during the course of optic neuritis in a single male subject.

FIG. 1B shows use of an Acute Inflammation Index. The data displayed in FIG. 1A above is shown in this figure after calculation using an index function proportional to the following mathematical expression: ($\tfrac{1}{4}\{IL1A\}+\tfrac{1}{4}\{IL1B\}+\tfrac{1}{4}\{TNF\}+\tfrac{1}{4}\{INFG\}-1/\{IL10\}$).

Example 2

Use of acute inflammation index or algorithm to monitor a biological condition of a sample or a subject. The inflammatory state of a subject reveals information about the past progress of the biological condition, future progress, response to treatment, etc. The Acute Inflammation Index may be used to reveal such information about the biological condition of a subject. This is illustrated in FIG. 2.

The results of the assay for inflammatory gene expression for each day (shown for 24 genes in each row of FIG. 1A) is displayed as an individual histogram after calculation. The index reveals clear trends in inflammatory status that may correlated with therapeutic intervention (FIG. 2).

Figure 2:
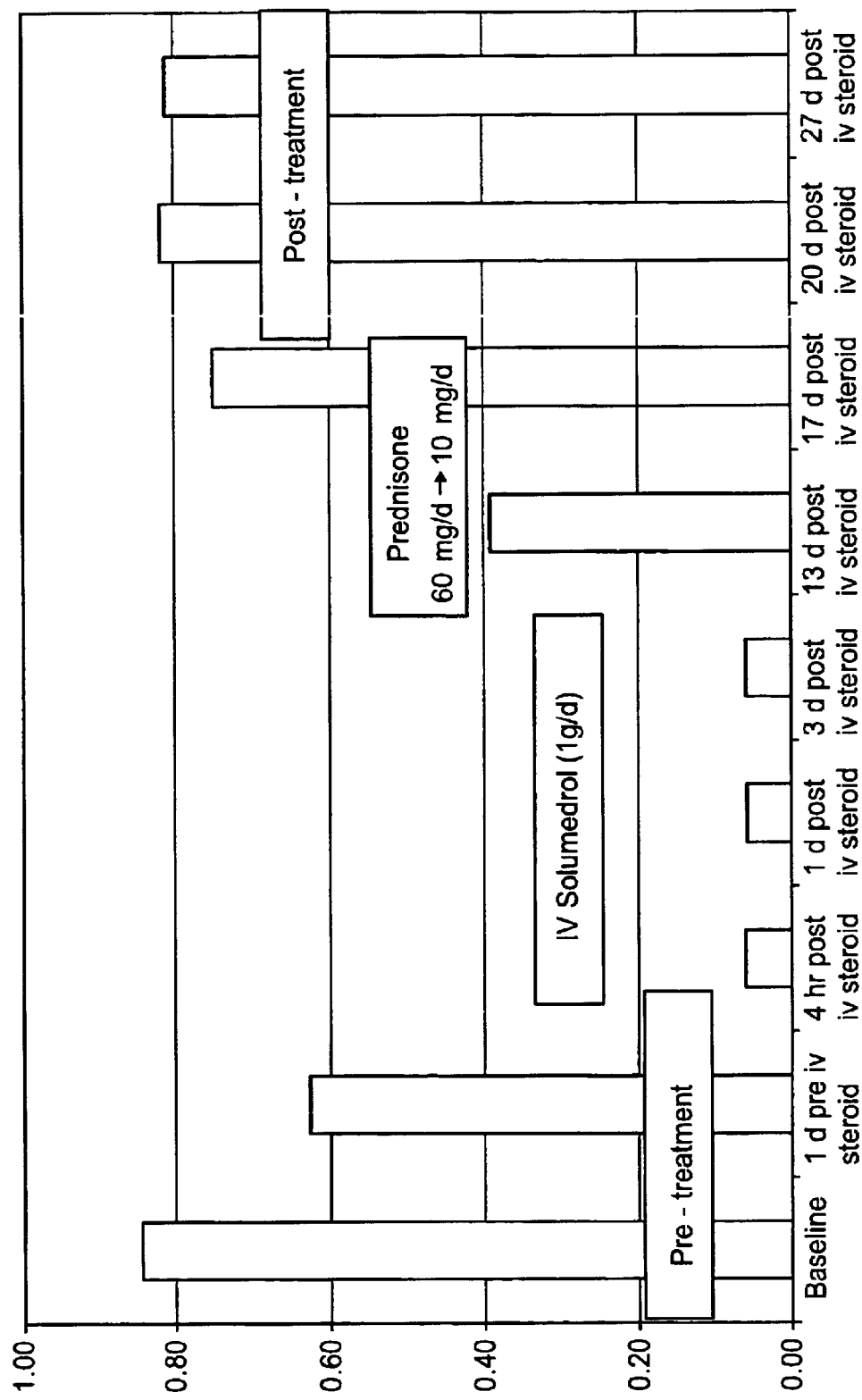
FIG. 2 is a graphical illustration of the same inflammation index calculated at 9 different, significant clinical milestones.

FIG. 2 is a graphical illustration of the acute inflammation index calculated at 9 different, significant clinical milestones from blood obtained from a single patient treated medically with for optic neuritis. Changes in the index values for the Acute Inflammation Index correlate strongly with the expected effects of therapeutic intervention. Four clinical milestones have been identified on top of the Acute Inflammation Index in this figure including (1) prior to treatment with steroids, (2) treatment with IV solumedrol at 1 gram per day, (3) post-treatment with oral prednisone at 60 mg per day tapered to 10 mg per day and (4) post treatment. The data set is the same as for FIG. 1. The index is proportional to $1/4\{IL1A\}+1/4\{IL1B\}+1/4\{TNF\}+1/4\{INFG\}-1/\{IL10\}$. As expected, the acute inflammation index falls rapidly with treatment with IV steroid, goes up during less efficacious treatment with oral prednisone and returns to the pre-treatment level after the steroids have been discontinued and metabolized completely.

Example 3

Figure 3:
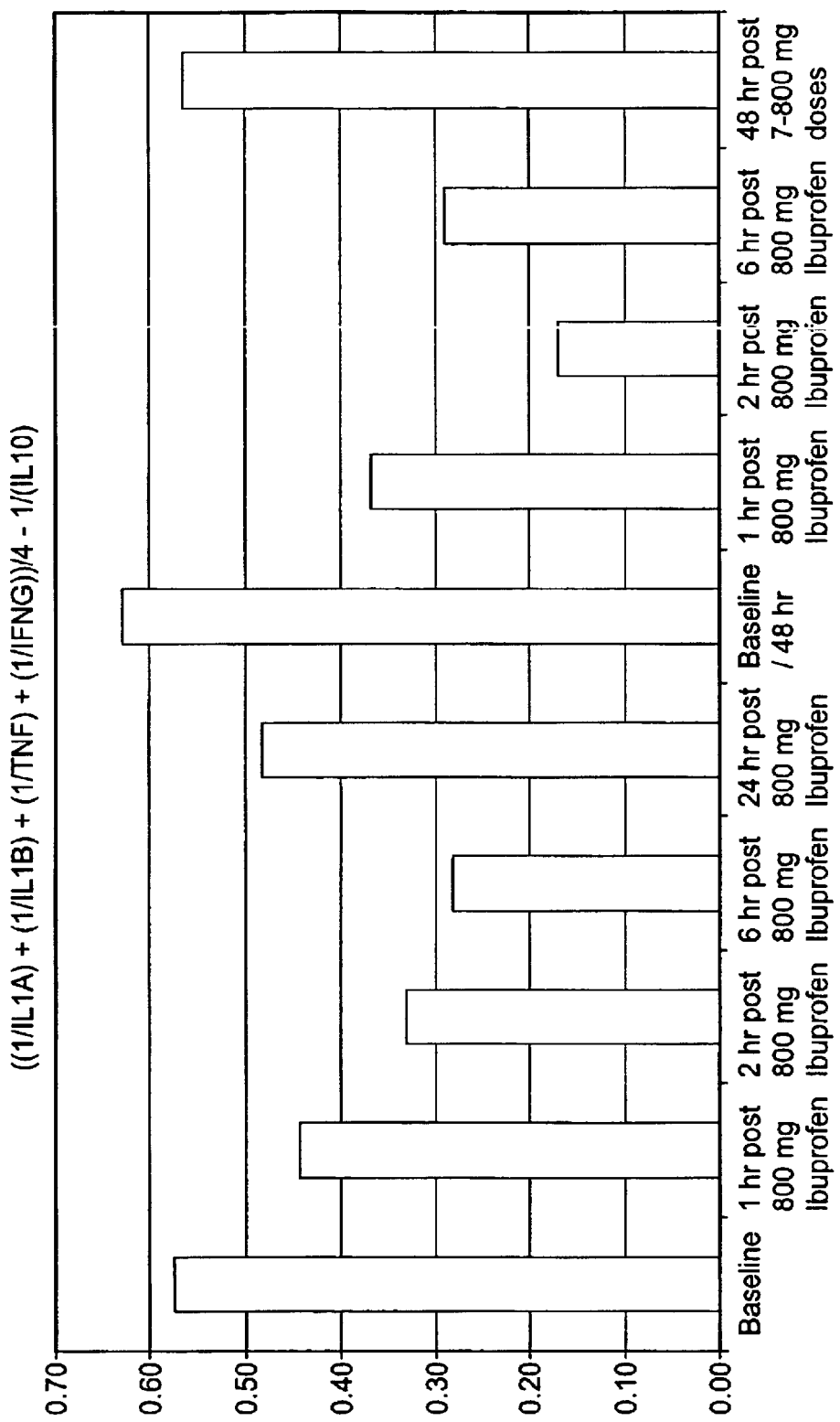
FIG. 3 shows the effects of single dose treatment with 800 mg of ibuprofen in a single donor as characterized by the index.

Use of the acute inflammatory index to set dose, including concentrations and timing, for compounds in development or for compounds to be tested in human and non-human subjects as shown in FIG. 3. The acute inflammation index may be used as a common reference value for therapeutic compounds or interventions without common mechanisms of action. The compound that induces a gene response to a compound as indicated by the index, but fails to ameliorate a known biological conditions may be compared to a different compounds with varying effectiveness in treating the biological condition.

FIG. 3 shows the effects of single dose treatment with 800 mg of ibuprofen in a single donor as characterized by the Acute Inflammation Index. 800 mg of over-the-counter ibuprofen were taken by a single subject at Time=0 and Time=48 hr. Gene expression values for the indicated five inflammation-related gene loci were determined as described below at times=2, 4, 6, 48, 50, 56 and 96 hours. As expected the acute inflammation index falls immediately after taking the non-steroidal anti-inflammatory ibuprofen and returns to baseline after 48 hours. A second dose at T=48 follows the same kinetics at the first dose and returns to baseline at the end of the experiment at T=96.

Example 4

Use of the acute inflammation index to characterize efficacy, safety, and mode of physiological action for an agent, which may be in development and/or may be complex in nature. This is illustrated in FIG. 4.

Figure 4:
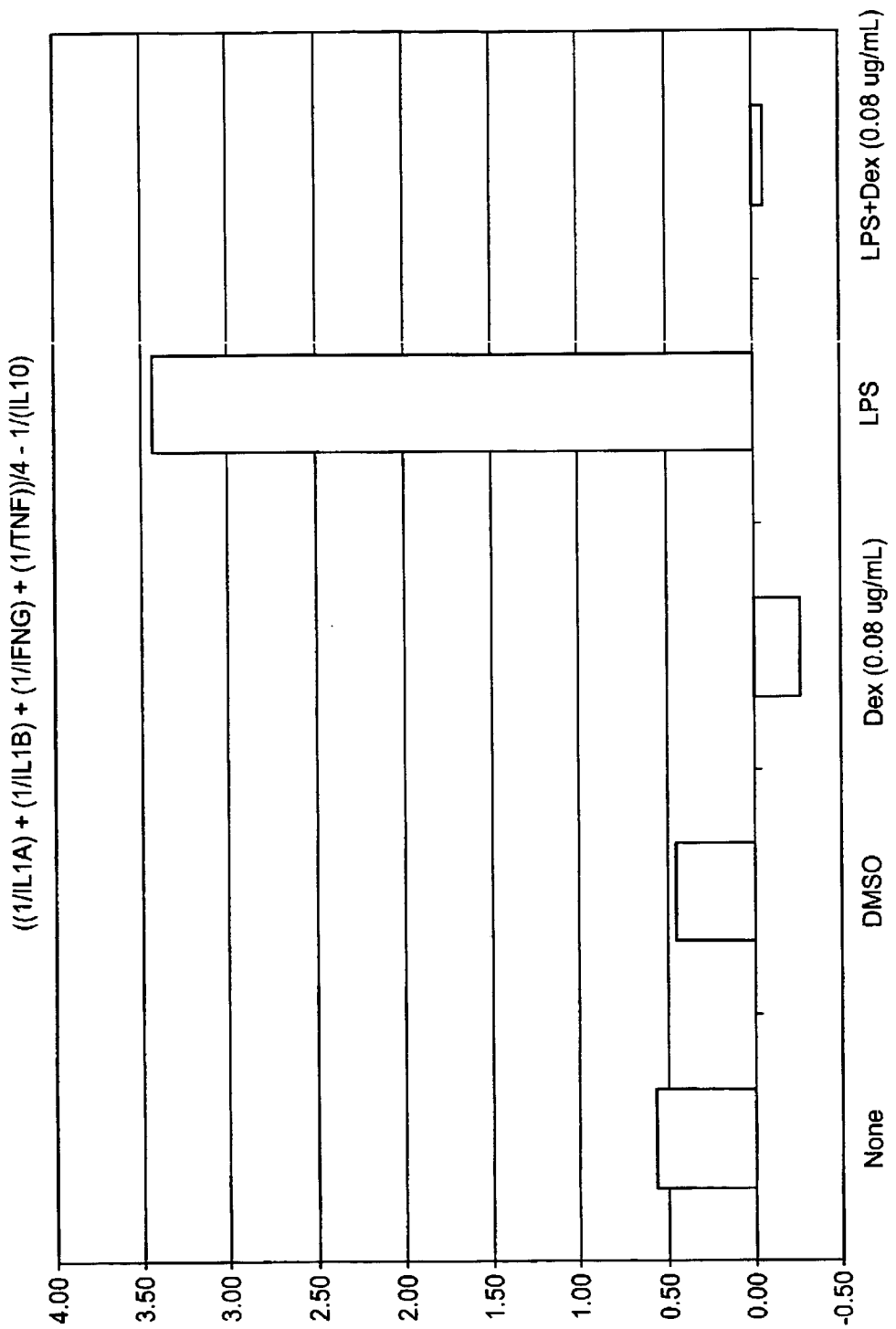
FIG. 4 shows the calculated acute inflammation index displayed graphically for five different conditions.

FIG. 4 shows that the calculated acute inflammation index displayed graphically for five different conditions including (A) untreated whole blood; (B) whole blood treated in vitro with DMSO, an non-active carrier compound; (C) otherwise unstimulated whole blood treated in vitro with dexamethasone (0.08 ug/ml); (D) whole blood stimulated in vitro with lipopolysaccharide, a known pro-inflammatory compound, (LPS, 1 ng/ml) and (E) whole blood treated in vitro with LPS (1 ng/ml) and dexamethasone (0.08 ug/ml). Dexamethasone is used as a prescription compound that is commonly used medically as an anti-inflammatory steroid compound. The acute inflammation index is calculated from the experimentally determined gene expression levels of inflammation-related genes expressed in human whole blood obtained from a single patient. Results of mRNA expression are expressed as Ct's in this example, but may be expressed as, e.g., relative fluorescence units, copy number or any other quantifiable, precise and calibrated form, for the genes IL1A, IL1B, TNF, IFNG and IL10. From the gene expression values, the acute inflammation values were determined algebraically according in proportion to the expression $\frac{1}{4}\{IL1A\}+\frac{1}{4}\{IL1B\}+\frac{1}{4}\{TNF\}+\frac{1}{4}\{INFG\}-1/\{IL10\}$.

Example 5

Figure 6:
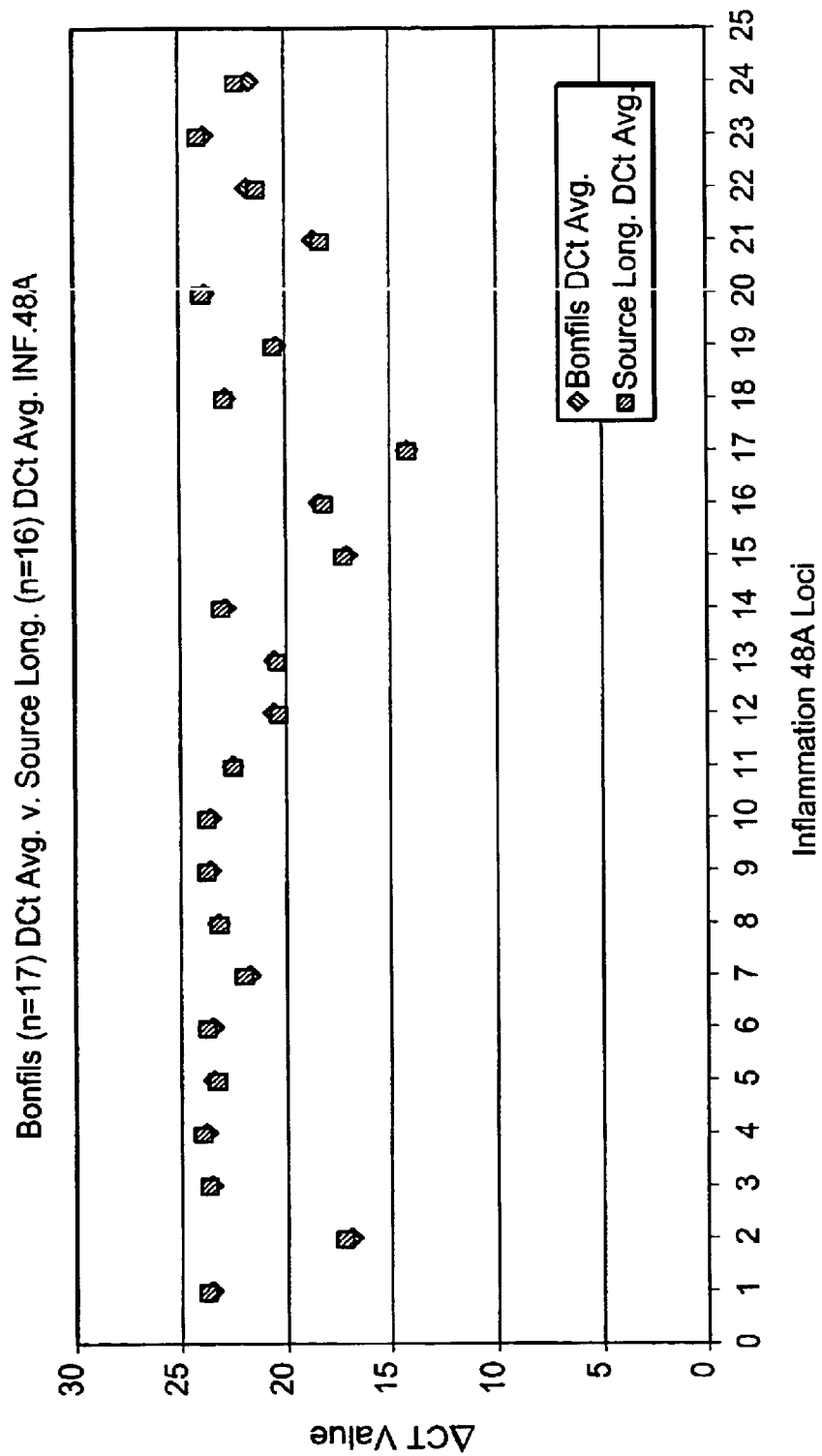
FIGS. 6 and 7 compare two different populations using Gene Expression Profiles (with respect to the 48 loci of the Inflammation Gene Expression Panel of Table 1).
Figure 7:
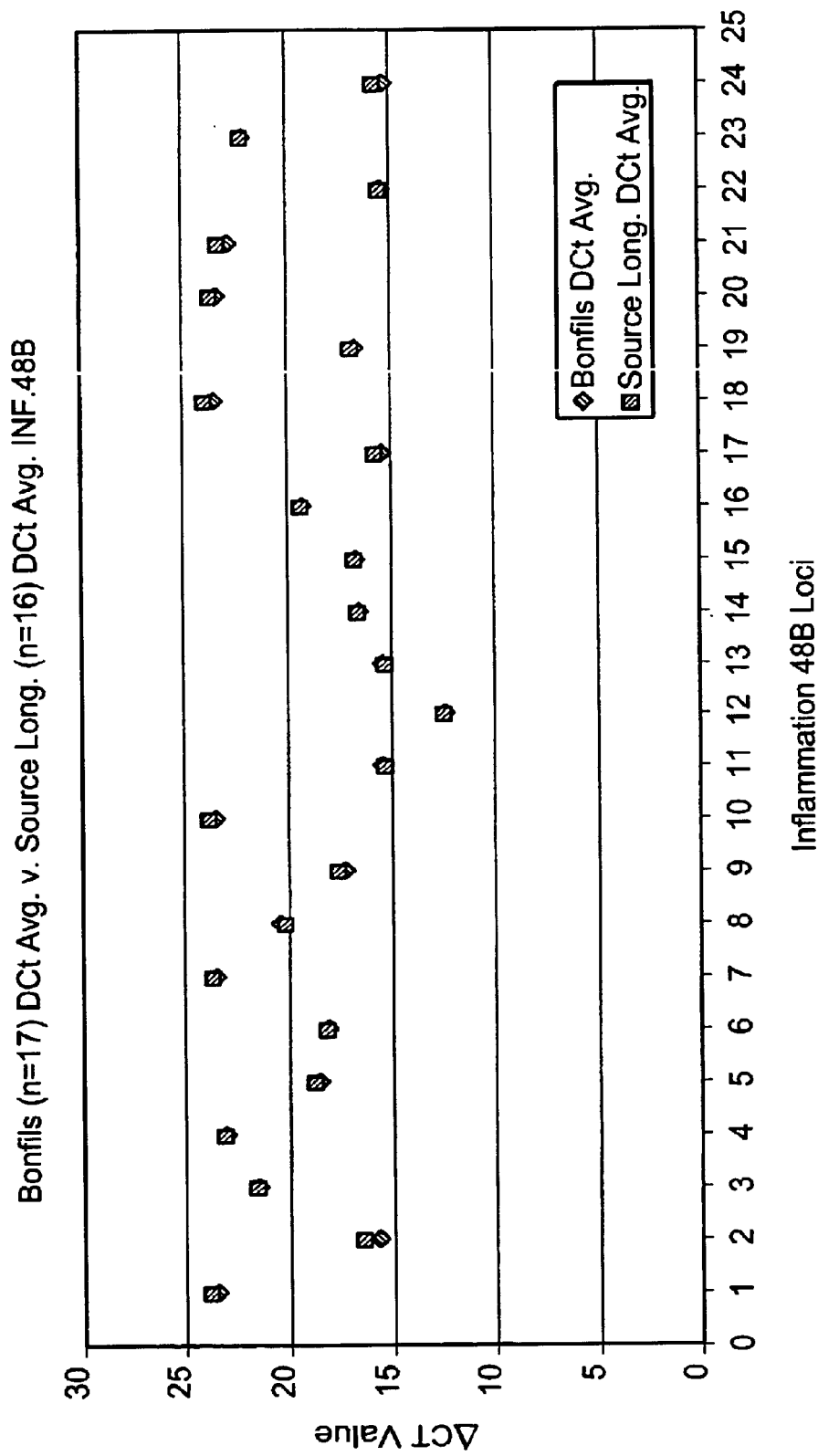

Development and use of population normative values for gene expression profiles. FIGS. 6 and 7 show the arithmetic mean values for gene expression profiles (using the 48 loci of the Inflammation Gene Expression Panel of Table 1) obtained from whole blood of two distinct patient populations. These populations are both normal or undiagnosed. The first population, which is identified as Bonfils (the plot points for which are represented by diamonds), is composed of 17 subjects accepted as blood donors at the Bonfils Blood Center in Denver, Colo. The second population is 9 donors, for which Gene Expression Profiles were obtained from assays conducted four times over a four-week period. Subjects in this second population (plot points for which are represented by squares) were recruited from employees of Source Precision Medicine, Inc., the assignee herein. Gene expression averages for each population were calculated for each of 48 gene loci of the Gene Expression Inflammation Panel. The results for loci 1–24 (sometimes referred to below as the Inflammation 48A loci) are shown in FIG. 6 and for loci 25–48 (sometimes referred to below as the Inflammation 48B loci) are shown in FIG. 7.

The consistency between gene expression levels of the two distinct populations is dramatic. Both populations show gene expressions for each of the 48 loci that are not significantly different from each other. This observation suggests that there is a "normal" expression pattern for human inflammatory genes, that a Gene Expression Profile, using the Inflammation Gene Expression Panel of Table 1 (or a subset thereof) characterizes that expression pattern, and that a population-normal expression pattern can be used, for example, to guide medical intervention for any biological condition that results in a change from the normal expression pattern.

In a similar vein, FIG. 8 shows arithmetic mean values for gene expression profiles (again using the 48 loci of the Inflammation Gene Expression Panel of Table 1) also obtained from whole blood of two distinct patient populations. One population, expression values for which are represented by triangular data points, is 24 normal, undiagnosed subjects (who therefore have no known inflammatory disease). The other population, the expression values for which are represented by diamond-shaped data points, is four patients with rheumatoid arthritis and who have failed therapy (who therefore have unstable rheumatoid arthritis).

As remarkable as the consistency of data from the two distinct normal populations shown in FIGS. 6 and 7 is the systematic divergence of data from the normal and diseased populations shown in FIG. 8. In 45 of the shown 48 inflammatory gene loci, subjects with unstable rheumatoid arthritis showed, on average, increased inflammatory gene expression (lower cycle threshold values; Ct), than subjects without disease. The data thus further demonstrate that is possible to identify groups with specific biological conditions using gene expression if the precision and calibration of the underlying assay are carefully designed and controlled according to the teachings herein.

Figure 9:
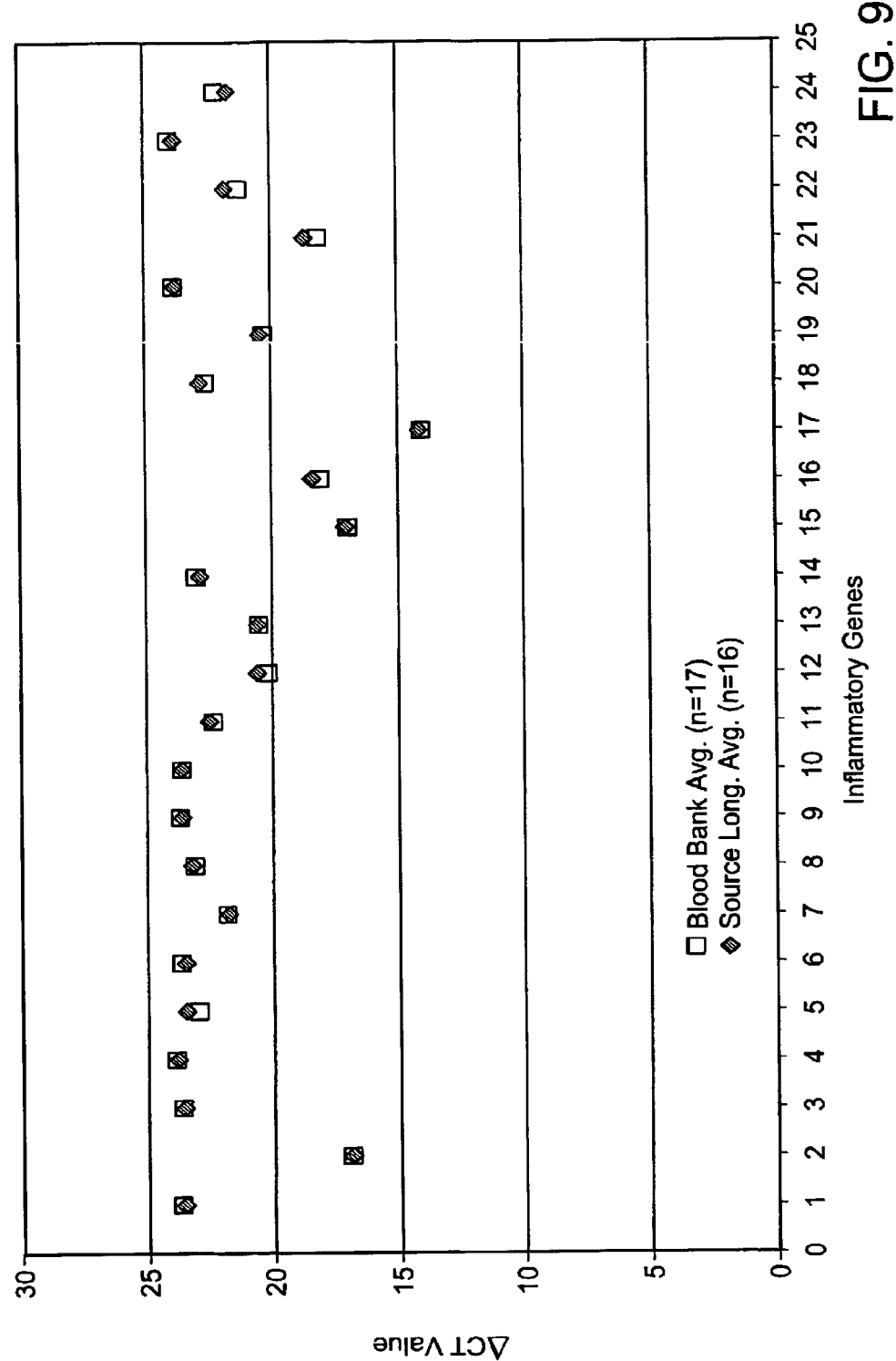
FIG. 9 compares two normal populations, one longitudinal and the other cross sectional.

FIG. 9, in a manner analogous to FIG. 8, shows the shows arithmetic mean values for gene expression profiles using 24 loci of the Inflammation Gene Expression Panel of Table 1) also obtained from whole blood of two distinct patient populations. One population, expression values for which are represented by diamond-shaped data points, is 17 normal, undiagnosed subjects (who therefore have no known inflammatory disease) who are blood donors. The other population, the expression values for which are represented by square-shaped data points, is 16 subjects, also normal and undiagnosed, who have been monitored over six months, and the averages of these expression values are represented by the square-shaped data points. Thus the cross-sectional gene expression-value averages of a first healthy population match closely the longitudinal gene expression-value averages of a second healthy population., with approximately 7% or less variation in measured expression value on a gene-to-gene basis.

Figure 10:
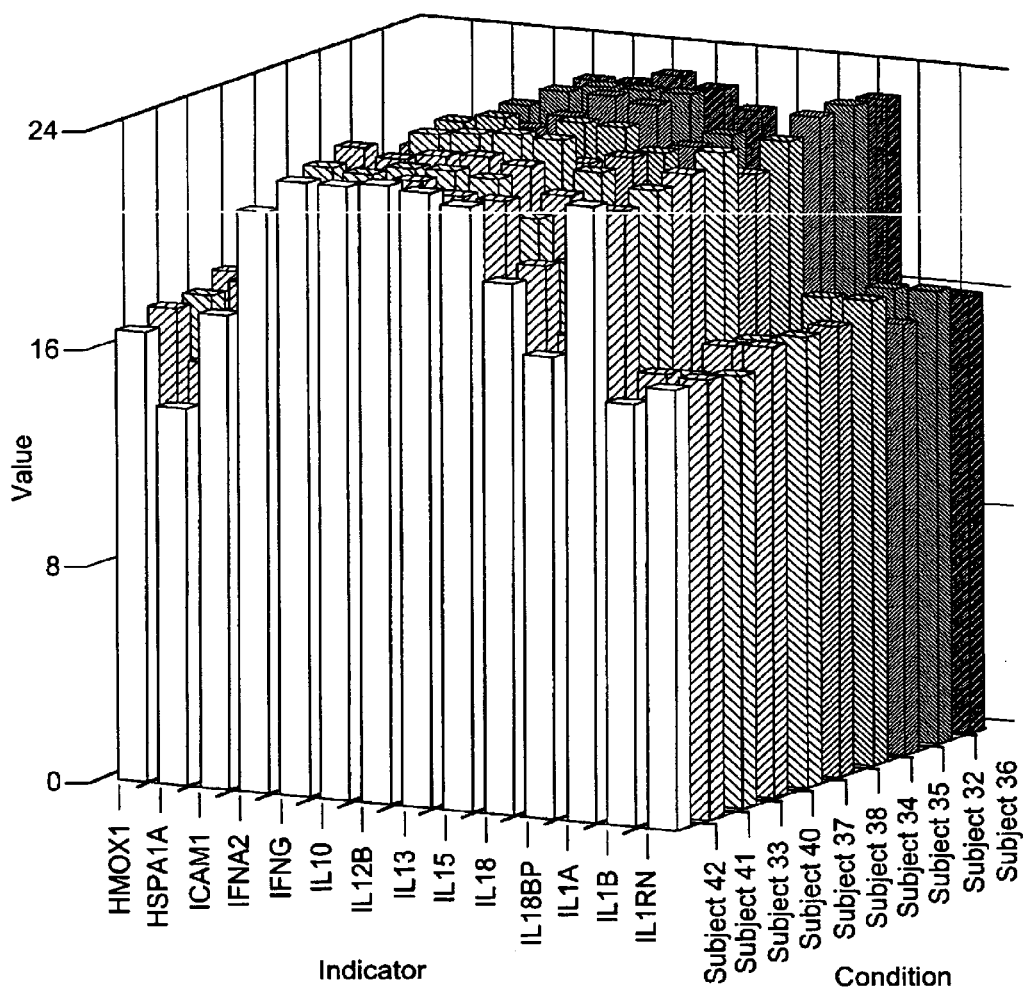
FIG. 10 shows the shows gene expression values for various individuals of a normal population.

FIG. 10 shows the shows gene expression values (using 14 loci of the Inflammation Gene Expression Panel of Table 1) obtained from whole blood of 44 normal undiagnosed blood donors (data for 10 subjects of which is shown). Again, the gene expression values for each member of the population are closely matched to those for the population, represented visually by the consistent peak heights for each of the gene loci. Other subjects of the population and other gene loci than those depicted here display results that are consistent with those shown here.

In consequence of these principles, and in various embodiments of the present invention, population normative values for a Gene Expression Profile can be used in comparative assessment of individual subjects as to biological condition, including both for purposes of health and/or disease. In one embodiment the normative values for a Gene Expression Profile may be used as a baseline in computing a "calibrated profile data set" (as defined at the beginning of this section) for a subject that reveals the deviation of such subject's gene expression from population normative values. Population normative values for a Gene Expression Profile can also be used as baseline values in constructing index functions in accordance with embodiments of the present invention. As a result, for example, an index function can be constructed to reveal not only the extent of an individual's inflammation expression generally but also in relation to normative values.

Example 6

Figure 11:
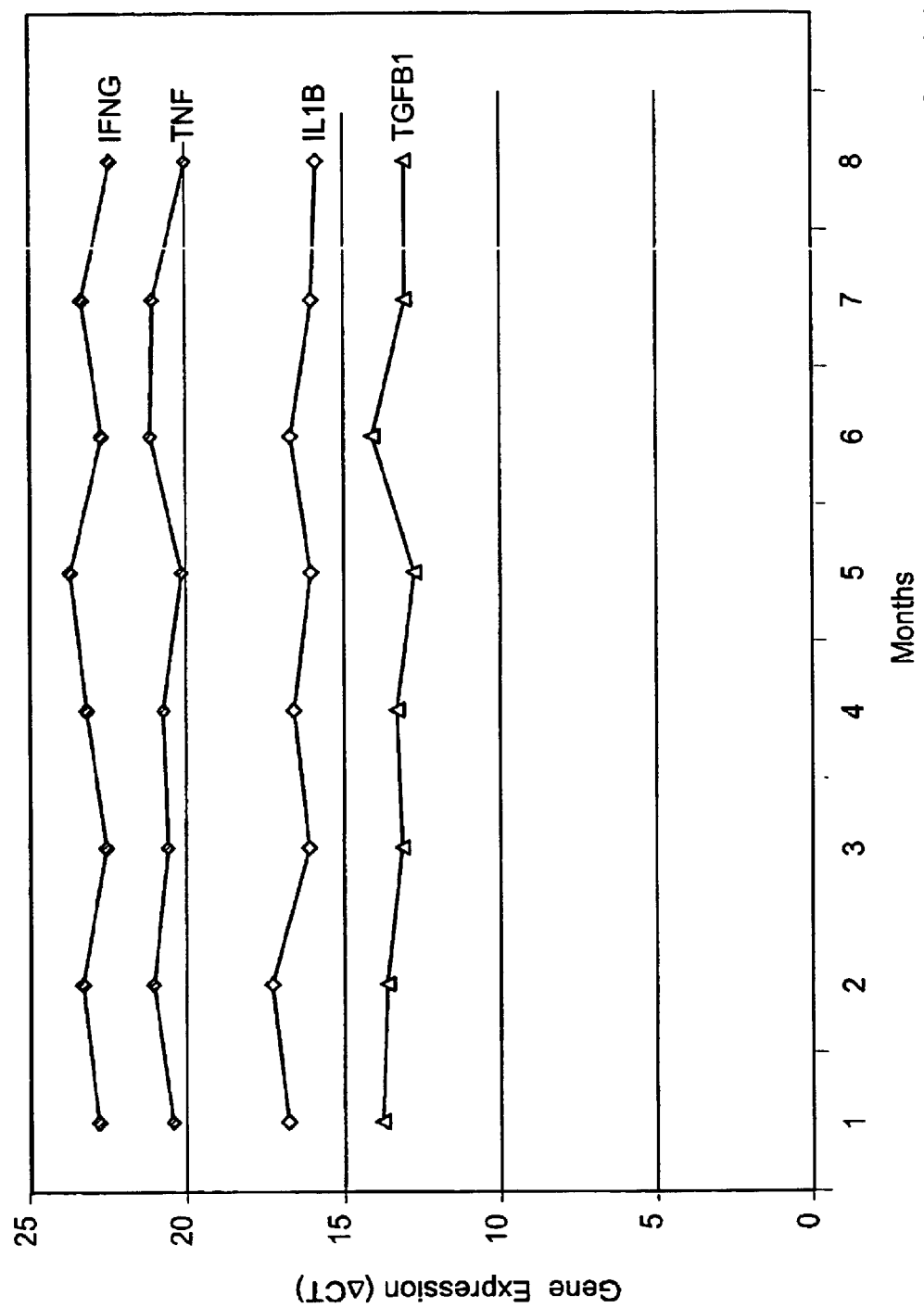
FIG. 11 shows the expression levels for each of four genes (of the Inflammation Gene Expression Panel of Table 1), of a single subject, assayed monthly over a period of eight months.

Consistency of expression values, of constituents in Gene Expression Panels, over time as reliable indicators of biological condition. FIG. 11 shows the expression levels for each of four genes (of the Inflammation Gene Expression Panel of Table 1), of a single subject, assayed monthly over a period of eight months. It can be seen that the expression levels are remarkably consistent over time.

Figure 12:
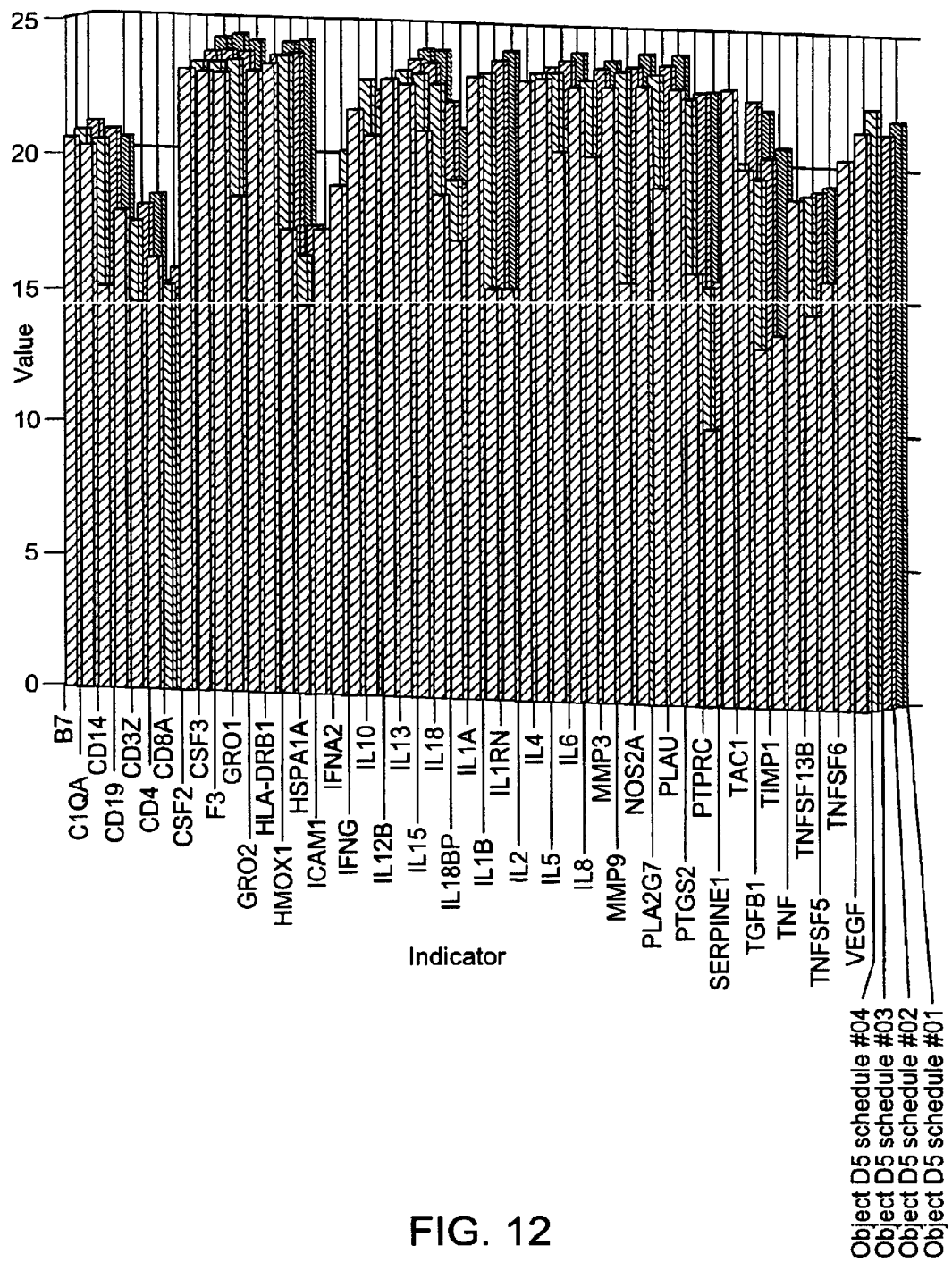
FIGS. 12 and 13 similarly show in each case the expression levels for each of 48 genes (of the Inflammation Gene Expression Panel of Table 1), of distinct single subjects (selected in each case on the basis of feeling well and not taking drugs), assayed, in the case of FIG. 12 weekly over a period of four weeks, and in the case of FIG. 13 monthly over a period of six months.
Figure 13:
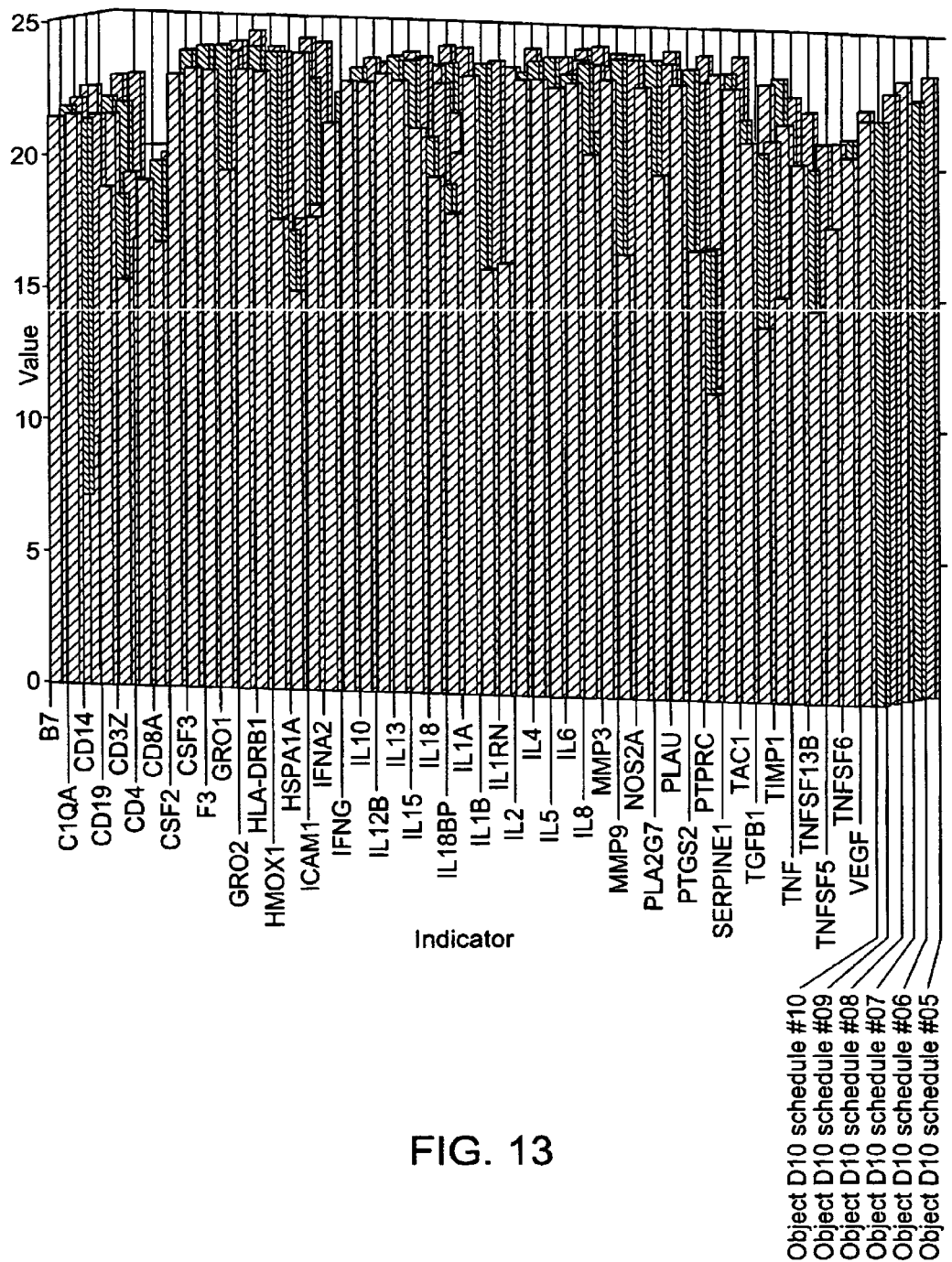

FIGS. 12 and 13 similarly show in each case the expression levels for each of 48 genes (of the Inflammation Gene Expression Panel of Table 1), of distinct single subjects (selected in each case on the basis of feeling well and not taking drugs), assayed, in the case of FIG. 12 weekly over a period of four weeks, and in the case of FIG. 13 monthly over a period of six months. In each case, again the expression levels are remarkably consistent over time, and also similar across individuals.

Figure 14:
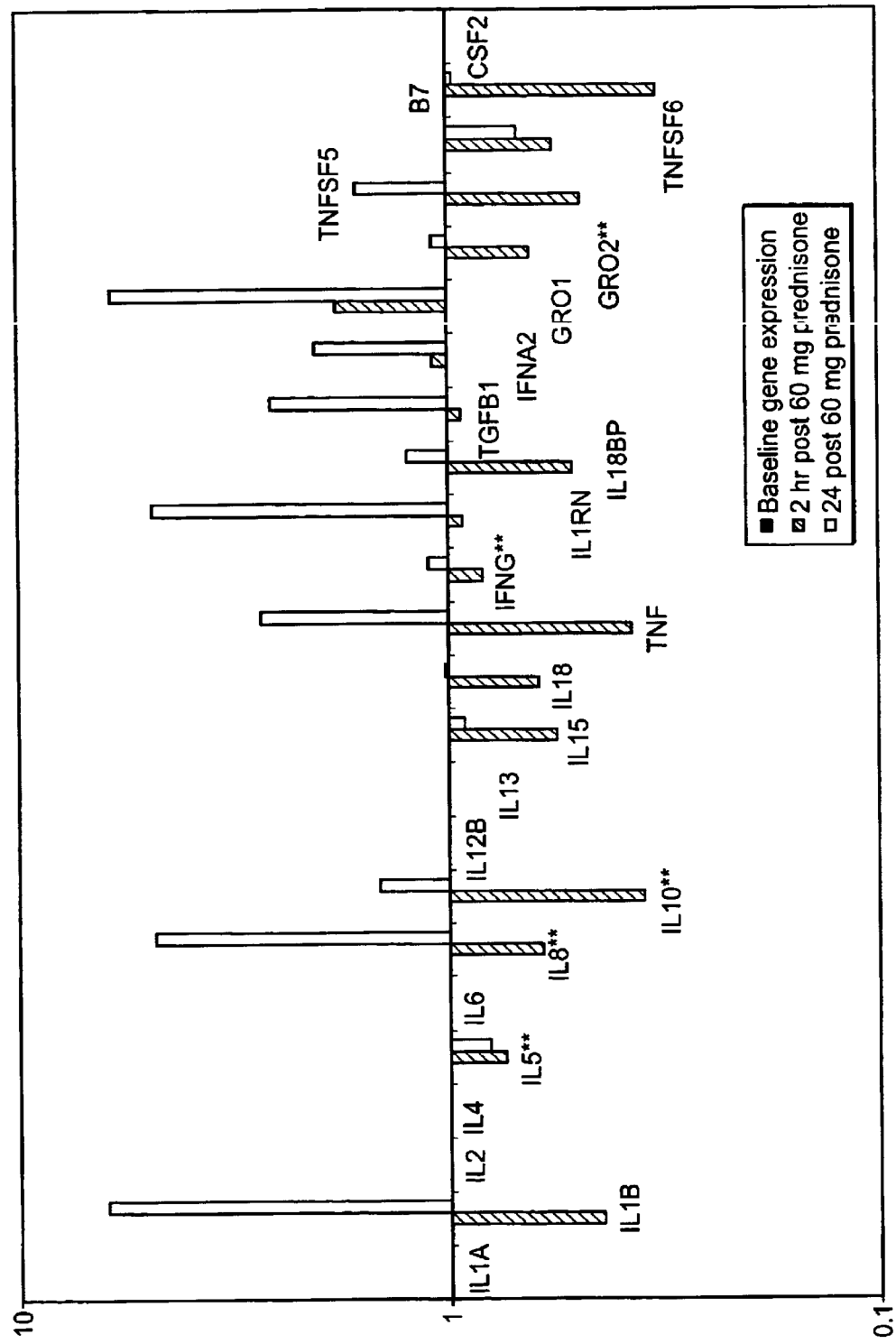
FIG. 14 shows the effect over time, on inflammatory gene expression in a single human subject., of the administration of an anti-inflammatory steroid, as assayed using the Inflammation Gene Expression Panel of Table 1.

FIG. 14 also shows the effect over time, on inflammatory gene expression in a single human subject, of the administration of an anti-inflammatory steroid, as assayed using the Inflammation Gene Expression Panel of Table 1. In this case, 24 of 48 loci are displayed. The subject had a baseline blood sample drawn in a PAX RNA isolation tube and then took a single 60 mg dose of prednisone, an anti-inflammatory, prescription steroid. Additional blood samples were drawn at 2 hr and 24 hr post the single oral dose. Results for gene expression are displayed for all three time points, wherein values for the baseline sample are shown as unity on the x-axis. As expected, oral treatment with prednisone resulted in the decreased expression of most of inflammation-related gene loci, as shown by the 2-hour post-administration bar graphs. However, the 24-hour post-administration bar graphs show that, for most of the gene loci having reduced gene expression at 2 hours, there were elevated gene expression levels at 24 hr.

Although the baseline in FIG. 14 is based on the gene expression values before drug intervention associated with the single individual tested, we know from the previous example, that healthy individuals tend toward population normative values in a Gene Expression Profile using the Inflammation Gene Expression Panel of Table 1 (or a subset of it). We conclude from FIG. 14 that in an attempt to return the inflammatory gene expression levels to those demonstrated in FIGS. 6 and 7 (normal or set levels), interference with the normal expression induced a compensatory gene expression response that over-compensated for the drug-induced response, perhaps because the prednisone had been significantly metabolized to inactive forms or eliminated from the subject.

Figure 15:
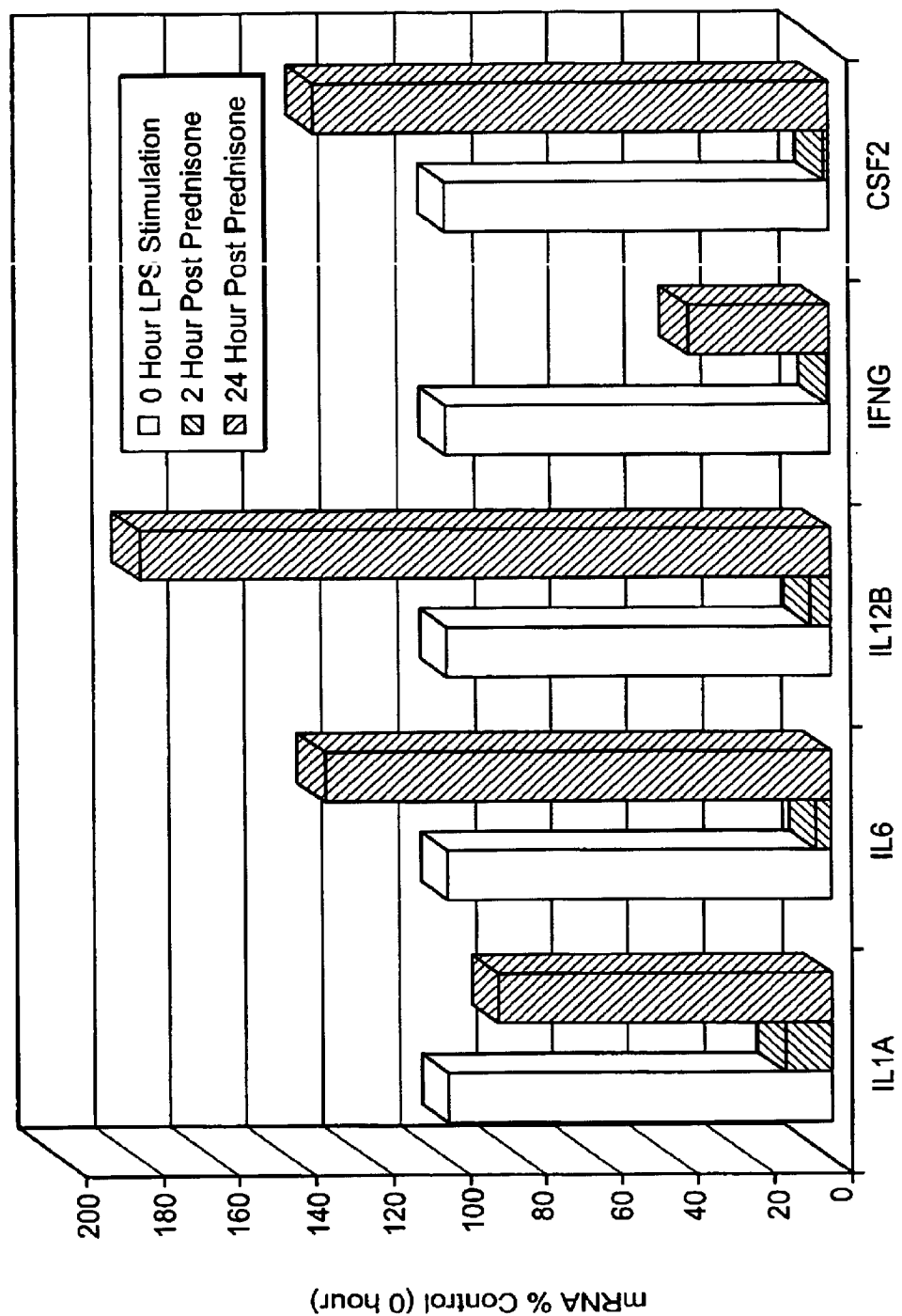
FIG. 15, in a manner analogous to FIG. 14, shows the effect over time, via whole blood samples obtained from a human subject, administered a single dose of prednisone, on expression of 5 genes (of the Inflammation Gene Expression Panel of Table 1).

FIG. 15, in a manner analogous to FIG. 14, shows the effect over time, via whole blood samples obtained from a human subject, administered a single dose of prednisone, on expression of 5 genes (of the Inflammation Gene Expression Panel of Table 1). The samples were taken at the time of administration (t=0) of the prednisone, then at two and 24 hours after such administration. Each whole blood sample was challenged by the addition of 0.1 ng/ml of lipopolysaccharide (a Gram-negative endotoxin) and a gene expression profile of the sample, post-challenge, was determined. It can seen that the two-hour sample shows dramatically reduced gene expression of the 5 loci of the Inflammation Gene Expression Panel, in relation to the expression levels at the time of administration (t=0). At 24 hours post administration, the inhibitory effect of the prednisone is no longer apparent, and at 3 of the 5 loci, gene expression is in fact higher than at t=0, illustrating quantitatively at the molecular level the well-known rebound effect.

Figure 16:
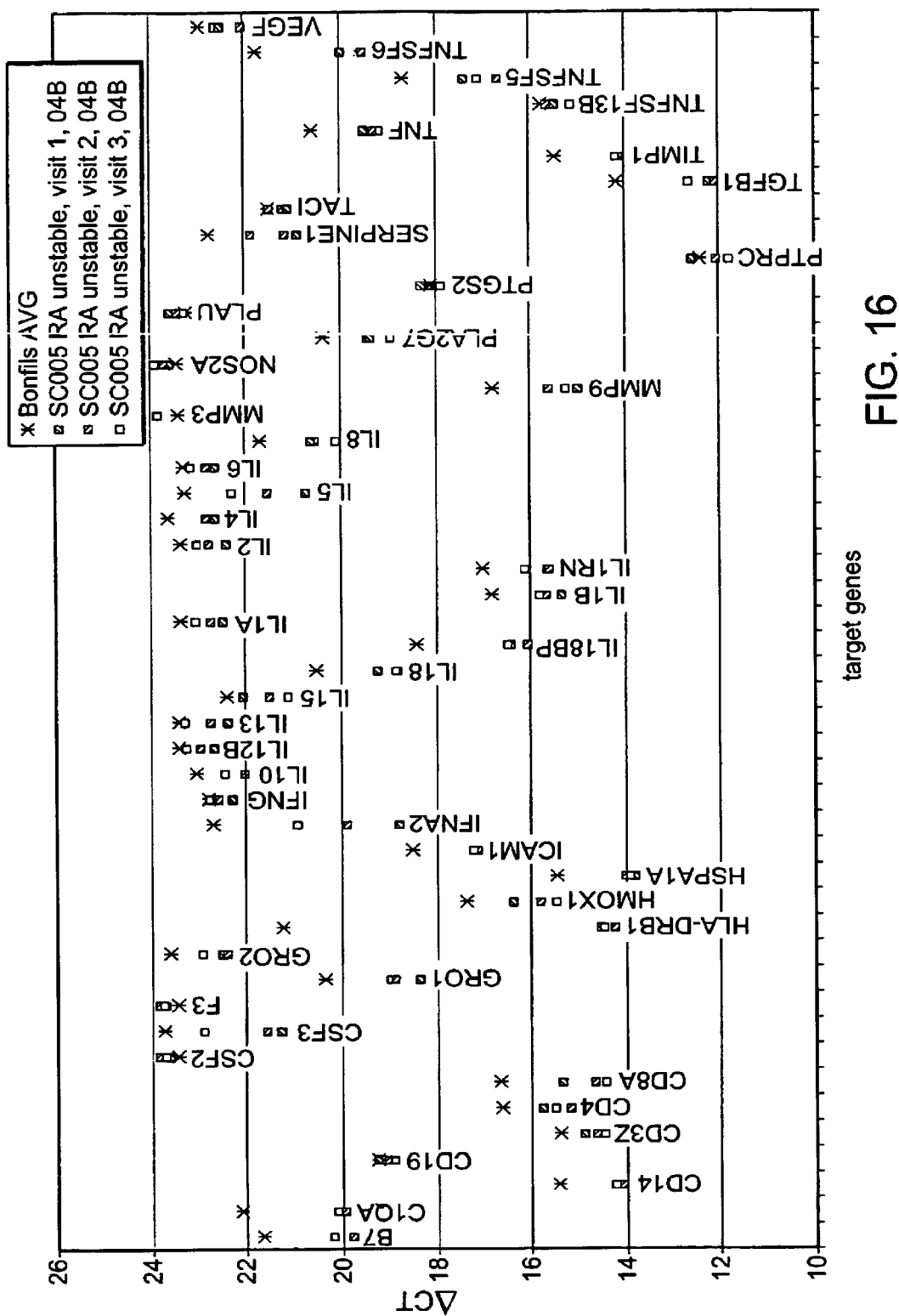
FIG. 16 also shows the effect over time, on inflammatory gene expression in a single human subject suffering from rheumatoid arthritis, of the administration of a TNF-inhibiting compound, but here the expression is shown in comparison to the cognate locus average previously determined (in connection with FIGS. 6 and 7) for the normal (i.e., undiagnosed, healthy) population.

FIG. 16 also shows the effect over time, on inflammatory gene expression in a single human subject suffering from rheumatoid arthritis, of the administration of a TNF-inhibiting compound, but here the expression is shown in comparison to the cognate locus average previously determined (in connection with FIGS. 6 and 7) for the normal (i.e., undiagnosed, healthy) population. As part of a larger international study involving patients with rheumatoid arthritis, the subject was followed over a twelve-week period. The subject was enrolled in the study because of a failure to respond to conservative drug therapy for rheumatoid arthritis and a plan to change therapy and begin immediate treatment with a TNF-inhibiting compound. Blood was drawn from the subject prior to initiation of new therapy (visit 1). After initiation of new therapy, blood was drawn at 4 weeks post change in therapy (visit 2), 8 weeks (visit 3), and 12 weeks (visit 4) following the start of new therapy. Blood was collected in PAX RNA isolation tubes, held at room temperature for two hours and then frozen at −30° C.

Frozen samples were shipped to the central laboratory at Source Precision Medicine, the assignee herein, in Boulder, Colo. for determination of expression levels of genes in the 48-gene Inflammation Gene Expression Panel of Table 1. The blood samples were thawed and RNA extracted according to the manufacturer's recommended procedure. RNA was converted to cDNA and the level of expression of the 48 inflammatory genes was determined. Expression results are shown for 11 of the 48 loci in FIG. 16. When the expression results for the 11 loci are compared from visit one to a population average of normal blood donors from the United States, the subject shows considerable difference. Similarly, gene expression levels at each of the subsequent physician visits for each locus are compared to the same normal average value. Data from visits 2, 3 and 4 document the effect of the change in therapy. In each visit following the change in the therapy, the level of inflammatory gene expression for 10 of the 11 loci is closer to the cognate locus average previously determined for the normal (i.e., undiagnosed, healthy) population.

Figure 17A:
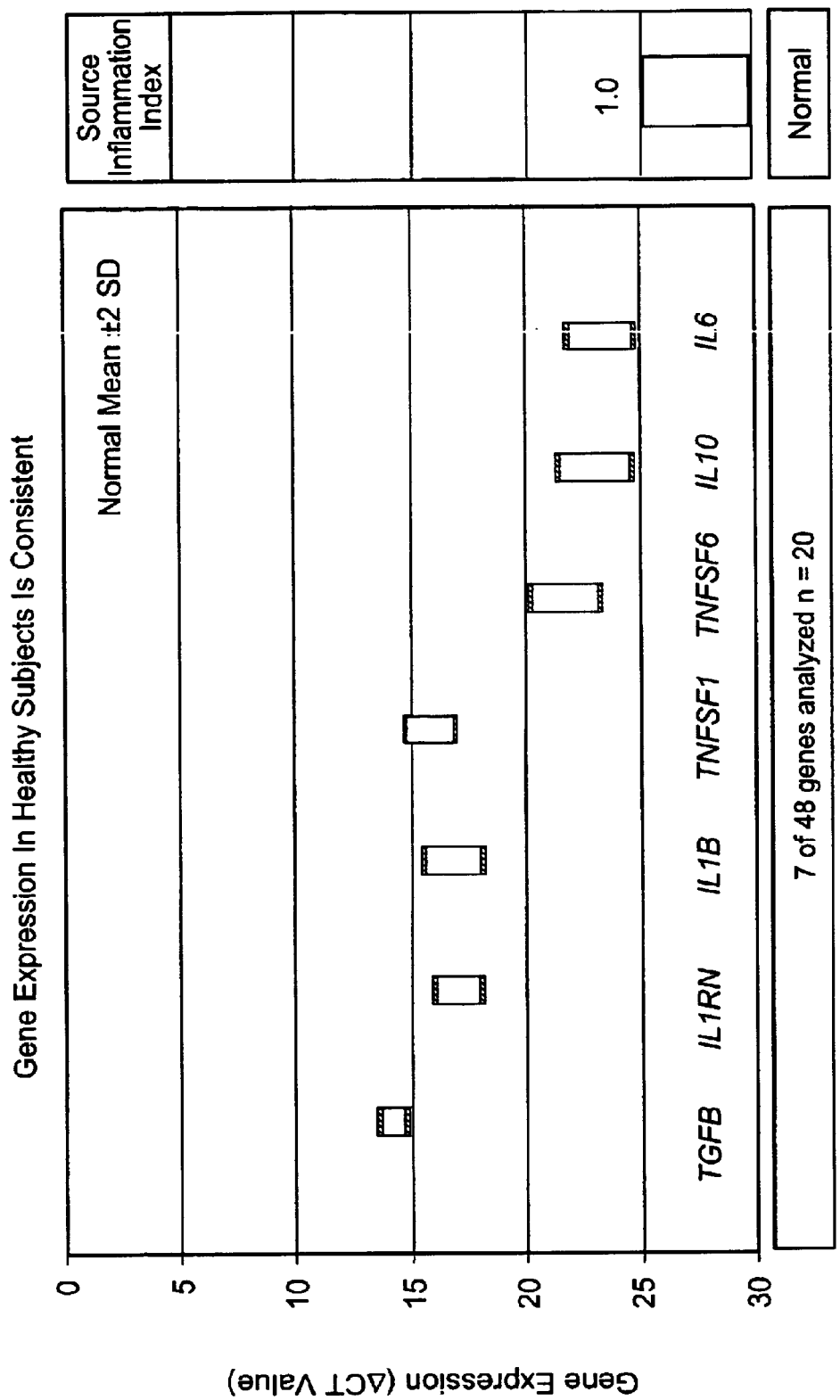
FIG. 17A further illustrates the consistency of inflammatory gene expression in a population.
Figure 17B:
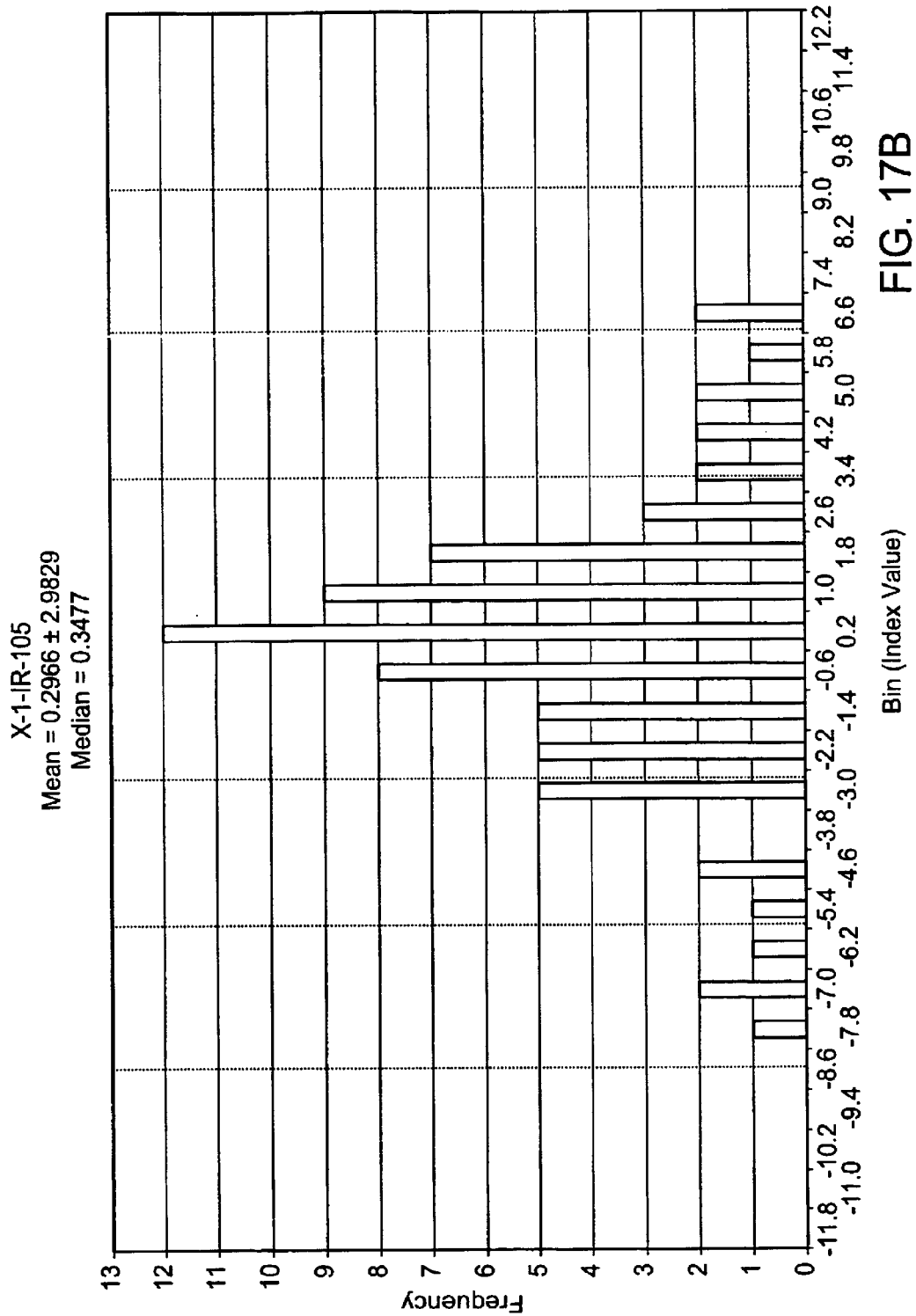
FIG. 17B shows the normal distribution of index values obtained from an undiagnosed population.

FIG. 17A further illustrates the consistency of inflammatory gene expression, illustrated here with respect to 7 loci of (of the Inflammation Gene Expression Panel of Table 1), in a population of 44 normal, undiagnosed blood donors. For each individual locus is shown the range of values lying within±2 standard deviations of the mean expression value, which corresponds to 95% of a normally distributed population. Notwithstanding the great width of the confidence interval (95%), the measured gene expression value (ΔCT)—remarkably—still lies within 10% of the mean, regardless of the expression level involved. As described in further detail below, for a given biological condition an index can be constructed to provide a measurement of the condition. This is possible as a result of the conjunction of two circumstances: (i) there is a remarkable consistency of Gene Expression Profiles with respect to a biological condition across a population and (ii) there can be employed procedures that provide substantially reproducible measurement of constituents in a Gene Expression Panel giving rise to a Gene Expression Profile, under measurement conditions wherein specificity and efficiencies of amplification for all constituents of the panel are substantially similar and which therefore provides a measurement of a biological condition. Accordingly, a function of the expression values of representative constituent loci of FIG. 17A is here used to generate an inflammation index value, which is normalized so that a reading of 1 corresponds to constituent expression values of healthy subjects, as shown in the right-hand portion of FIG. 17A.

In FIG. 17B, an inflammation index value was determined for each member of a population of 42 normal undiagnosed blood donors, and the resulting distribution of index values, shown in the figure, can be seen to approximate closely a normal distribution, notwithstanding the relatively small population size. The values of the index are shown relative to a 0-based median, with deviations from the median calibrated in standard deviation units. Thus 90% of the population lies within +1 and −1 of a 0 value. We have constructed various indices, which exhibit similar behavior.

Figure 17C:
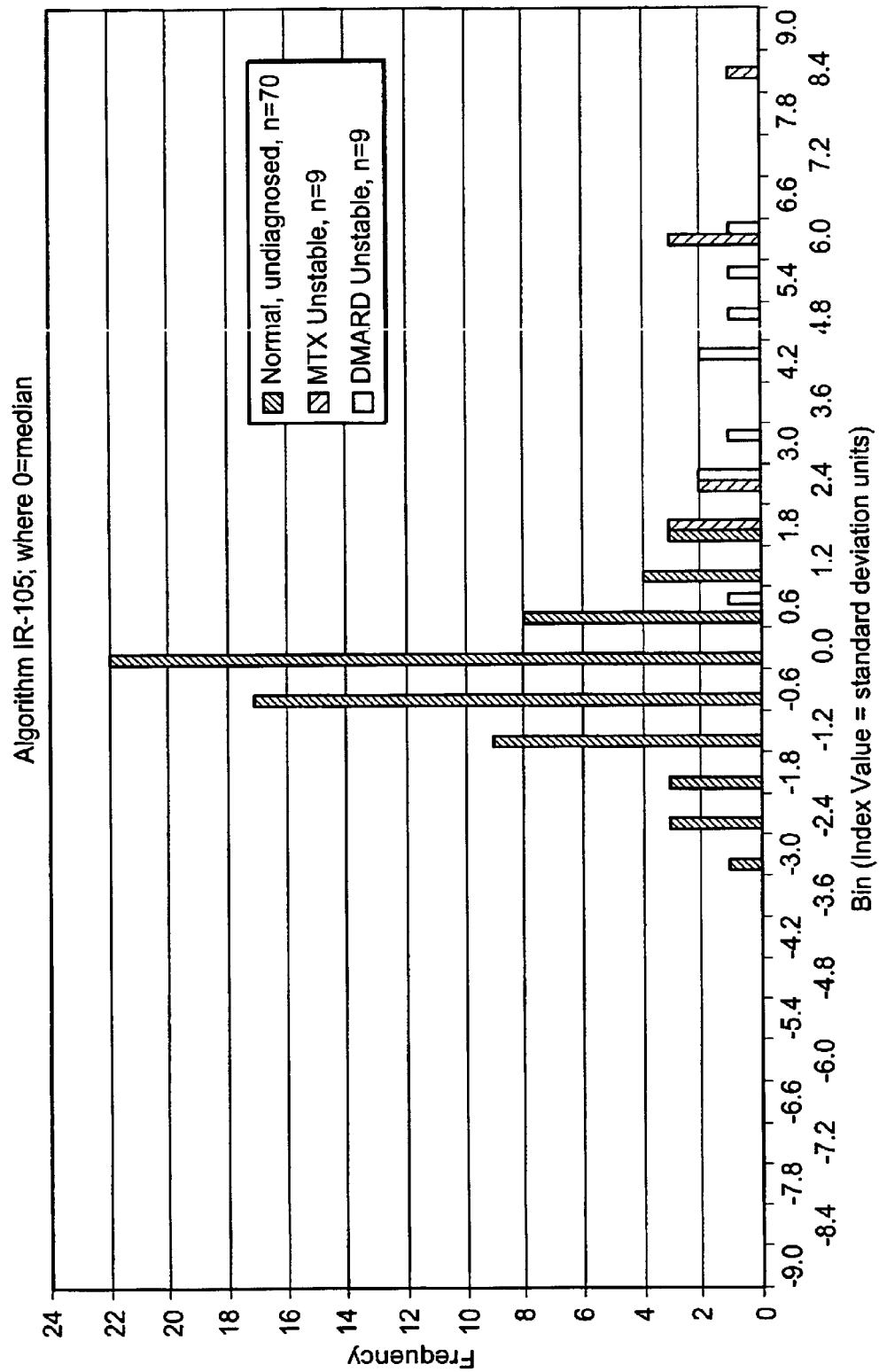
FIG. 17C illustrates the use of the same index as FIG. 17B, where the inflammation median for a normal population has been set to zero and both normal and diseased subjects are plotted in standard deviation units relative to that median.

FIG. 17C illustrates the use of the same index as FIG. 17B, where the inflammation median for a normal population has been set to zero and both normal and diseased subjects are plotted in standard deviation units relative to that median. An inflammation index value was determined for each member of a normal, undiagnosed population of 70 individuals (black bars). The resulting distribution of index values, shown in FIG. 17C, can be seen to approximate closely a normal distribution. Similarly, index values were calculated for individuals from two diseased population groups, (1) rheumatoid arthritis patients treated with methotrexate (MTX) who are about to change therapy to more efficacious drugs (e.g., TNF inhibitors)(hatched bars), and (2) rheumatoid arthritis patients treated with disease modifying anti-rheumatoid drugs (DMARDS) other than MTX, who are about to change therapy to more efficacious drugs (e.g., MTX). Both populations present index values that are skewed upward (demonstrating increased inflammation) in comparison to the normal distribution. This figure thus illustrates the utility of an index to derived from Gene Expression Profile data to evaluate disease status and to provide an objective and quantifiable treatment objective. When these two populations were treated appropriately, index values from both populations returned to a more normal distribution (data not shown here).

Figure 18:
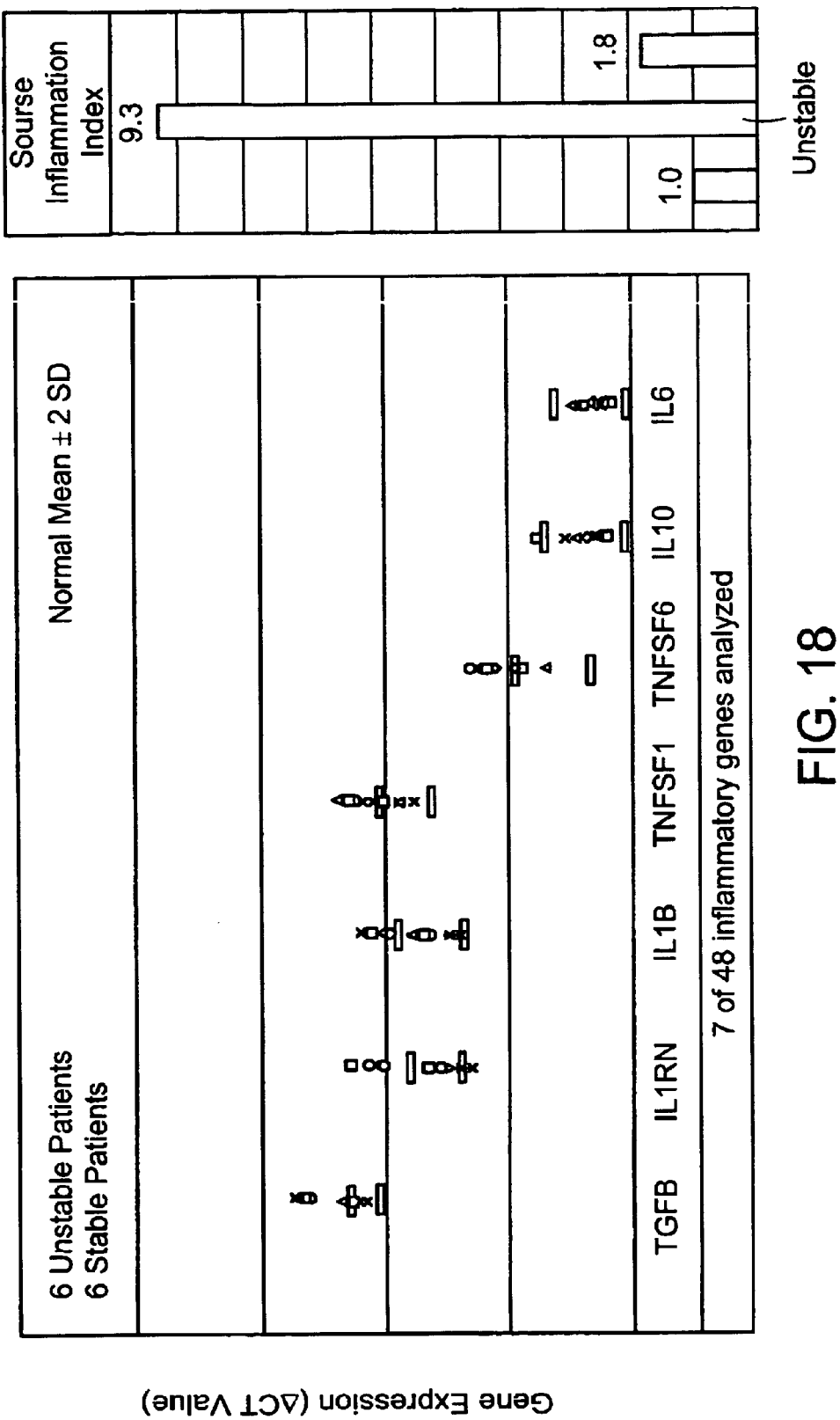
FIG. 18 plots, in a fashion similar to that of FIG. 17A, Gene Expression Profiles, for the same 7 loci as in FIG. 17A, two different (responder v. non-responder) 6-subject populations of rheumatoid arthritis patients.

FIG. 18 plots, in a fashion similar to that of FIG. 17A, Gene Expression Profiles, for the same 7 loci as in FIG. 17A, two different 6-subject populations of rheumatoid arthritis patients. One population (called "stable" in the figure) is of patients who have responded well to treatment and the other population (called "unstable" in the figure) is of patients who have not responded well to treatment and whose therapy is scheduled for change. It can be seen that the expression values for the stable population, lie within the range of the 95% confidence interval, whereas the expression values for the unstable population for 5 of the 7 loci are outside and above this range. The right-hand portion of the figure shows an average inflammation index of 9.3 for the unstable population and an average inflammation index of 1.8 for the stable population, compared to 1 for a normal undiagnosed population. The index thus provides a measure of the extent of the underlying inflammatory condition, in this case, rheumatoid arthritis. Hence the index, besides providing a measure of biological condition, can be used to measure the effectiveness of therapy as well as to provide a target for therapeutic intervention.

Figure 19:
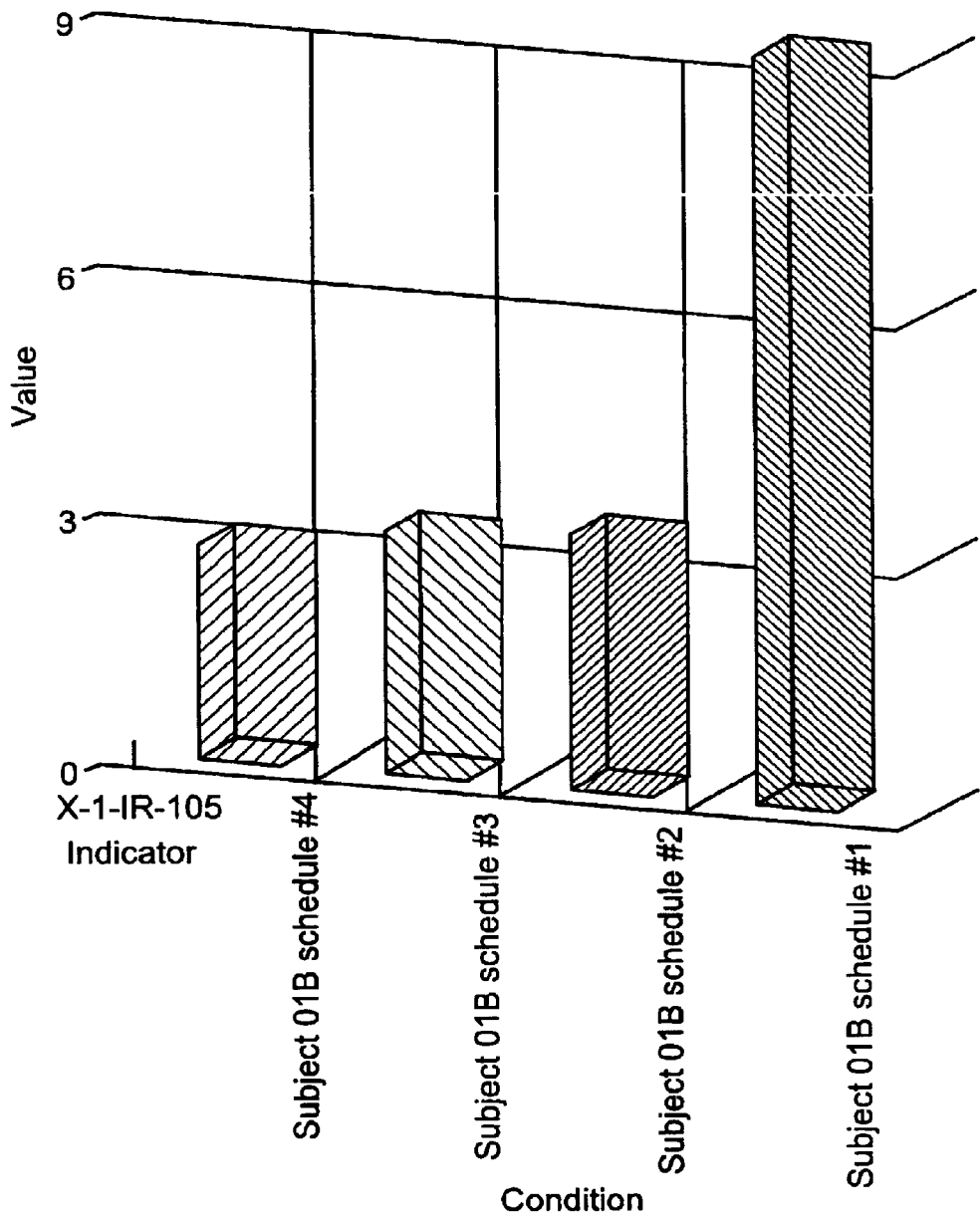
FIG. 19 thus illustrates use of the inflammation index for assessment of a single subject suffering from rheumatoid arthritis, who has not responded well to traditional therapy with methotrexate.

FIG. 19 thus illustrates use of the inflammation index for assessment of a single subject suffering from rheumatoid arthritis, who has not responded well to traditional therapy with methotrexate. The inflammation index for this subject is shown on the far right at start of a new therapy (a TNF inhibitor), and then, moving leftward, successively, 2 weeks, 6 weeks, and 12 weeks thereafter. The index can be seen moving towards normal, consistent with physician observation of the patient as responding to the new treatment.

Figure 20:
FIG. 20 similarly illustrates use of the inflammation index for assessment of three subjects suffering from rheumatoid arthritis, who have not responded well to traditional therapy with methotrexate.

FIG. 20 similarly illustrates use of the inflammation index for assessment of three subjects suffering from rheumatoid arthritis, who have not responded well to traditional therapy with methotrexate, at the beginning of new treatment (also with a TNF inhibitor), and 2 weeks and 6 weeks thereafter. The index in each case can again be seen moving generally towards normal, consistent with physician observation of the patients as responding to the new treatment.

Each of FIGS. 21–23 shows the inflammation index for an international group of subjects, suffering from rheumatoid arthritis, each of whom has been characterized as stable (that is, not anticipated to be subjected to a change in therapy) by the subject's treating physician. FIG. 21 shows the index for each of 10 patients in the group being treated with methotrexate, which known to alleviate symptoms without addressing the underlying disease. FIG. 22 shows the index for each of 10 patients in the group being treated with Enbrel (an TNF inhibitor), and FIG. 23 shows the index for each 10 patients being treated with Remicade (another TNF inhibitor). It can be seen that the inflammation index for each of the patients in FIG. 21 is elevated compared to normal, whereas in FIG. 22, the patients being treated with Enbrel as a class have an inflammation index that comes much closer to normal (80% in the normal range). In FIG. 23, it can be seen that, while all but one of the patients being treated with Remicade have an inflammation index at or below normal, two of the patients have an abnormally low inflammation index, suggesting an immunosuppressive response to this drug. (Indeed, studies have shown that Remicade has been associated with serious infections in some subjects, and here the immunosuppressive effect is quantified.) Also in FIG. 23, one subject has an inflammation index that is significantly above the normal range. This subject in fact was also on a regimen of an anti-inflammation steroid (prednisone) that was being tapered; within approximately one week after the inflammation index was sampled, the subject experienced a significant flare of clinical symptoms.

Remarkably, these examples show a measurement, derived from the assay of blood taken from a subject, pertinent to the subject's arthritic condition. Given that the measurement pertains to the extent of inflammation, it can be expected that other inflammation-based conditions, including, for example, cardiovascular disease, may be monitored in a similar fashion.

FIG. 24 illustrates use of the inflammation index for assessment of a single subject suffering from inflammatory bowel disease, for whom treatment with Remicade was initiated in three doses. The graphs show the inflammation index just prior to first treatment, and then 24 hours after the first treatment; the index has returned to the normal range. The index was elevated just prior to the second dose, but in the normal range prior to the third dose. Again, the index, besides providing a measure of biological condition, is here used to measure the effectiveness of therapy (Remicade), as well as to provide a target for therapeutic intervention in terms of both dose and schedule.

FIG. 25 shows Gene Expression Profiles with respect to 24 loci (of the Inflammation Gene Expression Panel of Table 1) for whole blood treated with Ibuprofen in vitro in relation to other non-steroidal anti-inflammatory drugs (NSAIDs). The profile for Ibuprofen is in front. It can be seen that all of the NSAIDs, including Ibuprofen share a substantially similar profile, in that the patterns of gene expression across the loci are similar. Notwithstanding these similarities, each individual drug has its own distinctive signature.

FIG. 26 illustrates how the effects of two competing anti-inflammatory compounds can be compared objectively, quantitatively, precisely, and reproducibly. In this example, expression of each of a panel of two genes (of the Inflammation Gene Expression Panel of Table 1) is measured for varying doses (0.08–250 µg/ml) of each drug in vitro in whole blood. The market leader drug shows a complex relationship between dose and inflammatory gene response. Paradoxically, as the dose is increased, gene expression for both loci initially drops and then increases in the case the case of the market leader. For the other compound, a more consistent response results, so that as the dose is increased, the gene expression for both loci decreases more consistently.

FIGS. 27 through 41 illustrate the use of gene expression panels in early identification and monitoring of infectious disease. These figures plot the response, in expression products of the genes indicated, in whole blood, to the administration of various infectious agents or products associated with infectious agents. In each figure, the gene expression levels are "calibrated", as that term is defined herein, in relation to baseline expression levels determined with respect to the whole blood prior to administration of the relevant infectious agent. In this respect the figures are similar in nature to various figures of our below-referenced patent application WO 01/25473 (for example, FIG. 15 therein). The concentration change is shown ratiometrically, and the baseline level of 1 for a particular gene locus corresponds to an expression level for such locus that is the same, monitored at the relevant time after addition of the infectious agent or other stimulus, as the expression level before addition of the stimulus. Ratiometric changes in concentration are plotted on a logarithmic scale. Bars below the unity line represent decreases in concentration and bars above the unity line represent increases in concentration, the magnitude of each bar indicating the magnitude of the ratio of the change. We have shown in WO 01/25473 and other experiments that, under appropriate conditions, Gene Expression Profiles derived in vitro by exposing whole blood to a stimulus can be representative of Gene Expression Profiles derived in vivo with exposure to a corresponding stimulus.

FIG. 27 uses a novel bacterial Gene Expression Panel of 24 genes, developed to discriminate various bacterial conditions in a host biological system. Two different stimuli are employed: lipotechoic acid (LTA), a gram positive cell wall constituent, and lipopolysaccharide (LPS), a gram negative cell wall constituent. The final concentration immediately after administration of the stimulus was 100 ng/mL, and the ratiometric changes in expression, in relation to pre-administration levels, were monitored for each stimulus 2 and 6 hours after administration. It can be seen that differential expression can be observed as early as two hours after administration, for example, in the IFNA2 locus, as well as others, permitting discrimination in response between gram positive and gram negative bacteria.

FIG. 28 shows differential expression for a single locus, IFNG, to LTA derived from three distinct sources: S. pyogenes, B. subtilis, and S. aureus. Each stimulus was administered to achieve a concentration of 100 ng/mL, and the response was monitored at 1, 2, 4, 6, and 24 hours after administration. The results suggest that Gene Expression Profiles can be used to distinguish among different infectious agents, here different species of gram positive bacteria.

FIGS. 29 and 30 show the response of the Inflammation 48A and 48B loci respectively (discussed above in connection with FIGS. 6 and 7 respectively) in whole blood to administration of a stimulus of S. aureus and of a stimulus of E. coli (in the indicated concentrations, just after administration, of $10^7$ and $10^6$ CFU/mL respectively), monitored 2 hours after administration in relation to the pre-administration baseline. The figures show that many of the loci respond to the presence of the bacterial infection within two hours after infection.

FIGS. 31 and 32 correspond to FIGS. 29 and 30 respectively and are similar to them, with the exception that the monitoring here occurs 6 hours after administration. More of the loci are responsive to the presence of infection. Various loci, such as IL2, show expression levels that discriminate between the two infectious agents.

FIG. 33 shows the response of the Inflammation 48A loci to the administration of a stimulus of E. coli (again in the concentration just after administration of $10^6$ CFU/mL) and to the administration of a stimulus of an E. coli filtrate containing E. coli bacteria by products but lacking E. coli bacteria. The responses were monitored at 2, 6, and 24 hours after administration. It can be seen, for example, that the responses over time of loci IL1B, IL18 and CSF3 to E. coli and to E. coli filtrate are different.

FIG. 34 is similar to FIG. 33, but here the compared responses are to stimuli from E. coli filtrate alone and from E. coli filtrate to which has been added polymyxin B, an antibiotic known to bind to lipopolysaccharide (LPS). An examination of the response of IL1B, for example, shows that presence of polymyxin B did not affect the response of the locus to E. coli filtrate, thereby indicating that LPS does not appear to be a factor in the response of IL1B to E. coli filtrate.

FIG. 35 illustrates the responses of the Inflammation 48A loci over time of whole blood to a stimulus of S. aureus (with a concentration just after administration of $10^7$ CFU/mL) monitored at 2, 6, and 24 hours after administration. It can be seen that response over time can involve both direction and magnitude of change in expression. (See for example, IL5 and IL18.)

Figure 36:
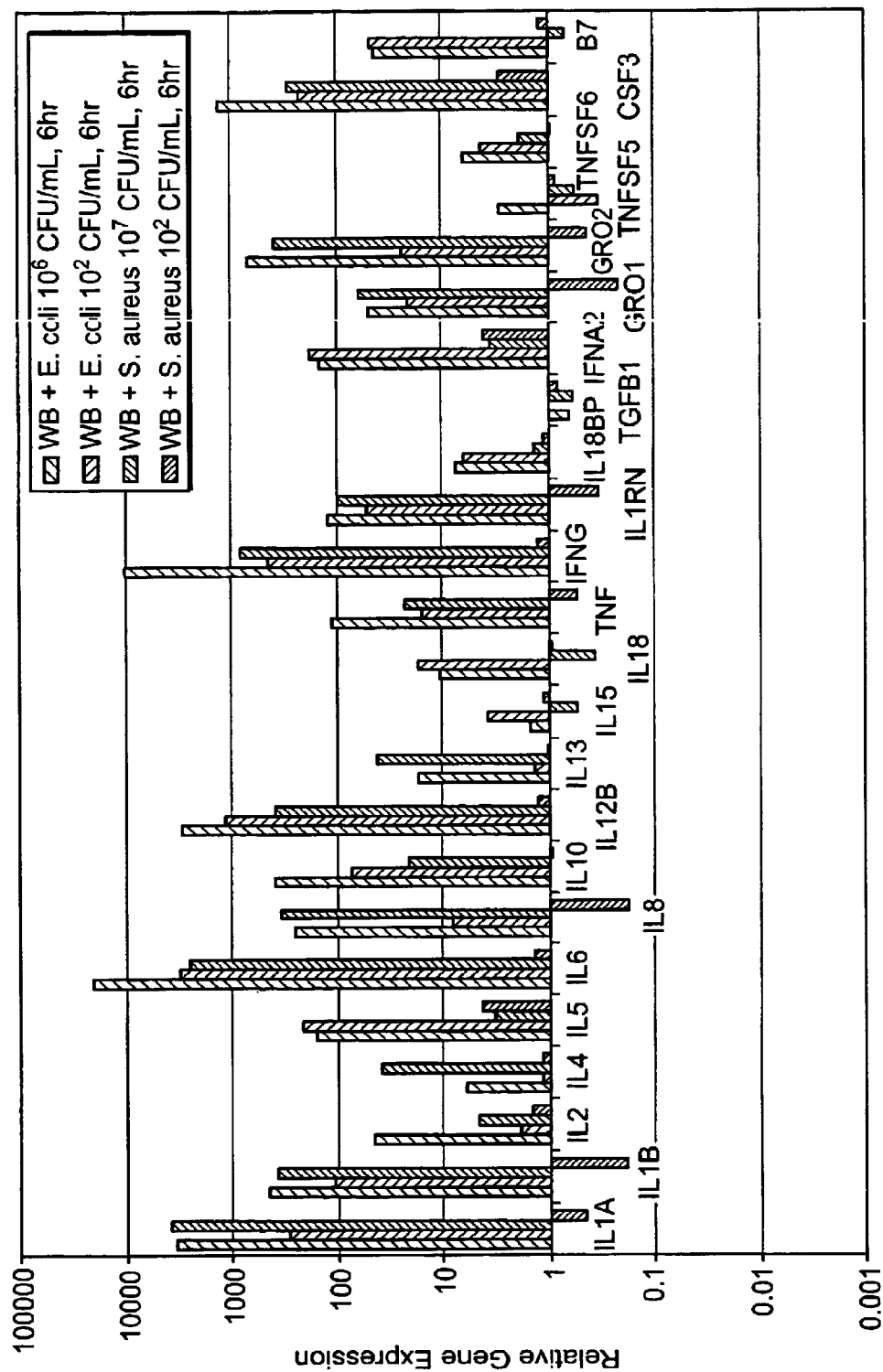
Figure 37:
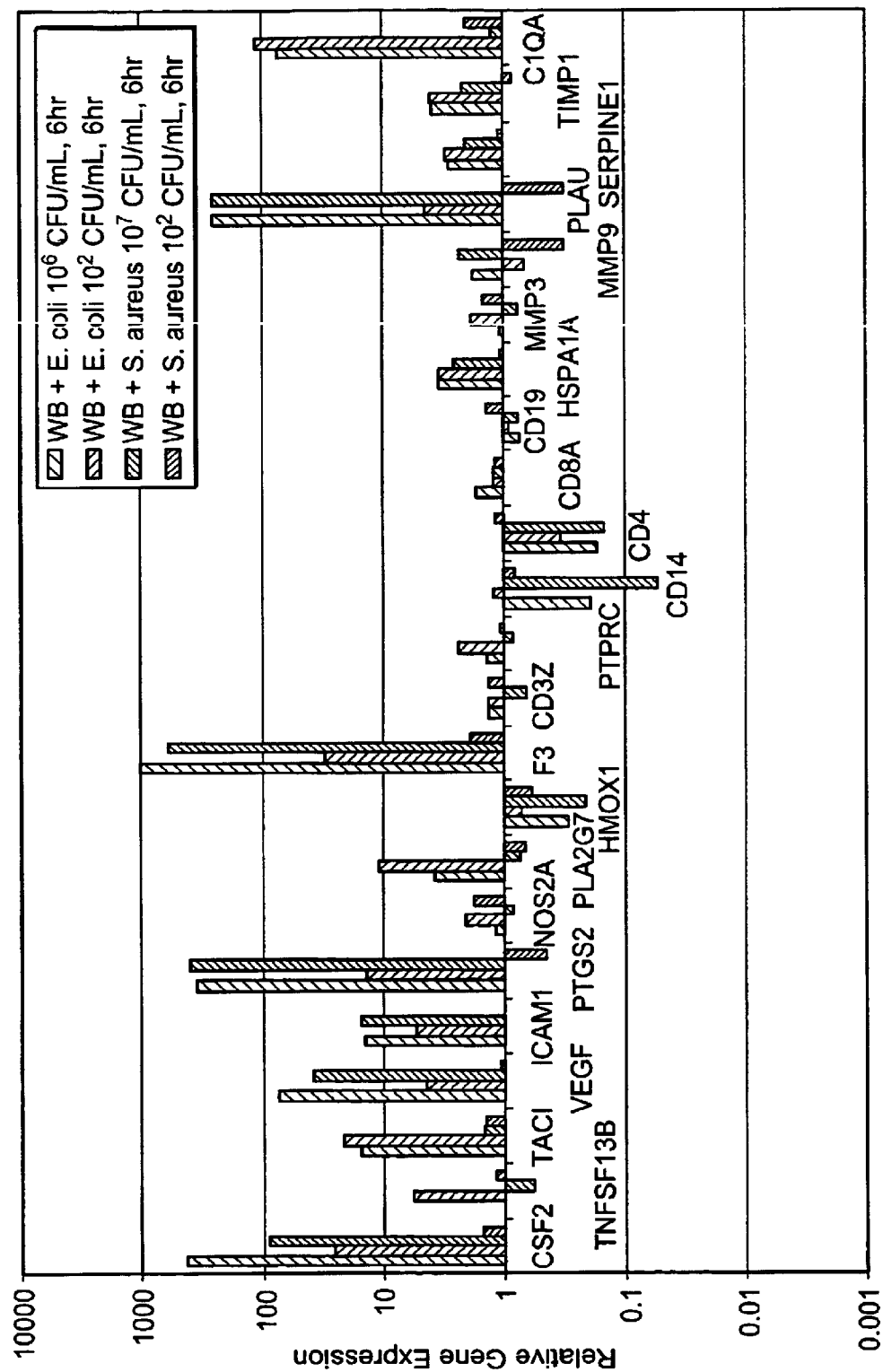

FIGS. 36 and 37 show the responses, of the Inflammation 48A and 48B loci respectively, monitored at 6 hours to stimuli from E. coli (at concentrations of $10^6$ and $10^2$ CFU/mL immediately after administration) and from S. aureus (at concentrations of $10^7$ and $10^2$ CFU/mL immediately after administration). It can be seen, among other things, that in various loci, such as B7 (FIG. 36), TACI, PLA2G7, and C1QA (FIG. 37), E. coli produces a much more pronounced response than S. aureus. The data suggest strongly that Gene Expression Profiles can be used to identify with high sensitivity the presence of gram negative bacteria and to discriminate against gram positive bacteria.

Figure 38:
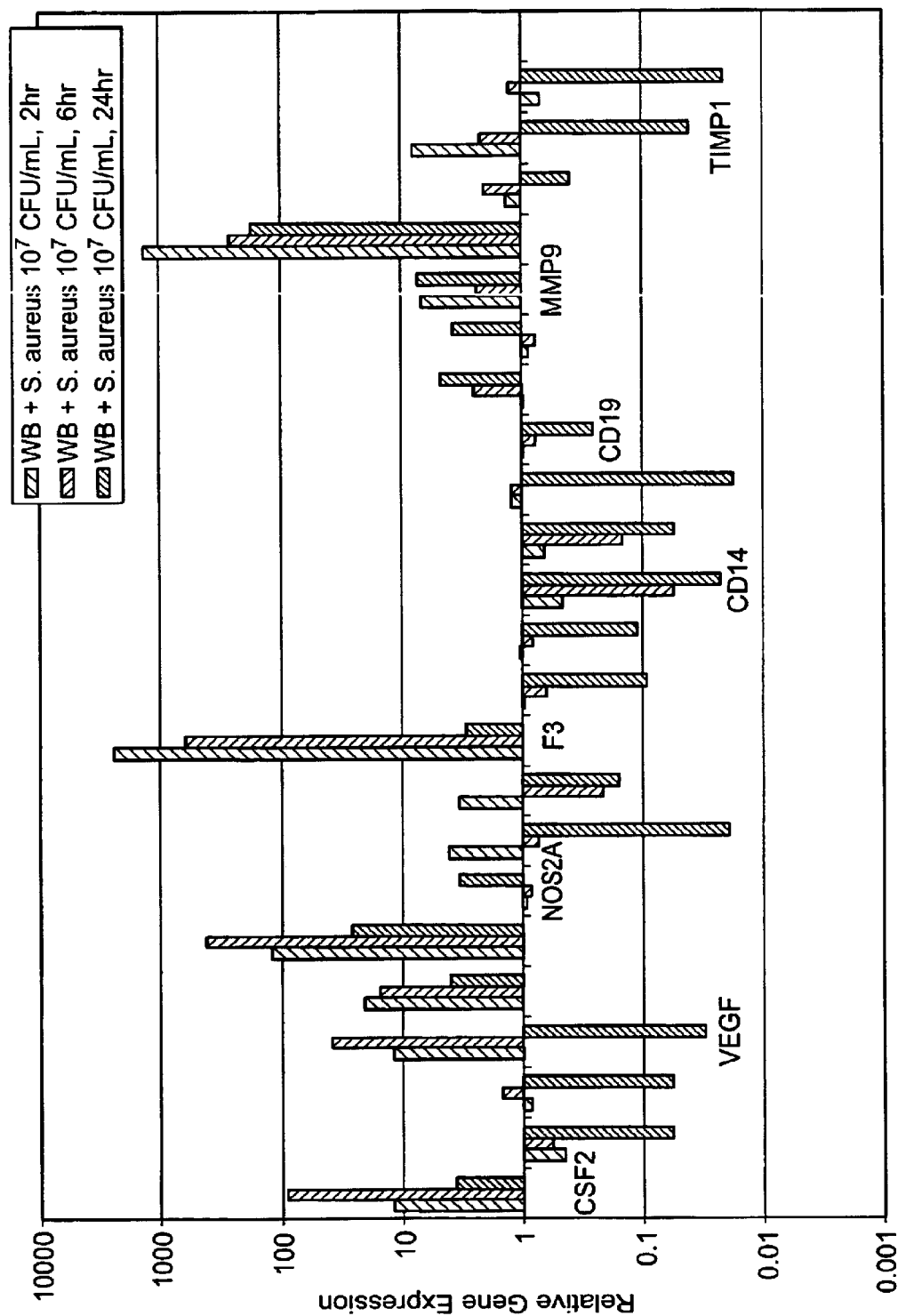
Figure 39:
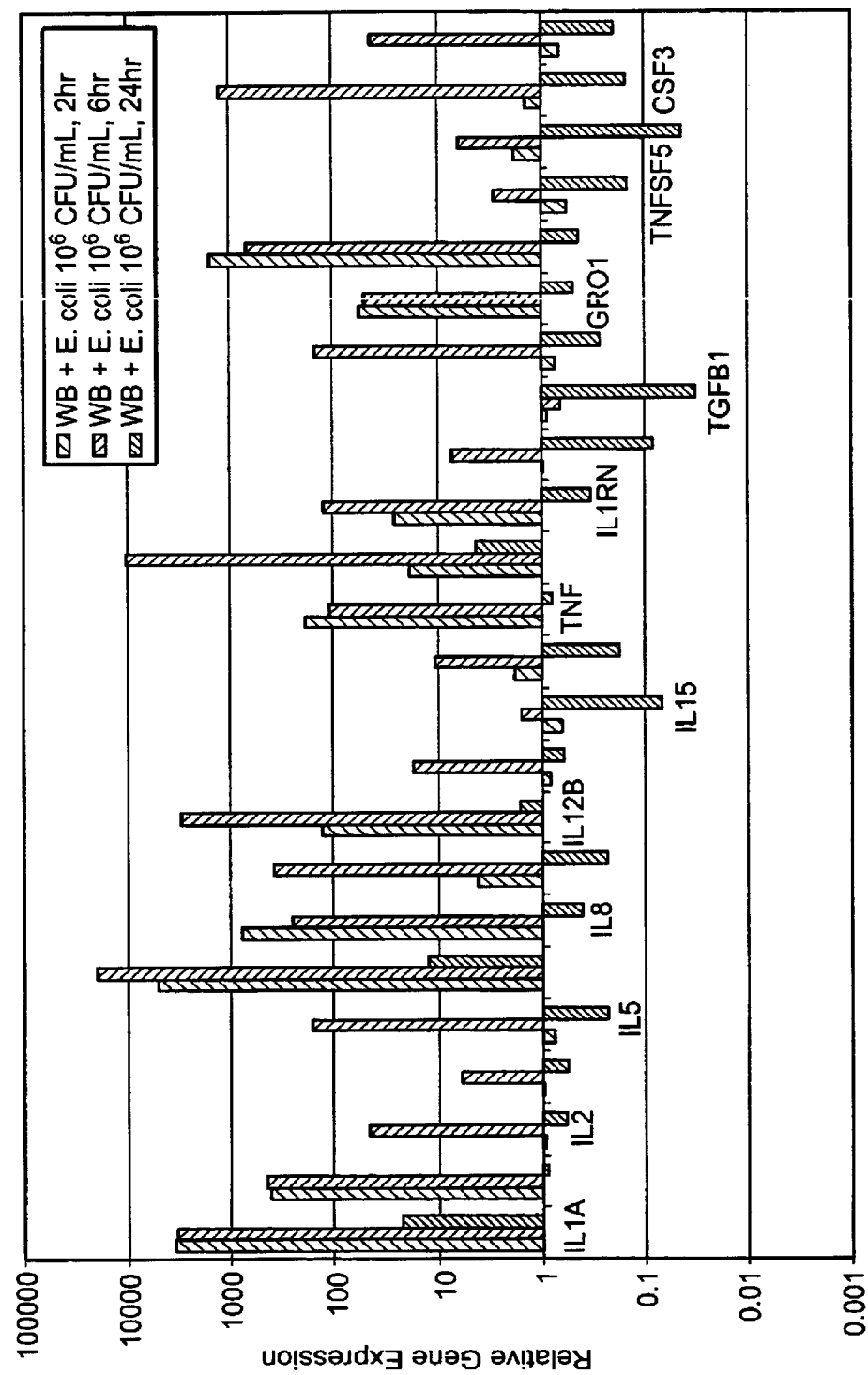

FIGS. 38 and 39 show the responses, of the Inflammation 48B and 48A loci respectively, monitored 2, 6, and 24 hours after administration, to stimuli of high concentrations of S. aureus and E. coli respectively (at respective concentrations of $10^7$ and $10^6$ CFU/mL immediately after administration). The responses over time at many loci involve changes in magnitude and direction.

Figure 40:
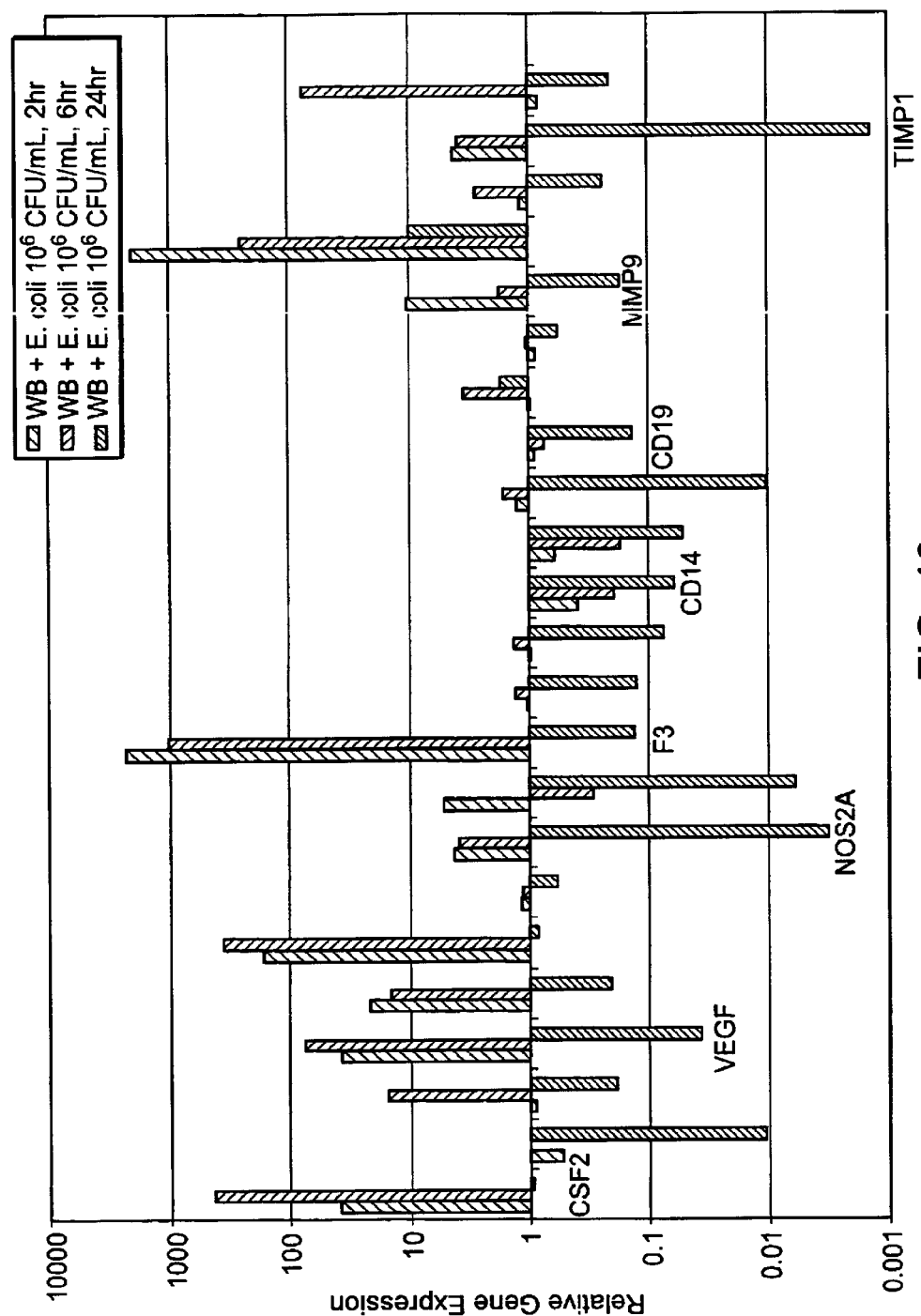

FIG. 40 is similar to FIG. 39, but shows the responses of the Inflammation 48B loci.

Figure 41:
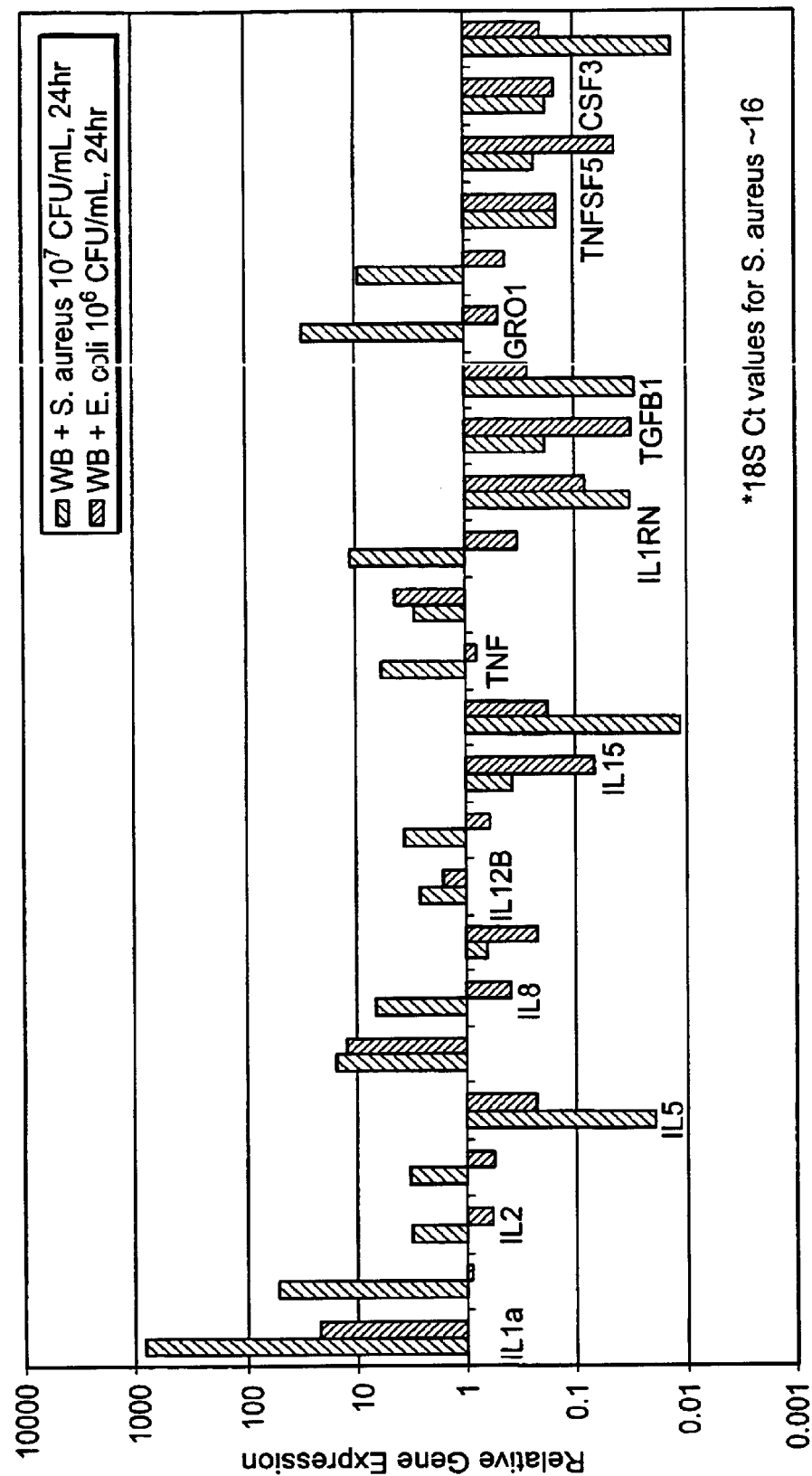

FIG. 41 similarly shows the responses of the Inflammation 48A loci monitored at 24 hours after administration to stimuli high concentrations of S. aureus and E. coli respectively (at respective concentrations of $10^7$ and $10^6$ CFU/mL immediately after administration). As in the case of FIGS. 20 and 21, responses at some loci, such as GRO1 and GRO2, discriminate between type of infection.

These data support our conclusion that Gene Expression Profiles with sufficient precision and calibration as described herein (1) can determine subpopulations of individuals with a known biological condition; (2) may be used to monitor the response of patients to therapy; (3) may be used to assess the efficacy and safety of therapy; and (4) may used to guide the medical management of a patient by adjusting therapy to bring one or more relevant Gene Expression Profiles closer to a target set of values, which may be normative values or other desired or achievable values. We have shown that Gene Expression Profiles may provide meaningful information even when derived from ex vivo treatment of blood or other tissue. We have also shown that Gene Expression Profiles derived from peripheral whole blood are informative of a wide range of conditions neither directly nor typically associated with blood.

Furthermore, in embodiments of the present invention, Gene Expression Profiles can also be used for characterization and early identification (including pre-symptomatic states) of infectious disease, such as sepsis. This characterization includes discriminating between infected and uninfected individuals, bacterial and viral infections, specific subtypes of pathogenic agents, stages of the natural history of infection (e.g., early or late), and prognosis. Use of the algorithmic and statistical approaches discussed above to achieve such identification and to discriminate in such fashion is within the scope of various embodiments herein.

TABLE 1

Inflammation Gene Expression Panel

| Symbol | Name | Classification | Description |
|---|---|---|---|
| IL1A | Interleukin 1, alpha | cytokines-chemokines-growth factors | Proinflammatory; constitutively and inducibly expressed in variety of cells. Generally cytosolic and released only during severe inflammatory disease |
| IL1B | Interleukin 1, beta | cytokines-chemokines-growth factors | Proinflammatory; constitutively and inducibly expressed by many cell types, secreted |
| TNFA | Tumor necrosis factor, alpha | cytokines-chemokines-growth factors | Proinflammatory, TH1, mediates host response to bacterial stimulus, regulates cell growth & differentiation |
| IL6 | Interleukin 6 (interferon, beta 2) | cytokines-chemokines-growth factors | Pro- and antiinflammatory activity, TH2 cytokine, regulates hemotopoietic system and activation of innate response |
| IL8 | Interleukin 8 | cytokines-chemokines-growth factors | Proinflammatory, major secondary inflammatory mediator, cell adhesion, signal transduction, cell-cell signaling, angiogenesis, synthesized by a wide variety of cell types |
| IFNG | Interferon gamma | cytokines-chemokines-growth factors | Pro- and antiinflammatory activity, TH1 cytokine, nonspecific inflammatory mediator, produced by activated T-cells |
| IL2 | Interleukin 2 | cytokines-chemokines-growth factors | T-cell growth factor, expressed by activated T-cells, regulates lymphocyte activation and differentiation; inhibits apoptosis, TH1 cytokine |
| IL12B | Interleukin 12 p40 | cytokines-chemokines-growth factors | Proinflammatory; mediator of innate immunity, TH1 cytokine, requires co-stimulation with IL-18 to induce IFN-g |
| IL15 | Interleukin 15 | cytokines-chemokines-growth factors | Proinflammatory; mediates T-cell activation, inhibits apoptosis, synergizes with IL-2 to induce IFN-g and TNF-a |
| IL18 | Interleukin 18 | cytokines-chemokines-growth factors | Proinflammatory, TH1, innate and aquired immunity, promotes apoptosis, requires co-stimulation with IL-1 or IL-2 to induce TH1 cytokines in T- and NK-cells |
| IL4 | Interleukin 4 | cytokines-chemokines-growth factors | Antiinflammatory; TH2; suppresses proinflammatory cytokines, increases expression of IL-1RN, regulates lymphocyte activation |
| IL5 | Interleukin 5 | cytokines-chemokines-growth factors | Eosinophil stimulatory factor; stimulates late B cell differentiation to secretion of Ig |
| IL10 | Interleukin 10 | cytokines-chemokines-growth factors | Antiinflammatory; TH2; suppresses production of proinflammatory cytokines |
| IL13 | Interleukin 13 | cytokines-chemokines-growth factors | Inhibits inflammatory cytokine production |
| IL1RN | Interleukin 1 receptor antagonist | cytokines-chemokines-growth factors | IL1 receptor antagonist; Antiinflammatory; inhibits binding of IL-1 to IL-1 receptor by binding to receptor without stimulating IL-1-like activity |
| IL18BP | IL-18 Binding Protein | cytokines-chemokines-growth factors | Implicated in inhibition of early TH1 cytokine responses |
| TGFB1 | Transforming growth factor, beta 1 | cytokines-chemokines-growth factors | Pro- and antiinflammatory activity, anti-apoptotic; cell-cell signaling, can either inhibit or stimulate cell growth |

TABLE 1-continued

Inflammation Gene Expression Panel

| Symbol | Name | Classification | Description |
|---|---|---|---|
| IFNA2 | Interferon, alpha 2 | cytokines-chemokines-growth factors | interferon produced by macrophages with antiviral effects |
| GRO1 | GRO1 oncogene (melanoma growth stimulating activity, alpha) | cytokines-chemokines-growth factors | AKA SCYB1; chemotactic for neutrophils |
| GRO2 | GRO2 oncogene | cytokines-chemokines-growth factors | AKA MIP2, SCYB2; Macrophage inflammatory protein produced by moncytes and neutrophils |
| TNFSF5 | Tumor necrosis factor (ligand) superfamily, member 5 | cytokines-chemokines-growth factors | ligand for CD40; expressed on the surface of T cells. It regulates B cell function by engaging CD40 on the B cell surface |
| TNFSF6 | Tumor necrosis factor (ligand) superfamily, member 6 | cytokines-chemokines-growth factors | AKA FasL; Ligand for FAS antigen; transduces apoptotic signals into cells |
| CSF3 | Colony stimulating factor 3 (granulocyte) | cytokines-chemokines-growth factors | AKA GCSF; cytokine that stimulates granulocyte development |
| B7 | B7 protein | cell signaling and activation | Regulatory protein that may be associated with lupus |
| CSF2 | Granulocyte-monocyte colony stimulating factor | cytokines-chemokines-growth factors | AKA GM-CSF; Hematopoietic growth factor; stimulates growth and differentiation of hematopoietic precursor cells from various lineages, including granulocytes, macrophages, eosinophils, and erythrocytes |
| TNFSF13B | Tumor necrosis factor (ligand) superfamily, member 13b | cytokines-chemokines-growth factors | B cell activating factor, TNF family |
| TACI | Transmembrane activator and CAML interactor | cytokines-chemokines-growth factors | T cell activating factor and calcium cyclophilin modulator |
| VEGF | vascular endothelial growth factor | cytokines-chemokines-growth factors | Producted by monocytes |
| ICAM1 | Intercellular adhesion molecule 1 | Cell Adhesion/Matrix Protein | Endothelial cell surface molecule; regulates cell adhesion and trafficking, upregulated during cytokine stimulation |
| PTGS2 | Prostaglandin-endoperoxide synthase 2 | Enzyme/Redox | AKA COX2; Proinflammatory, member of arachidonic acid to prostanoid conversion pathway; induced by proinflammatory cytokines |
| NOS2A | Nitric oxide synthase 2A | Enzyme/Redox | AKA iNOS; produces NO which is bacteriocidal/tumoricidal |
| PLA2G7 | Phospholipase A2, group VII (platelet activating factor acetylhydrolase, plasma) | Enzyme/Redox | Platelet activating factor |
| HMOX1 | Heme oxygenase (decycling) 1 | Enzyme/Redox | Endotoxin inducible |
| F3 | F3 | Enzyme/Redox | AKA thromboplastin, Coagulation Factor 3; cell surface glycoprotein responsible for coagulation catalysis |
| CD3Z | CD3 antigen, zeta polypeptide | Cell Marker | T-cell surface glycoprotein |

TABLE 1-continued

Inflammation Gene Expression Panel

| Symbol | Name | Classification | Description |
| --- | --- | --- | --- |
| PTPRC | protein tyrosine phosphatase, receptor type, C | Cell Marker | AKA CD45; mediates T-cell activation |
| CD14 | CD14 antigen | Cell Marker | LPS receptor used as marker for monocytes |
| CD4 | CD4 antigen (p55) | Cell Marker | Helper T-cell marker |
| CD8A | CD8 antigen, alpha polypeptide | Cell Marker | Suppressor T cell marker |
| CD19 | CD19 antigen | Cell Marker | AKA Leu 12; B cell growth factor |
| HSPA1A | Heat shock protein 70 | Cell Signaling and activation | heat shock protein 70 kDa |
| MMP3 | Matrix metalloproteinase 3 | Proteinase/Proteinase Inhibitor | AKA stromelysin; degrades fibronectin, laminin and gelatin |
| MMP9 | Matrix metalloproteinase 9 | Proteinase/Proteinase Inhibitor | AKA gelatinase B; degrades extracellular matrix molecules, secreted by IL-8-stimulated neutrophils |
| PLAU | Plasminogen activator, urokinase | Proteinase/Proteinase Inhibitor | AKA uPA; cleaves plasminogen to plasmin (a protease responsible for nonspecific extracellular matrix degradation) |
| SERPINE1 | Serine (or cysteine) protease inhibitor, clade B (ovalbumin), member 1 | Proteinase/Proteinase Inhibitor | Plasminogen activator inhibitor-1/PAI-1 |
| TIMP1 | tissue inhibitor of metalloproteinase 1 | Proteinase/Proteinase Inhibitor | Irreversibly binds and inhibits metalloproteinases, such as collagenase |
| C1QA | Complement component 1, q subcomponent, alpha polypeptide | Proteinase/Proteinase Inhibitor | Serum complement system; forms C1 complex with the proenzymes c1r and c1s |
| HLA-DRB1 | Major histocompatibility complex, class II, DR beta 1 | Histocompatibility | Binds antigen for presentation to CD4+ cells |

TABLE 2

Diabetes Gene Expression Panel

| Symbol | Name | Classification | Description |
| --- | --- | --- | --- |
| G6PC | glucose-6-phosphatase, catalytic | Glucose-6-phosphatase/Glycogen metabolism | Catalyzes the final step in the gluconeogenic and glycogenolytic pathways. Stimulated by glucocorticoids and strongly inhibited by insulin. Overexpression (in conjunction with PCK1 overexpression) leads to increased hepatic glucose production. |
| GCG | glucagon | pancreatic/peptide hormone | Pancreatic hormone which counteracts the glucose-lowering action of insulin by stimulating glycogenolysis and gluconeogenesis. Underexpression of glucagon is preferred. Glucagon-like peptide (GLP-1) proposed for type 2 diabetes treatment inhibits glucag |
| GCGR | glucagon receptor | glucagon receptor | Expression of GCGR is strongly upregulated by glucose. Deficiency imbalance could play a role in NIDDM. Has been looked as a potential for gene therapy. |

TABLE 2-continued

Diabetes Gene Expression Panel

| Symbol | Name | Classification | Description |
|---|---|---|---|
| GFPT1 | glutamine-fructose-6-phosphate transaminase 1 | Glutamine amidotransferase | The rate limiting enzyme for glucose entry into the hexosamine biosynthetic pathway (HBP). Overexpression of GFA in muscle and adipose tissue increases products of the HBP which are thought to cause insulin resistance (possibly through defects to glucose |
| GYS1 | glycogen synthase 1 (muscle) | Transferase/Glycogen metabolism | A key enzyme in the regulation of glycogen synthesis in the skeletal muscles of humans. Typically stimulated by insulin, but in NIDDM individuals GS is shown to be completely resistant to insulin stimulation (decreased activity and activation in muscle) |
| HK2 | hexokinase 2 | hexokinase | Phosphorylates glucose into glucose-6-phosphate. NIDDM patients have lower HK2 activity which may contribute to insulin resistance. Similar action to GCK. |
| INS | insulin | Insulin receptor ligand | Decreases blood glucose concentration and accelerates glycogen synthesis in the liver. Not as critical in NIDDM as in IDDM. |
| IRS1 | insulin receptor substrate 1 | signal transduction/transmembrane receptor protein | Positive regultion of insulin action. This protein is activated when insulin binds to insulin receptor - binds 85-kDa subunit of PI 3-K. decreased in skeletal muscle of obese humans. |
| PCK1 | phosphoenolpyruvate carboxykinase 1 | rate-limiting gluconeogenic enzyme | Rate limiting enzyme for gluconeogenesis - plays a key role in the regulation of hepatic glucose output by insulin and glucagon. Overexpression in the liver results in increased hepatic glucose production and hepatic insulin resistance to glycogen synthe |
| PIK3R1 | phosphoinositide-3-kinase, regulatory subunit, polypeptide 1 (p85 alpha) | regulatory enzyme | Positive regulation of insulin action. Docks in IRS proteins and Gab1 - activity is required for insulin stimulated translocation of glucose transporters the plasma membrane and activation glucose uptake. |
| PPARG | peroxisome proliferator-activated receptor, gamma | transcription factor/Ligand-dependent nuclear receptor | The primary pharmacological target for the treatment of insulin resistance in NIDDM. Involved in glucose and lipid metabolism in skeletal muscle. |
| PRKCB1 | protein kinase C, beta 1 | protein kinase C/protein phosphorylation | Negative regulation of insulin action. Activated by hyperglycemia - increases phosphorylation of IRS-1 and reduces insulin receptor kinase activity. Increased PKC activation may lead to oxidative stress causing overexpression of TGF-beta and fibronectin |
| SLC2A2 | solute carrier family 2 (facilitated glucose transporter), member 2 | glucose transporter | Glucose transporters expressed uniquely in b-cells and liver. Transport glucose into the b-cell. Typically underexpressed in pancreatic islet cells of individuals with NIDDM. |
| SLC2A4 | solute carrier family 2 (facilitated glucose transporter), member 4 | glucose transporter | Glucose transporter protein that is final mediator in insulin-stimulated glucose uptake (rate limiting for glucose uptake). Underexpression not important, but overexpression in muscle and adipose tissue consistently shown to increase glucose transport. |
| TGFB1 | transforming growth factor, beta 1 | Transforming growth factor beta receptor ligand | Regulated by glucose - in NIDDM individuals, overexpression (due to oxidative stress - see PKC) promotes renal cell hypertrophy leading to diabetic nephropathy. |
| TNF | tumor necrosis factor | cytokine/tumor necrosis factor receptor ligand | Negative regulation of insulin action. Produced in excess by adipose tissue of obese individuals - increases IRS-1 |

TABLE 2-continued

Diabetes Gene Expression Panel

| Symbol | Name | Classification | Description |
|---|---|---|---|
| | | | phosphorylation and decreases insulin receptor kinase activity. |

TABLE 3

Prostate Gene Expression Panel

| Symbol | Name | Classification | Description |
|---|---|---|---|
| ABCC1 | ATP-binding cassette, sub-family C, member 1 | membrane transporter | AKA MRP1, ABC29: Multispecific organic anion membrane transporter; overexpression confers tissue protection against a wide variety of xenobiotics due to their removal from the cell. |
| ACPP | Acid phosphatase, prostate | phosphatase | AKA PAP: Major phosphatase of the prostate; synthesized under androgen regulation; secreted by the epithelial cells of the prostrate |
| BCL2 | B-cell CLL/lymphoma 2 | apoptosis Inhibitor - cell cycle control - oncogenesis | Blocks apoptosis by interfering with the activation of caspases |
| BIRC5 | Baculoviral IAP repeat-containing 5 | apoptosis Inhibitor | AKA Survivin; API4: May counteract a default induction of apoptosis in G2/M phase of cell cycle; associates with microtubules of the mitotic spindle during apoptosis |
| CDH1 | Cadherin 1, type 1, E-cadherin | cell-cell adhesion/ interaction | AKA ECAD, UVO: Calcium ion-dependent cell adhesion molecule that mediates cell to cell interactions in epithelial cells |
| CDH2 | Cadherin 2, type 1, N-cadherin | cell-cell adhesion/ interaction | AKA NCAD, CDHN: Calcium-dependent glycoprotein that mediates cell-cell interactions; may be involved in neuronal recognition mechanism |
| CDKN2A | Cyclin-dependent kinase inhibitor 2A | cell cycle control - tumor suppressor | AKA p16, MTS1, INK4: Tumor suppressor gene involved in a variety of malignancies; arrests normal diploid cells in late G1 |
| CTNNA1 | Catenin, alpha 1 | cell adhesion | Binds cadherins and links them with the actin cytoskeleton |
| FOLH1 | Folate Hydrolase | hydrolase | AKA PSMA, GCP2: Expressed in normal and neoplastic prostate cells; membrane bound glycoprotein; hydrolyzes folate and is an N-acetylated a-linked acidic dipeptidase |
| GSTT1 | Glutathione-S-Transferase, theta 1 | metabolism | Catalyzes the conjugation of reduced glutathione to a wide number of exogenous and endogenous hydrophobic electrophiles; has an important role in human carcinogenesis |
| HMGIY | High mobility group protein, isoforms I and Y | DNA binding - transcriptional regulation - oncogene | Potential oncogene with MYC binding site at promoter region; involved in the transcription regulation of genes containing, or in close proximity to a + t-rich regions |
| HSPA1A | Heat shock 70 kD protein 1A | cell signalling and activation | AKA HSP-70, HSP70-1: Molecular chaperone, stabilizes AU rich mRNA |

TABLE 3-continued

Prostate Gene Expression Panel

| Symbol | Name | Classification | Description |
|---|---|---|---|
| IGF1R | Insulin-like growth factor 1 receptor | cytokines - chemokines - growth factors | Mediates insulin stimulated DNA synthesis; mediates IGF1 stimulated cell proliferation and differentiation |
| IL6 | Interleukin 6 | cytokines - chemokines - growth factors | Pro- and anti-inflammatory activity, TH2 cytokine, regulates hematopoiesis, activation of innate response, osteoclast development; elevated in sera of patients with metastatic cancer |
| IL8 | Interleukin 8 | cytokines - chemokines - growth factors | AKA SCYB8, MDNCF: Proinflammatory chemokine; major secondary inflammatory mediator resulting in cell adhesion, signal transduction, cell-cell signaling; regulates angiogenesis in prostate cancer |
| KAI1 | Kangai 1 | tumor suppressor | AKA SAR2, CD82, ST6: suppressor of metastatic ability of prostate cancer cells |
| KLK2 | Kallikrein 2, prostatic | protease - kallikrein | AKA hGK-1: Glandular kallikrein; expression restricted mainly to the prostate. |
| KLK3 | Kallikrein 3 | protease - kallikrein | AKA PSA: Kallikrein-like protease which functions normally in liquefaction of seminal fluid. Elevated in prostate cancer. |
| KRT19 | Keratin 19 | structural protein - differentiation | AKA K19: Type I epidermal keratin; may form intermediate filaments |
| KRT5 | Keratin 5 | structural protein - differentiation | AKA EBS2: 58 kD Type II keratin co-expressed with keratin 14, a 50 kD Type I keratin, in stratified epithelium. KRT5 expression is a hallmark of mitotically active keratinocytes and is the primary structural component of the 10 nm intermediate filaments of the mitotic epidermal basal cells. |
| KRT8 | Keratin 8 | structural protein - differentiation | AKA K8, CK8: Type II keratin; coexpressed with Keratin 18; involved in intermediate filament formation |
| LGALS8 | Lectin, Galactoside-binding, soluble 8 | cell adhesion - growth and differentiation | AKA PCTA-1: binds to beta galactoside; involved in biological processes such as cell adhesion, cell growth regulation, inflammation, immunomodulation, apoptosis and metastasis |
| MYC | V-myc avian myelocytomatosis viral oncogene homolog | transcription factor - oncogene | Transcription factor that promotes cell proliferation and transformation by activating growth-promoting genes; may also repress gene expression |
| NRP1 | Neuropilin 1 | cell adhesion | AKA NRP, VEGF165R: A novel VEGF receptor that modulates VEGF binding to KDR (VEGF receptor) and subsequent bioactivity and therefore may regulate VEGF-induced angiogenesis; calcium-independent cell adhesion molecule that function during the formation of certain neuronal circuits |

TABLE 3-continued

Prostate Gene Expression Panel

| Symbol | Name | Classification | Description |
|---|---|---|---|
| PART1 | Prostate androgen-regulated transcript 1 | | Exhibits increased expression in LNCaP cells upon exposure to androgens |
| PCA3 | Prostate cancer antigen 3 | | AKA DD3: prostate specific; highly expressed in prostate tumors |
| PCANAP7 | Prostate cancer associated protein 7 | | AKA IPCA7: unknown function; co-expressed with known prostate cancer genes |
| PDEF | Prostate epithelium specific Ets transcription factor | transcription factor | Acts as an androgen-independent transcriptional activator of the PSA promoter; directly interacts with the DNA binding domain of androgen receptor and enhances androgen-mediated activation of the PSA promoter |
| PLAU | Urokinase-type plasminogen activator | proteinase | AKA UPA, URK: cleaves plasminogen to plasmin |
| POV1 | Prostate cancer overexpressed gene 1 | | RNA expressed selectively in prostate tumor samples |
| PSCA | Prostate stem cell antigen | antigen | Prostate-specific cell surface antigen expressed strongly by both androgen-dependent and -independent tumors |
| PTGS2 | Prostaglandin-endoperoxide synthase 2 | cytokines - chemokines - growth factors | AKA COX-2: Proinflammatory; member of arachidonic acid to prostanoid conversion pathway |
| SERPINB5 | Serine proteinase inhibitor, clade B, member 5 | proteinase inhibitor - tumor suppressor | AKA Maspin, PI5: Protease Inhibitor; Tumor suppressor, especially for metastasis. |
| SERPINE1 | Serine (or cystein) proteinase inhibitor, clade E, member 1 | proteinase inhibitor | AKA PAI1: regulates fibrinolysis; inhibits PLAU |
| STAT3 | Signal transduction and activator of transcription 3 | transcription factor | AKA APRF: Transcription factor for acute phase response genes; rapidly activated in response to certain cytokines and growth factors; binds to IL6 response elements |
| TERT | Telomerase reverse transcriptase | | AKA TCS1, EST2: Ribonucleoprotein which in vitro recognizes a single-stranded G-rich telomere primer and adds multiple telomeric repeats to its 3-prime end by using an RNA template |
| TGFB1 | Transforming growth factor, beta 1 | cytokines - chemokines - growth factors | AKA DPD1, CED: Pro- and antiinflammatory activity; anti-apoptotic; cell-cell signaling, can either inhibit or stimulate cell growth |
| TNF | Tumor necrosis factor, member 2 | cytokines - chemokines - growth factors | AKA TNF alpha: Proinflammatory cytokine that is the primary mediator of immune response and regulation, associated with TH1 responses, mediates host response to bacterial stimuli, regulates cell growth & differentiation |
| TP53 | Tumor protein 53 | DNA binding protein - cell cycle - tumor suppressor | AKA P53: Activates expression of genes that inhibit tumor growth and/or invasion; involved in cell cycle regulation (required for growth arrest at G1); inhibits cell growth through activation of cell-cycle arrest and apoptosis |

TABLE 3-continued

Prostate Gene Expression Panel

| Symbol | Name | Classification | Description |
|---|---|---|---|
| VEGF | Vascular Endothelial Growth Factor | cytokines - chemokines - growth factors | AKA VPF: Induces vascular permeability, endothelial cell proliferation, angiogenesis |

TABLE 4

Skin Response Gene Expression Panel

| Symbol | Name | Classification | Description |
|---|---|---|---|
| BAX | BCL2 associated X protein | apoptosis induction-germ cell development | Accelerates programmed cell death by binding to and antagonizing the apoptosis repressor BCL2; may induce caspase activation |
| BCL2 | B-cell CLL/lymphoma 2 | apoptosis inhibitor - cell cycle control-oncogenesis | Integral mitochondrial membrane protein that blocks the apoptotic death of some cells such as lymphocytes; constitutive expression of BCL2 thought to be cause of follicular lymphoma |
| BSG | Basignin | signal transduction-peripheral plasma membrane protein | Member of Ig superfamily; tumor cell-derived collagenase stimulatory factor; stimulates matrix metalloproteinase synthesis in fibroblasts |
| COL7A1 | Type VII collagen, alpha 1 | collagen-differentiation-extracellular matrix | alpha 1 subunit of type VII collagen; may link collagen fibrils to the basement membrane |
| CRABP2 | Cellular Retinoic Acid Binding Protein | retinoid binding-signal transduction-transcription regulation | Low molecular weight protein highly expressed in skin; thought to be important in RA-mediated regulation of skin growth & differentiation |
| CTGF | Connective Tissue Growth Factor | insulin-like growth factor-differentiation-wounding response | Member of family of peptides including serum-induced immediate early gene products expressed after induction by growth factors; overexpressed in fibrotic disorders |
| DUSP1 | Dual Specificity Phosphatase | oxidative stress response-tyrosine phosphatase | Induced in human skin fibroblasts by oxidative/heat stress & growth factors; de-phosphorylates MAP kinase crk2; may play a role in negative regulation of cellular proliferation |
| FGF7 | Fibroblast growth factor 7 | growth factor-differentiation-wounding response-signal transduction | aka KGF; Potent mitogen for epithelial cells; induced after skin injury |
| FN1 | Fibronectin | cell adhesion - motility-signal transduction | Major cell surface glycoprotein of many fibroblast cells; thought to have a role in cell adhesion, morphology, wound healing & cell motility |
| FOS | v-fos FBJ murine osteosarcoma virus oncogene homolog | transcription factor-inflammatory response-cell growth & maintanence | Proto-oncoprotein acting with JUN, stimulates transcription of genes with AP-1 regulatory sites; in some cases FOS expression is associated with apototic cell death |
| GADD45A | Growth Arrest and DNA-damage-inducible alpha | cell cycle-DNA repair- | Transcriptionally induced following stressful growth arrest conditions & treatment with DNA damaging agents; binds to PCNA affecting it's interaction |

TABLE 4-continued

Skin Response Gene Expression Panel

| Symbol | Name | Classification | Description |
|---|---|---|---|
| GRO1 | GRO1 oncogene (melanoma growth stimulating activity, alpha) | apoptosis cytokines- chemokines- growth factors | with some cell division protein kinase AKA SCYB1; chemotactic for neutrophils |
| HMOX1 | Heme Oxygenase 1 | metabolism- endoplasmic reticulum | Essential enzyme in heme catabolism; HMOX1 induced by its substrate heme & other substances such as oxidizing agents & UVA |
| ICAM1 | Intercellular adhesion molecule 1 | Cell Adhesion/ Matrix Protein | Endothelial cell surface molecule; regulates cell adhesion and trafficking, upregulated during cytokine stimulation |
| IL1A | Interleukin 1, alpha | cytokines- chemokines- growth factors | Proinflammatory; constitutively and inducibly expressed in variety of cells. Generally cytosolic and released only during severe inflammatory disease |
| IL1B | Interleukin 1, beta | cytokines chemokines growth factors | Proinflammatory; constitutively and inducibly expressed by many cell types, secreted |
| 1L8 | Interleukin 8 | cytokines- chemokines- growth factors | Proinflammatory, major secondary inflammatory mediator, cell adhesion, signal transduction, cell-cell signaling, angiogenesis, synthesized by a wide variety of cell types |
| IVL | Involucrin | structural protein- peripheral plasma membrane protein | Component of the keratinocyte crosslinked envelope; first appears in the cytosol becoming crosslinked to membrane proteins by transglutaminase |
| JUN | v-jun avian sarcoma virus 17 oncogene homolog | transcription factor- DNA binding | Proto-oncoprotein; component of transcription factor AP-1 that interacts directly with target DNA sequences to regulate gene expression |
| KRT14 | Keratin 14 | structural protein- differentiation cell shape | Type I keratin; associates with keratin 5; component of intermediate filaments; several autosomal dominant blistering skin disorders caused by gene defects |
| KRT16 | Keratin 16 | structural protein- differentiation- cell shape | Type I keratin; component of intermediate filaments; induced in skin conditions favoring enhanced proliferation or abnormal differentiation |
| KRT5 | Keratin 5 | structural protein- differentiation- cell shape | Type II intermediate filament chain expressed largely in stratified epithelium; hallmark of mitotically active keratinocytes |
| MAPK8 | Mitogen Activated Protein Kinase 8 | kinase- stress response - signal transduction | aka JNK1; mitogen activated protein kinase regulates c-Jun in response to cell stress; UV irradiation of skin activates MAPK8 |
| MMP1 | Matrix Metalloproteinase 1 | Proteinase/ Proteinase Inhibitor | aka Collagenase; cleaves collagens types I–III; plays a key role in remodeling occuring in both normal & diseased conditions; transcriptionally regulated by growth factors, hormones, cytokines & cellular transformation |
| MMP2 | Matrix Metalloproteinase 2 | Proteinase/ Proteinase Inhibitor | aka Gelatinase; cleaves collagens types IV, V, VII and gelatin type I; produced by normal skin fibroblasts; may play a role in regulation of vascularization & the inflammatory response |
| MMP3 | Matrix Metalloproteinase 3 | Proteinase/ Proteinase Inhibitor | aka Stromelysin; degrades fibronectin, laminin, collagens III, IV, IX, X, cartilage proteoglycans, thought to be involved in wound repair; progression of atherosclerosis & tumor initiation; produced predominantly by connective tissue cells |

TABLE 4-continued

Skin Response Gene Expression Panel

| Symbol | Name | Classification | Description |
| --- | --- | --- | --- |
| MMP9 | Matrix metalloproteinase 9 | Proteinase/ Proteinase Inhibitor | AKA gelatinase B; degrades extracellular matrix molecules, secreted by IL-8-stimulated neutrophils |
| NR1I2 | Nuclear receptor subfamily 1 | transcription activation factor- signal transduction- xenobiotic metabolism | aka PAR2; Member of nuclear hormone receptor family of ligand-activated transcription factors; activates transcription of cytochrome P-450 genes |
| PCNA | Proliferating Cell Nuclear Antigen | DNA binding- DNA replication- DNA repair- cell proliferation | Required for both DNA replication & repair; processivity factor for DNA polymerases delta and epsilon |
| PI3 | Proteinase inhibitor 3 skin derived | proteinase inhibitor- protein binding- extracellular matrix | aka SKALP; Proteinase inhibitor found in epidermis of several inflammatory skin diseases; it's expression can be used as a marker of skin irritancy |
| PLAU | Plasminogen activator, urokinase | Proteinase/ Proteinase Inhibitor | AKA uPA; cleaves plasminogen to plasmin (a protease responsible for nonspecific extracellular matrix degradation) |
| PTGS2 | Prostaglandin-endoperoxide synthase 2 | Enzyme/ Redox | aka COX2; Proinflammatory, member of arachidonic acid to prostanoid conversion pathway; induced by proinflammatory cytokines |
| S100A7 | S100 calcium-binding protein 7 | calcium binding- epidermal differentiation | Member of S100 family of calcium binding proteins; localized in the cytoplasm &/or nucleus of a wide range of cells; involved in the regulation of cell cycle progression & differentiation; markedly overexpressed in skin lesions of psoriatic patients |
| TGFB1 | Transforming growth factor, beta | cytokines-chemokines-growth factors | Pro- and antiinflammatory activity, anti-apoptotic; cell-cell signaling, can either inhibit or stimulate cell growth |
| TIMP1 | Tissue Inhibitor of Matrix Metalloproteinase 1 | metalloproteinase inhibitor- ECM maintenance- positive control cell proliferation | Member of TIMP family; natural inhibitors of matrix metalloproteinases; transcriptionally induced by cytokines & hormones; mediates erythropoeisis in vitro |
| TNF | Tumor necrosis factor, alpha | cytokines-chemokines-growth factors | Proinflammatory, TH1, mediates host response to bacterial stimulus, regulates cell growth & differentiation |
| TNFSF6 | Tumor necrosis factor (ligand) superfamily, member 6 | ligand- apoptosis induction- signal transduction | aka FASL; Apoptosis antigen ligand 1 is the ligand for FAS; interaction of FAS with its ligand is critical in triggering apoptosis of some types of cells such as lymphocytes; defects in protein may be related to some cases of SLE |
| TP53 | tumor protein p53 | transcription factor- DNA binding- tumor suppressor- DNA recombination/ repair | Tumor protein p53, a nuclear protein, plays a role in regulation of cell cycle; binds to DNA p53 binding site and activates expression of downstream genes that inhibit growth and/or invasion of tumor |
| VEGF | vascular endothelial growth factor | cytokines-chemokines-growth factors | Producted by monocytes |

TABLE 5

Liver Metabolism and Disease Gene Expression Panel

| Symbol | Name | Classification | Description |
| --- | --- | --- | --- |
| ABCC1 | ATP-binding cassette, sub-family C, member 1 | Liver Health Indicator | AKA Multidrug resistance protein 1; AKA CFTR/MRP; multispecific organic anion membrane transporter; mediates drug resistance by pumping xenobiotics out of cell |
| AHR | Aryl hydrocarbon receptor | Metabolism Receptor/Transcription Factor | Increases expression of xenobiotic metabolizing enzymes (ie P450) in response to binding of planar aromatic hydrocarbons |
| ALB | Albumin | Liver Health Indicator | Carrier protein found in blood serum, synthesized in the liver, downregulation linked to decreased liver function/health |
| COL1A1 | Collagen, type 1, alpha 1 | Tissue Remodelling | AKA Procollagen; extracellular matrix protein; implicated in fibrotic processes of damaged liver |
| CYP1A1 | Cytochrome P450 1A1 | Metabolism Enzyme | Polycyclic aromatic hydrocarbon metabolism; monooxygenase |
| CYP1A2 | Cytochrome P450 1A2 | Metabolism Enzyme | Polycyclic aromatic hydrocarbon metabolism; monooxygenase |
| CYP2C19 | Cytochrome P450 2C19 | Metabolism Enzyme | Xenobiotic metabolism; monooxygenase |
| CYP2D6 | Cytochrome P450 2D6 | Metabolism Enzyme | Xenobiotic metabolism; monooxygenase |
| CYP2E | Cytochrome P450 2E1 | Metabolism Enzyme | Xenobiotic metabolism; monooxygenase; catalyzes formation of reactive intermediates from small organic molecules (i.e. ethanol, acetaminophen, carbon tetrachloride) |
| CYP3A4 | Cytochrome P450 3A4 | Metabolism Enzyme | Xenobiotic metabolism; broad catalytic specificity, most abundantly expressed liver P450 |
| EPHX1 | Epoxide hydrolase 1, microsomal (xenobiotic) | Metabolism Enzyme | Catalyzes hydrolysis of reactive epoxides to water soluble dihydrodiols |
| FAP | Fibroblast activation protein, □ | Liver Health Indicator | Expressed in cancer stroma and wound healing |
| GST | Glutathione S-transferase | Metabolism Enzyme | Catalyzes glutathione conjugation to metabolic substrates to form more water-soluble, excretable compounds; primer-probe set nonspecific for all members of GST family |
| GSTA1 and A2 | Glutathione S-transferase 1A1/2 | Metabolism Enzyme | Catalyzes glutathione conjugation to metabolic substrates to form more water-soluble, excretable compounds |
| GSTM1 | Glutathione S-transferase M1 | Metabolism Enzyme | Catalyzes glutathione conjugation to metabolic substrates to form more water-soluble, excretable |

TABLE 5-continued

Liver Metabolism and Disease Gene Expression Panel

| Symbol | Name | Classification | Description |
|---|---|---|---|
| KITLG | KIT ligand | Growth Factor | compounds<br>AKA Stem cell factor (SCF); mast cell growth factor, implicated in fibrosis/cirrhosis due to chronic liver inflammation |
| LGALS3 | Lectin, galactoside-binding, soluble, 3 | Liver Health Indicator | AKA galectin 3; Cell growth regulation |
| NR1I2 | Nuclear receptor subfamily 1, group I, family 2 | Metabolism Receptor/Transcription Factor | AKA Pregnane X receptor (PXR); heterodimer with retinoid X receptor forms nuclear transcription factor for CYP3A4 |
| NR1I3 | Nuclear receptor subfamily 1, group I, family 3 | Metabolism Receptor/Transcription Factor | AKA Constitutive androstane receptor beta (CAR); heterodimer with retinoid X receptor forms nuclear transcription factor; mediates P450 induction by phenobarbital-like inducers. |
| ORM1 | Orosomucoid 1 | Liver Health Indicator | AKA alpha 1 acid glycoprotein (AGP), acute phase inflammation protein |
| PPARA | Peroxisome proliferator activated receptor ☐ | Metabolism Receptor | Binds peroxisomal proliferators (ie fatty acids, hypolipidemic drugs) & controls pathway for beta-oxidation of fatty acids |
| SCYA2 | Small inducible cytokine A2 | Cytokine/Chemokine | AKA Monocyte chemotactic protein 1 (MCP1); recruits monocytes to areas of injury and infection, upregulated in liver inflammation |
| UCP2 | Uncoupling protein 2 | Liver Health Indicator | Decouples oxidative phosphorylation from ATP synthesis, linked to diabetes, obesity |
| UGT | UDP-Glucuronosyltransferase | Metabolism Enzyme | Catalyzes glucuronide conjugation to metabolic substrates, primer-probe set nonspecific for all members of UGT1 family |

TABLE 6

Endothelial Gene Expression Panel

| Symbol | Name | Classification | Description |
|---|---|---|---|
| ADAMTS1 | Disintegrin-like and metalloprotease (reprolysin type) with thrombospondin type 1 motif, 1 | Protease | AKA METH1; Inhibits endothelial cell proliferation; may inhibit angiogenesis; expression may be associated with development of cancer cachexia. |
| CLDN14 | Claudin 14 | | AKA DFNB29; Component of tight junction strands |
| ECE1 | Endothelin converting enzyme 1 | Metalloprotease | Cleaves big endothelin 1 to endothelin 1 |
| EDN1 | Endothelin 1 | Peptide hormone | AKA ET1; Endothelium-derived peptides; potent vasoconstrictor |

TABLE 6-continued

Endothelial Gene Expression Panel

| Symbol | Name | Classification | Description |
|---|---|---|---|
| EGR1 | Early growth response 1 | Transcription factor | AKA NGF1A; Regulates the transcription of genes involved in mitogenesis and differentiation |
| FLT1 | Fms-related tyrosine kinase 1 (vascular endothelial growth factor/vascular permeability factor receptor) | | AKA VEGFR1; FRT; Receptor for VEGF; involved in vascular development and regulation of vascular permeability |
| GJA1 | gap junction protein, alpha 1, 43 kD | | AKA CX43; Protein component of gap junctions; major component of gap junctions in the heart; may be important in synchronizing heart contractions and in embryonic development |
| GSR | Glutathione reductase 1 | Oxidoreductase | AKA GR; GRASE; Maintains high levels of reduced glutathione in the cytosol |
| HIF1A | Hypoxia-inducible factor 1, alpha subunit | Transcription factor | AKA MOP1; ARNT interacting protein; mediates the transcription of oxygen regulated genes; induced by hypoxia |
| HMOX1 | Heme oxygenase (decycling) 1 | Redox Enzyme | AKA HO1; Essential for heme catabolism, cleaves heme to form biliverdin and CO; endotoxin inducible |
| ICAM1 | Intercellular adhesion molecule 1 | Cell Adhesion/ Matrix Protein | Endothelial cell surface molecule; regulates cell adhesion and trafficking upregulated during cytokine stimulation |
| IGFBP3 | Insulin-like growth factor binding protein 3 | | AKA IBP3; Expressed by vascular endothelial cells; may influence insulin-like growth factor activity |
| IL15 | Interleukin 15 | cytokines-chemokines-growth factors | Proinflammatory; mediates T-cell activation, inhibits apoptosis, synergizes with IL-2 to induce IFN-g and TNF-a |
| IL1B | Interleukin 1, beta | cytokines-chemokines-growth factors | Proinflammatory; constitutively and inducibly expressed by many cell types, secreted |
| IL8 | Interleukin 8 | cytokines-chemokines-growth factors | Proinflammatory, major secondary inflammatory mediator, cell adhesion. signal transduction, cell-cell signaling angiogenesis, synthesized by a wide variety of cell types |
| MAPK1 | mitogen-activated protein kinase 1 | Transferase | AKA ERK2; May promote entry into the cell cycle, growth factor responsive |
| NFKB1 | Nuclear Factor kappa B | Transcription Factor | AKA KBF1, EBP1; Transcription factor that regulates the expression of infolammatory and immune genes; central role in Cytokine induced expression of E-selectin |
| NOS2A | Nitric oxide synthase 2A | Enzyme/Redox | AKA iNOS; produces NO which is bacteriocidal/tumoricidal |
| NOS3 | EndothelialNitric Oxide Synthase | | AKA ENOS, CNOS; Synthesizes nitric oxide from oxygen and arginine; nitric oxide is implicated in vascular smooth muscle relaxation, vascular endothelial growth factor induced angiogenesis, and blood clotting through the activation of platelets |
| PLAT | Plasminogen activator, tissue | Protease | AKA TPA; Converts plasminogin to plasmin; involved in fibrinolysis and cell migration |
| PTGIS | Prostaglandin I2 (prostacyclin) synthase | Isomerase | AKA PGIS; PTG1; CYP8; CYP8A1; Converts prostaglandin h2 to prostacyclin (vasodilator); cytochrome P450 family; imbalance of prostacyclin may contribute to myocardial infarction, stroke, atherosclerosis |
| PTGS2 | Prostaglandin-endoperoxide synthase 2 | Enzyme/Redox | AKA COX2; Proinflammatory, member of arachidonic acid to prostanoid conversion pathway; induced by proinflammatory cytokines |

TABLE 6-continued

Endothelial Gene Expression Panel

| Symbol | Name | Classification | Description |
|---|---|---|---|
| PTX3 | pentaxin-related gene, rapidly induced by IL-1 beta | | AKA TSG-14; Pentaxin 3; Similar to the pentaxin subclass of inflammatory acute-phase proteins; novel marker of inflammatory reactions |
| SELE | selectin E (endothelial adhesion molecule 1) | Cell Adhesion | AKA ELAM; Expressed by cytokine-stimulated endothelial cells; mediates adhesion of neutrophils to the vascular lining |
| SERPINE1 | Serine (or cysteine) protease inhibitor, clade B (ovalbumin), member 1 | Proteinase Inhibitor | AKA PAI1; Plasminogen activator inhibitor type 1; interacts with tissue plasminogen activator to regulate fibrinolysis |
| TEK | tyrosine kinase, endothelial | Transferase Receptor | AKA TIE2, VMCM; Receptor for angiopoietin-1; may regulate endothelial cell proliferation and differentiation; involved in vascular morphogenesis; TEK defects are associated with venous malformations |
| VCAM1 | vascular cell adhesion molecule 1 | Cell Adhesion/ Matrix Protein | AKA L1CAM; CD106; INCAM-100; Cell surface adhesion molecule specific for blood leukocytes and some tumor cells; mediates signal transduction; may be linked to the development of atherosclerosis, and rheumatoid arthritis |
| VEGF | Vascular Endothelial Growth Factor | Growth factor | AKA VPF; Induces vascular permeability and endothelial cell growth; associated with angiogenesis |

TABLE 7

Cell Health and Apoptosis Gene Expression Panel

| Symbol | Name | Classification | Description |
|---|---|---|---|
| ABL1 | V-abl Abelson murine leukemia viral oncogene homolog 1 | oncogene | Cytoplasmic and nuclear protein tyrosine kinase implicated in cell differentiation, division, adhesion and stress response. Alterations of ABL1 lead to malignant transformations. |
| APAF1 | Apoptotic Protease Activating Factor 1 | protease activator | Cytochrome c binds to APAF1, triggering activation of CASP3, leading to apoptosis. May also facilitate procaspase 9 autoactivation. |
| BAD | BCL2 Agonist of Cell Death | membrane protein | Heterodimerizes with BCLX and counters its death repressor activity. This displaces BAX and restores its apoptosis-inducing activity. |
| BAK1 | BCL2-antagonist/killer 1 | membrane protein | In the presence of an apropriate stimulus BAK 1 accelerates programed cell death by binding to, and antagonizing the repressor BCL2 or its adenovirus homolog e1b 19 k protein. |
| BAX | BCL2-associated X protein | membrane protein | Accelerates apoptosis by binding to, and antagonizing BCL2 or its adenovirus homolog e1b 19 k protein. It induces the release of cytochrome c and activation of CASP3 |
| BCL2 | B-cell CLL/lymphoma 2 | membrane protein | Interferes with the activation of caspases by preventing the release of cytochrome c, thus blocking apoptosis. |
| BCL2L1 | BCL2-like 1 (long form) | membrane protein | Dominant regulator of apoptotic cell death. The long |

TABLE 7-continued

Cell Health and Apoptosis Gene Expression Panel

| Symbol | Name | Classification | Description |
| --- | --- | --- | --- |
| | | | form displays cell death repressor activity, whereas the short isoform promotes apoptosis. BCL2L1 promotes cell survival by regulating the electrical and osmotic homeostasis of mitochondria. |
| BID | BH3-Interacting Death Domain Agonist | | Induces ice-like proteases and apoptosis. counters the protective effect of bcl-2 (by similarity). Encodes a novel death agonist that heterodimerizes with either agonists (BAX) or antagonists (BCL2). |
| BIK | BCL2-Interacting Killer | | Accelerates apoptosis. Binding to the apoptosis repressors BCL2L1, bhrf1, BCL2 or its adenovirus homolog e1b 19 k protein suppresses this death-promoting activity. |
| BIRC2 | Baculoviral IAP Repeat-Containing 2 | apoptosis suppressor | May inhibit apoptosis by regulating signals required for activation of ICE-like proteases. Interacts with TRAF1 and TRAF2. Cytoplasmic |
| BIRC3 | Baculoviral IAP Repeat-Containing 3 | apoptosis suppressor | Apoptotic suppressor. Interacts with TRAF1 and TRAF2. Cytoplasmic |
| BIRC5 | Survivin | apoptosis suppressor | Inhibits apoptosis. Inhibitor of CASP3 and CASP7. Cytoplasmic |
| CASP1 | Caspase 1 | proteinase | Activates IL1B; stimulates apoptosis |
| CASP3 | Caspase 3 | proteinase | Involved in activation cascade of caspases responsible for apoptosis - cleaves CASP6, CASP7, CASP9 |
| CASP9 | Caspase 9 | proteinase | Binds with APAF1 to become activated; cleaves and activates CASP3 |
| CCNA2 | Cyclin A2 | cyclin | Drives cell cycle at G1/S and G2/M phase; interacts with cdk2 and cdc2 |
| CCNB1 | Cyclin B1 | cyclin | Drives cell cycle at G2/M phase; complexes with cdc2 to form mitosis promoting factor |
| CCND1 | Cyclin D1 | cyclin | Controls cell cycle at G1/S (start) phase; interacts with cdk4 and cdk6; has oncogene function |
| CCND3 | Cyclin D3 | cyclin | Drives cell cycle at G1/S phase; expression rises later in G1 and remains elevated in S phase; interacts with cdk4 and cdk6 |
| CCNE1 | Cyclin E1 | cyclin | Drives cell cycle at G1/S transition; major downstream target of CCND1; cdk2-CCNE1 activity required for centrosome duplication during S phase; interacts with RB |
| cdk2 | Cyclin-dependent kinase 2 | kinase | Associated with cyclins A, D and E; activity maximal during S phase and G2; CDK2 activation, through caspase-mediated cleavage of CDK inhibitors, may be instrumental in the execution of apoptosis following caspase activation |

TABLE 7-continued

Cell Health and Apoptosis Gene Expression Panel

| Symbol | Name | Classification | Description |
| --- | --- | --- | --- |
| cdk4 | Cyclin-dependent kinase 4 | kinase | cdk4 and cyclin-D type complexes are responsible for cell proliferation during G1; inhibited by CDKN2A (p16) |
| CDKN1A | Cyclin-Dependent Kinase Inhibitor 1A (p21) | tumor suppressor | May bind to and inhibit cyclin-dependent kinase activity, preventing phosphorylation of critical cyclin-dependent kinase substrates and blocking cell cycle progression; activated by p53; tumor suppressor function |
| CDKN2B | Cyclin-Dependent Kinase Inhibitor 2B (p15) | tumor suppressor | Interacts strongly with cdk4 and cdk6; role in growth regulation but limited role as tumor suppressor |
| CHEK1 | Checkpoint, S. pombe | | Involved in cell cycle arrest when DNA damage has occurred, or unligated DNA is present; prevents activation of the cdc2-cyclin b complex |
| DAD1 | Defender Against Cell Death | membrane protein | Loss of DAD1 protein triggers apoptosis |
| DFFB | DNA Fragmentation Factor, 40-KD, Beta Subunit | nuclease | Induces DNA fragmentation and chromatin condensation during apoptosis; can be activated by CASP3 |
| FADD | Fas (TNFRSF6)-associated via death domain | co-receptor | Apoptotic adaptor molecule that recruits caspase-8 or caspase-10 to the activated fas (cd95) or tnfr-1 receptors; this death-inducing signalling complex performs CASP8 proteolytic activation |
| GADD45A | Growth arrest and DNA damage inducible, alpha | regulator of DNA repair | Stimulates DNA excision repair in vitro and inhibits entry of cells into S phase; binds PCNA |
| K-ALPHA-1 | Alpha Tubulin, ubiquitous | microtubule peptide | Major constituent of microtubules; binds 2 molecules of GTP |
| MADD | MAP-kinase activating death domain | co-receptor | Associates with TNFR1 through a death domain-death domain interaction; Overexpression of MADD activates the MAP kinase ERK2, and expression of the MADD death domain stimulates both the ERK2 and JNK1 MAP kinases and induces the phosphorylation of cytosolic phospholipase A2 |
| MAP3K14 | Mitogen-activated protein kinase kinase kinase 14 | kinase | Activator of NFKB1 |
| MRE11A | Meiotic recombination (S. cerevisiae) 11 homolog A | nuclease | Exonuclease involved in DNA double-strand breaks repair |
| NFKB1 | Nuclear factor of kappa light polypeptide gene enhancer in B-cells 1 (p105) | nuclear translational regulator | p105 is the precursor of the p50 subunit of the nuclear factor NFKB, which binds to the kappa-b consensus sequence located in the enhancer region of genes involved in immune response and acute phase reactions; the precursor does not bind DNA itself |
| PDCD8 | Programmed Cell Death 8 (apoptosis-inducing factor) | enzyme, reductase | The principal mitochondrial factor causing nuclear apoptosis. Independent of caspase apoptosis. |
| PNKP | Polynucleotide kinase 3'-phosphatase | phosphatase | Catalyzes the 5-prime phosphorylation of nucleic acids and can have associated 3-prime phosphatase activity, predictive of an important |

TABLE 7-continued

Cell Health and Apoptosis Gene Expression Panel

| Symbol | Name | Classification | Description |
|---|---|---|---|
| PTEN | Phosphatase and tensin homolog (mutated in multiple advanced cancers 1) | tumor suppressor | function in DNA repair following ionizing radiation or oxidative damage Tumor suppressor that modulates G1 cell cycle progression through negatively regulating the PI3-kinase/Akt signaling pathway; one critical target of this signaling process is the cyclin-dependent kinase inhibitor p27 (CDKN1B). |
| RAD52 | RAD52 (S. cerevisiae) homolog | DNA binding proteinsor | Involved in DNA double-stranded break repair and meiotic/mitotic recombination |
| RB1 | Retinoblastoma 1 (including osteosarcoma) | tumor suppressor | Regulator of cell growth; interacts with E2F-like transcription factor; a nuclear phosphoprotein with DNA binding activity; interacts with histone deacetylase to repress transcription |
| SMAC | Second mitochondria-derived activator of caspase | mitochondrial peptide | Promotes caspase activation in cytochrome c/APAF-1/caspase 9 pathway of apoptosis |
| TERT | Telomerase reverse transcriptase | transcriptase | Ribonucleoprotein which in vitro recognizes a single-stranded G-rich telomere primer and adds multiple telomeric repeats to its 3-prime end by using an RNA template |
| TNF | Tumor necrosis factor | cytokines-chemokines-growth factors | Proinflammatory, TH1, mediates host response to bacterial stimulus, regulates cell growth & differentiation |
| TNFRSF11A | Tumor necrosis factor receptor superfamily, member 11a, activator of NFKB | receptor | Activates NFKB1; Important regulator of interactions between T cells and dendritic cells |
| TNFRSF12 | Tumor necrosis factor receptor superfamily, member 12 (translocating chain-association membrane protein) | receptor | Induces apoptosis and activates NF-kappaB; contains a cytoplasmic death domain and transmembrane domains |
| TOSO | Regulator of Fas-induced apoptosis | receptor | Potent inhibitor of Fas induced apoptosis; expression of TOSO, like that of FAS and FASL, increases after T-cell activation, followed by a decline and susceptibility to apoptosis; hematopoietic cells expressing TOSO resist anti-FAS-, FADD-, and TNF-induced apoptosis without increasing expression of the inhibitors of apoptosis BCL2 and BCLXL; cells expressing TOSO and activated by FAS have reduced CASP8 and increased CFLAR expression, which inhibits CASP8 processing |
| TP53 | Tumor Protein 53 | DNA binding protein - cell cycle - tumor suppressor | Activates expression of genes that inhibit tumor growth and/or invasion; involved in cell cycle regulation (required for growth arrest at G1); inhibits cell growth through activation of cell-cycle arrest and apoptosis |
| TRADD | TNFRSF1A-associated via death domain | co-receptor | Overexpression of TRADD leads to 2 major TNF-induced responses, apoptosis and activation of NE-kappa-B |
| TRAF1 | TNF receptor-associated factor 1 | co-receptor | Interact with cytoplasmic domain of TNFR2 |

TABLE 7-continued

Cell Health and Apoptosis Gene Expression Panel

| Symbol | Name | Classification | Description |
| --- | --- | --- | --- |
| TRAF2 | TNF receptor-associated factor 2 | co-receptor | Interact with cytoplasmic domain of TNFR2 |
| VDAC1 | Voltage-dependent anion channel 1 | membrane protein | Functions as a voltage-gated pore of the outer mitochondrial membrane; proapoptotic proteins BAX and BAK accelerate the opening of VDAC allowing cytochrome c to enter, whereas the antiapoptotic protein BCL2L1 closes VDAC by binding directly to it |
| XRCC5 | X-ray repair complementing defective repair in Chinese hamster cells 5 | helicase | Functions together with the DNA ligase IV-XRCC4 complex in the repair of DNA double-strand breaks |

TABLE 8

Cytokine Gene Expression Panel

| Symbol | Name | Classification | Description |
| --- | --- | --- | --- |
| CSF3 | Colony Stimulating Factor 3 (Granulocyte) | Cytokines/Chemokines/Growth Factors | AKA G-CSF; Cytokine that stimulates granulocyte development |
| IFNG | Interferon, Gamma | Cytokines/Chemokines/Growth Factors | Pro- and antiinflammatory activity; TH1 cytokine; nonspecific inflammatory mediator; produced by activated T-cells. Antiproliferative effects on transformed cells. |
| IL1A | Interleukin 1, Alpha | Cytokines/Chemokines/Growth Factors | Proinflammatory; constitutively and inducibly expressed in variety of cells. Generally cytosolic and released only during severe inflammatory disease |
| IL1B | Interleukin 1, Beta | Cytokines/Chemokines/Growth Factors | Proinflammatory; constitutively and inducibly expressed by many cell types, secreted |
| IL1RN | Interleukin 1 Receptor Antagonist | Cytokines/Chemokines/Growth Factors | IL1 receptor antagonist; Antiinflammatory; inhibits binding of IL-1 to IL-1 receptor by binding to receptor without stimulating IL-1-like activity |
| IL2 | Interleukin 2 | Cytokines/Chemokines/Growth Factors | T-cell growth factor, expressed by activated T-cells, regulates lymphocyte activation and differentiation; inhibits apoptosis, TH1 cytokine |
| IL4 | Interleukin 4 | Cytokines/Chemokines/Growth Factors | Antiinflammatory; TH2; suppresses proinflammatory cytokines, increases expression of IL-1RN, regulates lymphocyte activation |
| IL5 | Interleukin 5 | Cytokines/Chemokines/Growth Factors | Eosinophil stimulatory factor; stimulates late B cell differentiation to secretion of Ig |
| IL6 | Interleukin 6 | Cytokines/Chemokines/Growth Factors | AKA Interferon, Beta 2; Pro- and anti-inflammatory activity, $TH_2$ cytokine, regulates hematopoiesis, activation of innate response, osteoclast development; elevated in sera of patients with metastatic cancer |

TABLE 8-continued

Cytokine Gene Expression Panel

| Symbol | Name | Classification | Description |
|---|---|---|---|
| IL10 | Interleukin 10 | Cytokines/Chemokines/Growth Factors | Antiinflammatory; $TH_2$; Suppresses production of proinflammatory cytokines |
|  | Interleukin 12 (p40) | Cytokines/Chemokines/Growth Factors | Proinflammatory; mediator of innate immunity, $TH_1$ cytokine, requires co-stimulation with IL-18 to induce IFN-y |
| IL13 | Interleukin 13 | Cytokines/Chemokines/Growth Factors | Inhibits inflammatory cytokine production |
| IL15 | Interleukin 15 | Cytokines/Chemokines/Growth Factors | Proinflammatory; mediates T-cell activation, inhibits apoptosis, synergizes with IL-2 to induce IFN-g and TNF-a |
| IL18 | Interleukin 18 | Cytokines/Chemokines/Growth Factors | Proinflammatory, TH1, innate and aquired immunity, promotes apoptosis, requires co-stimulation with IL-1 or IL-2 to induce TH1 cytokines in T- and NK-cells |
| IL18BP | IL-18 Binding Protein | Cytokines/Chemokines/Growth Factors | Implicated in inhibition of early TH1 cytokine responses |
| TGFA | Transforming Growth Factor, Alpha | Transferase/Signal Transduction | Proinflammatory cytokine that is the primary mediator of immune response and regulation, Associated with $TH_1$ responses, mediates host response to bacterial stimuli, regulates cell growth & differentiation; Negative regulation of insulin action |
| TGFB1 | Transforming Growth Factor, Beta 1 | Cytokines/Chemokines/Growth Factors | AKA DPD1, CED; Pro- and antiinflammatory activity; Anti-apoptotic; cell-cell signaling, Can either inhibit or stimulate cell growth; Regulated by glucose in NIDDM individuals, overexpression (due to oxidative stresS promotes renal cell hypertrophy leading to diabetic nephropathy |
| TNFSF5 | Tumor Necrosis Factor (Ligand) Superfamily, Member 5 | Cytokines/Chemokines/Growth Factors | Ligand for CD40; Expressed on the surface of T-cells; Regulates B-cell function by engaging CD40 on the B-cell surface |
| TNFSF6 | Tumor Necrosis Factor (Ligand) Superfamily, Member 6 | Cytokines/Chemokines/Growth Factors | AKA FASL; Apoptosis antigen ligand 1 is the ligand for FAS antigen; Critical in triggering apoptosis of some types of cells such as lymphocytes; Defects in protein may be related to some cases of SLE |
| TNFSF13B | Tumor Necrosis Factor (Ligand) Superfamily, Member 13B | Cytokines/Chemokines/Growth Factors | B-cell activating factor, TNF family |

TABLE 9

TNF/IL1 Inhibition Gene Expression Panel

| HUGO Symbol | Name | Classification | Description |
|---|---|---|---|
| CD14 | CD14 Antigen | Cell Marker | LPS receptor used as marker for monocytes |
| GRO1 | GRO1 Oncogene | Cytokines/Chemokines/Growth factors | AKA SCYB1, Melanoma growth stimulating activity, |

TABLE 9-continued

TNF/IL1 Inhibition Gene Expression Panel

| HUGO Symbol | Name | Classification | Description |
|---|---|---|---|
| | | | Alpha; Chemotactic for neutrophils |
| HMOX1 | Heme Oxygenase (Decycling) 1 | Enzyme: Redox | Enzyme that cleaves heme to form biliverdin and CO; Endotoxin inducible |
| ICAM1 | Intercellular Adhesion Molecule 1 | Cell Adhesion: Matrix Protein | Endothelial cell surface molecule; Regulates cell adhesion and trafficking; Up-regulated during cytokine stimulation |
| IL1B | Interleukin 1, Beta | Cytokines/Chemokines/ Growth factors | Pro-inflammatory; Constitutively and inducibly expressed by many cell types; Secreted |
| IL1RN | Interleukin 1 Receptor Antagonist | Cytokines/Chemokines/ Growth factors | Anti-inflammatory; Inhibits binding of IL-1 to IL-1 receptor by binding to receptor without stimulating IL-1-like activity |
| IL10 | Interleukin 10 | Cytokines/Chemokines/ Growth factors | Anti-inflammatory; $TH_2$ cytokine; Suppresses production of pro-inflammatory cytokines |
| MMP9 | Matrix Metalloproteinase 9 | Proteinase/Proteinase Inhibitor | AKA Gelatinase B; Degrades extracellular matrix molecules; Secreted by IL-8 stimulated neutrophils |
| SERPINE1 | Serine (or Cysteine) Protease Inhibitor, Clade E (Ovalbumin), Member 1 | Proteinase/Proteinase Inhibitor | AKA Plasminogen activator inhibitor-1, PAI-1; Regulator of fibrinolysis |
| TGFB1 | Transforming Growth Factor, Beta 1 | Cytokines/Chemokines/ Growth factors | Pro- and anti-inflammatory activity; Anti-apoptotic; Cell-cell signaling; Can either inhibit or stimulate cell growth |
| TIMP1 | Tissue Inhibitor of Metalloproteinase 1 | Proteinase/Proteinase Inhibitor | Irreversibly binds and inhibits metalloproteinases such as collagenase |
| TNFA | Tumor Necrosis Factor, Alpha | Cytokines/Chemokines/ Growth factors | Pro-inflammatory; $TH_1$ cytokine; Mediates host response to bacterial stimulus; Regulates cell growth & differentiation |

TABLE 10

Chemokine Gene Expression Panel

| Symbol | Name | Classification | Description |
|---|---|---|---|
| CCR1 | chemokine (C-C motif) receptor 1 | Chemokine receptor | A member of the beta chemokine receptor family (seven transmembrane protein). Binds SCYA3/MIP-1a, SCYA5/RANTES, MCP-3, HCC-1, 2, and 4, and MPIF-1. Plays role in dendritic cell migration to inflammation sites and recruitment of monocytes. |
| CCR3 | chemokine (C-C motif) receptor 3 | Chemokine receptor | C-C type chemokine receptor (Eotaxin receptor) binds to Eotaxin, Eotaxin-3, MCP-3, MCP-4, SCYA5/RANTES and mip-1 delta thereby mediating intracellular calcium flux. Alternative co-receptor with CD4 for HIV-1 infection. Involved in recruitment of eosinophils. Primarily a Th2 cell chemokine receptor. |
| CCR5 | chemokine (C-C motif) receptor 5 | Chemokine receptor | Member of the beta chemokine receptor family (seven |

TABLE 10-continued

Chemokine Gene Expression Panel

| Symbol | Name | Classification | Description |
| --- | --- | --- | --- |
| | | | transmembrane protein). Binds to SCYA3/MIP-1a and SCYA5/RANTES. Expressed by T cells and macrophages, and is an important co-receptor for macrophage-tropic virus, including HIV, to enter host cells. Plays a role in Th1 cell migration. Defective alleles of this gene have been associated with the HIV infection resistance. |
| CX3CR1 | chemokine (C-X3-C) receptor 1 | Chemokine receptor | CX3CR1 is an HIV coreceptor as well as a leukocyte chemotactic/adhesion receptor for fractalkine. Natural killer cells predominantly express CX3CR1 and respond to fractalkine in both migration and adhesion. |
| CXCR4 | chemokine (C-X-C motif), receptor 4 (fusin) | Chemokine receptor | Receptor for the CXC chemokine SDF1. Acts as a co-receptor with CD4 for lymphocyte-tropic HIV-1 viruses. Plays role in B cell, Th2 cell and naive T cell migration. |
| GPR9 | G protein-coupled receptor 9 | Chemokine receptor | CXC chemokine receptor binds to SCYB10/IP-10, SCYB9/MIG, SCYB11/I-TAC. Binding of chemokines to GPR9 results in integrin activation, cytoskeletal changes and chemotactic migration. Prominently expressed in in vitro cultured effector/memory T cells and plays a role in Th1 cell migration. |
| GRO1 | GRO1 oncogene (melanoma growth stimulating activity, alpha) | Chemokine | AKA SCYB1; chemotactic for neutrophils. GRO1 is also a mitogenic polypeptide secreted by human melanoma cells. |
| GRO2 | GRO2 oncogene (MIP-2) | Chemokine | AKA MIP2, SCYB2; Macrophage inflammatory protein produced by moncytes and neutrophils. Belongs to intercrine family alpha (CXC chemokine). |
| IL8 | interleukin 8 | Chemokine | Proinflammatory, major secondary inflammatory mediator, cell adhesion, signal transduction, cell-cell signaling, angiogenesis, synthesized by a wide variety of cell types |
| PF4 | Platelet Factor4 (SCYB4) | Chemokine | PF4 is released during platelet aggregation and is chemotactic for neutrophils and monocytes. PF4's major physiologic role appears to be neutralization of heparin-like molecules on the endothelial surface of blood vessels, thereby inhibiting local antithrombin III activity and promoting coagulation. |
| SCYA2 | small inducible cytokine A2 (MCP1) | Chemokine | Recruits monocytes to areas of injury and infection. Stimulates IL-4 production; implicated in diseases involving monocyte, basophil infiltration of tissue (ie.g., psoriasis, rheumatoid arthritis, atherosclerosis). |

TABLE 10-continued

Chemokine Gene Expression Panel

| Symbol | Name | Classification | Description |
|---|---|---|---|
| SCYA3 | small inducible cytokine A3 (MIP1a) | Chemokine | A "monokine" involved in the acute inflammatory state through the recruitment and activation of polymorphonuclear leukocytes. A major HIV-suppressive factor produced by CD8-positive T cells. |
| SCYA5 | small inducible cytokine A5 (RANTES) | Chemokine | Binds to CCR1, CCR3, and CCR5 and is a chemoattractant for blood monocytes, memory t helper cells and eosinophils. A major HIV-suppressive factor produced by CD8-positive T cells. |
| SCYB10 | small inducible cytokine subfamily B (Cys-X-Cys), member 10 | Chemokine | A CXC subfamily chemokine. Binding of SCYB10 to receptor CXCR3/GPR9 results in stimulation of monocytes, natural killer and T-cell migration, and modulation of adhesion molecule expression. SCYB10 is Induced by IFNg and may be a key mediator in IFNg response. |
| SDF1 | stromal cell-derived factor 1 | Chemokine | Belongs to the CXC subfamily of the intercrine family, which activate leukocytes. SDF1 is the primary ligand for CXCR4, a coreceptor with CD4 for human immunodeficiency virus type 1 (HIV-1). SDF1 is a highly efficacious lymphocyte chemoattractant. |

TABLE 11

Breast Cancer Gene Expression Panel

| Symbol | Name | Classification | Description |
|---|---|---|---|
| ACTB | Actin, beta | Cell Structure | Actins are highly conserved proteins that are involved in cell motility, structure and integrity. ACTB is one of two non-muscle cytoskeletal actins. Site of action for cytochalasin B effects on cell motility. |
| BCL2 | B-cell CLL/lymphoma 2 | membrane protein | Interferes with the activation of caspases by preventing the release of cytochrome c, thus blocking apoptosis. |
| CD19 | CD19 antigen | Cell Marker | AKA Leu 12; B cell growth factor |
| CD34 | CD34 antigen | Cell Marker | AKA: hematopoietic progenitor cell antigen. Cell surface antigen selectively expressed on human hematopoietic progenitor cells. Endothelial marker. |
| CD44 | CD44 antigen | Cell Marker | Cell surface receptor for hyaluronate. Probably involved in matrix adhesion, lymphocyte activation and lymph node homing. |
| DC13 | DC13 protein | | unknown function |
| DSG1 | Desmoglein 1 | membrane protein | Calcium-binding transmembrane glycoprotein involved in the interaction of plaque proteins and intermediate filaments mediating cell-cell adhesion. Interact with cadherins. |
| EDR2 | Early Development | | The specific function in human cells has not yet been determined. |

TABLE 11-continued

Breast Cancer Gene Expression Panel

| Symbol | Name | Classification | Description |
| --- | --- | --- | --- |
| | Regulator 2 | | May be part of a complex that may regulate transcription during embryonic development. |
| ERBB2 | v-erb-b2 erythroblastic leukemia viral oncogene homolog 2 | Oncogene | Oncogene. Overexpression of ERBB2 confers Taxol resistance in breast cancers. Belongs to the EGF tyrosine kinase receptor family. Binds gp130 subunit of the IL6 receptor in an IL6 dependent manner. An essential component of IL-6 signalling through the MAP kinase pathway. |
| ERBB3 | v-erb-b2 Erythroblastic Leukemia Viral Oncogene Homolog 3 | Oncogene | Oncogene. Overexpressed in mammary tumors. Belongs to the EGF tyrosine kinase receptor family. Activated through neuregulin and ntak binding. |
| ESR1 | Estrogen Receptor 1 | Receptor/ Transcription Factor | ESR1 is a ligand-activated transcription factor composed of several domains important for hormone binding, DNA binding, and activation of transcription. |
| FGF18 | Fibroblast Growth Factor 18 | Growth Factor | Involved in a variety of biological processes, including embryonic development, cell growth, morphogenesis, tissue repair, tumor growth, and invasion. |
| FLT1 | Fms-related tyrosine kinase 1 | Receptor | Receptor for VEGF; involved in vascular development and regulation of vascular permeability. |
| FOS | V-fos FBJ murine osteosarcoma viral oncogene homolog | Oncogene/ Transcriptional Activator | Leucine zipper protein that forms the transcription factor AP-1 by dimerizing with JUN. Implicated in the processes of cell proliferation, differentiation, transformation, and apoptosis. |
| GRO1 | GRO1 oncogene | Chemokine/Growth Factor/Oncogene | Proinflammatory; chemotactic for neutrophils. Growth regulator that modulates the expression of metalloproteinase activity. |
| IFNG | Interferon, gamma | Cytokine | Pro- and antiinflammatory activity; TH1 cytokine; nonspecific inflammatory mediator; produced by activated T-cells. Antiproliferative effects on transformed cells. |
| IRF5 | Interferon regulatory factor 5 | Transcription Factor | Regulates transcription of interferon genes through DNA sequence-specific binding. Diverse roles, include virus-mediated activation of interferon, and modulation of cell growth, differentiation, apoptosis, and immune system activity. |
| KRT14 | Keratin 14 | Cytoskeleton | Type I keratin, intermediate filament component; KRT14 is detected in the basal layer, with lower expression in more apical layers, and is not present in the stratum corneum. Together with KRT5 forms the cytoskeleton of epithelial cells. |
| KRT19 | Keratin 19 | Cytoskeleton | Type I epidermal keratin; may form intermediate filaments. Expressed often in epithelial cells in culture and in some carcinomas |
| KRT5 | Keratin 5 | Cytoskeleton | Coexpressed with KRT14 to form cytoskeleton of epithelial cells. KRT5 expression is a hallmark of mitotically active keratinocytes and is the primary structural component of the 10 nm intermediate filaments of the mitotic epidermal basal cells. |

TABLE 11-continued

Breast Cancer Gene Expression Panel

| Symbol | Name | Classification | Description |
|---|---|---|---|
| MDM2 | Mdm2, transformed 3T3 cell double minute 2, p53 binding protein | Oncogene/ Transcription Factor | Inhibits p53- and p73-mediated cell cycle arrest and apoptosis by binding its transcriptional activation domain, resulting in tumorigenesis. Permits the nuclear export of p53 and targets it for proteasome-mediated proteolysis. |
| MMP9 | Matrix metalloproteinase 9 | Proteinase/ Proteinase Inhibitor | Degrades extracellular matrix by cleaving types IV and V collagen. Implicated in arthritis and metastasis. |
| MP1 | Metalloprotease 1 | Proteinase/ Proteinase Inhibitor | Member of the pitrilysin family. A metalloendoprotease. Could play a broad role in general cellular regulation. |
| N33 | Putative prostate cancer tumor suppressor | Tumor Suppressor | Integral membrane protein. Associated with homozygous deletion in metastatic prostate cancer. |
| OXCT | 3-oxoacid CoA transferase | Transferase | OXCT catalyzes the reversible transfer of coenzyme A from succinyl-CoA to acetoacetate as the first step of ketolysis (ketone body utilization) in extrahepatic tissues. |
| PCTK1 | PCTAIRE protein kinase 1 | | Belongs to the SER/THR family of protein kinases; CDC2/CDKX subfamily. May play a role in signal transduction cascades in terminally differentiated cells. |
| SERPINB5 | Serine proteinase inhibitor, clade B, member 5 | Proteinase/ Proteinase Inhibitor/ Tumor Suppressor | Protease Inhibitor; Tumor suppressor, especially for metastasis. Inhibits tumor invasion by inhibiting cell motility. |
| SRP19 | Signal recognition particle 19 kD | | Responsible for signal-recognition-particle assembly. SRP mediates the targeting of proteins to the endoplasmic reticulum. |
| STAT1 | Signal transducer and activator of transcription 1, 91 kD | DNA-Binding Protein | Binds to the IFN-Stimulated Response Element (ISRE) and to the GAS element; specifically required for interferon signaling. STAT1 can be activated by IFN-alpha, IFN-gamma, EGF, PDGF and IL6. BRCA1-regulated genes overexpressed in breast tumorigenesis included STAT1 and JAK1. |
| TGFB3 | Transforming growth factor, beta 3 | Cell Signalling | Transmits signals through transmembrane serine/threonine kinases. Increased expression of TGFB3 may contribute to the growth of tumors. |
| TLX3 | T-cell leukemia, homeobox 3 | Transcription Factor | Member of the homeodomain family of DNA binding proteins. May be activated in T-ALL leukomogenesis. |
| VWF | Von Willebrand factor | Coagulation Factor | Multimeric plasma glycoprotein active in the blood coagulation system as an antihemophilic factor (VIIIC) carrier and platelet-vessel wall mediator. Secreted by endothelial cells. |

TABLE 12

Infectious Disease Gene Expression Panel

| Symbol | Name | Classification | Description |
| --- | --- | --- | --- |
| C1QA | Complement component 1, q subcomponent, alpha polypeptide | Proteinase/ Proteinase Inhibitor | Serum complement system; forms C1 complex with the proenzymes c1r and c1s |
| CASP1 | Caspase 1 | proteinase | Activates IL1B; stimulates apoptosis |
| CD14 | CD14 antigen | Cell Marker | LPS receptor used as marker for monocytes |
| CSF2 | Granulocyte-monocyte colony stimulating factor | cytokines-chemokines-growth factors | AKA GM-CSF; Hematopoietic growth factor; stimulates growth and differentiation of hematopoietic precursor cells from various lineages, including granulocytes, macrophages, eosinophils, and erythrocytes |
| EGR1 | Early growth response-1 | cell signaling and activation | master inflammatory switch for ischemia-related responses including chemokine sysntheis, adhesion moelcules and macrophage differentiation |
| F3 | F3 | Enzyme/ Redox | AKA thromboplastin, Coagulation Factor 3; cell surface glycoprotein responsible for coagulation catalysis |
| GRO2 | GRO2 oncogene | cytokines-chemokines-growth factors | AKA MIP2, SCYB2; Macrophage inflammatory protein produced by moncytes and neutrophils |
| HMOX1 | Heme oxygenase (decycling) 1 | Enzyme/ Redox | Endotoxin inducible |
| HSPA1A | Heat shock protein 70 | Cell Signaling and activation | heat shock protein 70 kDa |
| ICAM1 | Intercellular adhesion molecule 1 | Cell Adhesion/ Matrix Protein | Endothelial cell surface molecule; regulates cell adhesion and trafficking, upregulated during cytokine stimulation |
| IFI16 | gamma interferon inducible protein 16 | cell signaling and activation | Transcriptional repressor |
| IFNG | Interferon gamma | cytokines-chemokines-growth factors | Pro- and antiinflammatory activity, TH1 cytokine, nonspecific inflammatory mediator, produced by activated T-cells |
| IL10 | Interleukin 10 | cytokines-chemokines-growth factors | Antiinflammatory; TH2; suppresses production of proinflammatory cytokines |
| IL12B | Interleukin 12 p40 | cytokines-chemokines-growth factors | Proinflammatory; mediator of innate immunity, TH1 cytokine, requires co-stimulation with IL-18 to induce IFN-g |
| IL13 | Interleukin 13 | cytokines-chemokines-growth factors | Inhibits inflammatory cytokine production |
| IL18 | Interleukin 18 | cytokines-chemokines-growth factors | Proinflammatory, TH1, innate and aquired immunity, promotes apoptosis, requires co-stimulation with IL-1 or IL-2 to induce TH1 cytokines in T- and NK-cells |
| IL18BP | IL-18 Binding Protein | cytokines-chemokines-growth factors | Implicated in inhibition of early TH1 cytokine responses |
| IL1A | Interleukin 1, alpha | cytokines-chemokines-growth factors | Proinflammatory; constitutively and inducibly expressed in variety of cells. Generally cytosolic and released only during severe inflammatory disease |
| IL1B | Interleukin 1, beta | cytokines-chemokines-growth factors | Proinflammatory; constitutively and inducibly expressed by many cell types, secreted |
| IL1R1 | interleukin 1 receptor, type I | receptor | AKA: CD12 or IL1R1RA |
| IL1RN | Interleukin 1 receptor antagonist | cytokines-chemokines-growth factors | IL1 receptor antagonist; Antiinflammatory; inhibits binding of IL-1 to IL-1 receptor by binding to receptor without stimulating IL-1-like activity |
| IL2 | Interleukin 2 | cytokines-chemokines-growth factors | T-cell growth factor, expressed by activated T-cells, regulates lymphocyte activation and differentiation; inhibits apoptosis, TH1 cytokine |

TABLE 12-continued

Infectious Disease Gene Expression Panel

| Symbol | Name | Classification | Description |
|---|---|---|---|
| IL4 | Interleukin 4 | cytokines-chemokines-growth factors | Antiinflammatory; TH2; suppresses proinflammatory cytokines, increases expression of IL-1RN, regulates lymphocyte activation |
| IL6 | Interleukin 6 (interferon, beta 2) | cytokines-chemokines-growth factors | Pro- and antiinflammatory activity, TH2 cytokine, regulates hemotopoietic system and activation of innate response |
| IL8 | Interleukin 8 | cytokines-chemokines-growth factors | Proinflammatory, major secondary inflammatory mediator, cell adhesion, signal transduction, cell-cell signaling, angiogenesis, synthesized by a wide variety of cell types |
| MMP3 | Matrix metalloproteinase 3 | Proteinase/Proteinase Inhibitor | AKA stromelysin; degrades fibronectin, laminin and gelatin |
| MMP9 | Matrix metalloproteinase 9 | Proteinase/Proteinase Inhibitor | AKA gelatinase B; degrades extracellular matrix molecules, secreted by IL-8-stimulated neutrophils |
| PLA2G7 | Phospholipase A2, group VII (platelet activating factor acetylhydrolase, plasma) | Enzyme/Redox | Platelet activating factor |
| PLAU | Plasminogen activator, urokinase | Proteinase/Proteinase Inhibitor | AKA uPA; cleaves plasminogen to plasmin (a protease responsible for nonspecific extracellular matrix degradation) |
| SERPINE1 | Serine (or cysteine) protease inhibitor, clade B (ovalbumin), member 1 | Proteinase/Proteinase Inhibitor | Plasminogen activator inhibitor-1/PAI-1 |
| SOD2 | superoxide dismutase 2, mitochondrial | Oxidoreductase | Enzyme that scavenges and destroys free radicals within mitochondria |
| TACI | Tumor necrosis factor receptor superfamily, member 13b | cytokines-chemokines-growth factors | T cell activating factor and calcium cyclophilin modulator |
| TIMP1 | tissue inhibitor of metalloproteinase 1 | Proteinase/Proteinase Inhibitor | Irreversibly binds and inhibits metalloproteinases, such as collagenase |
| TLR2 | toll-like receptor 2 | cell signaling and activation | mediator of petidoglycan and lipotechoic acid induced signalling |
| TLR4 | toll-like receptor 4 | cell signaling and activation | mediator of LPS induced signalling |
| TNF | Tumor necrosis factor, alpha | cytokines-chemokines-growth factors | Proinflammatory, TH1, mediates host response to bacterial stimulus, regulates cell growth & differentiation |
| TNFSF13B | Tumor necrosis factor (ligand) superfamily, member 13b | cytokines-chemokines-growth factors | B cell activating factor, TNF family |
| TNFSF5 | Tumor necrosis factor (ligand) superfamily, member 5 | cytokines-chemokines-growth factors | ligand for CD40; expressed on the surface of T cells. It regulates B cell function by engaging CD40 on the B cell surface |
| TNFSF6 | Tumor necrosis factor (ligand) superfamily, member 6 | cytokines-chemokines-growth factors | AKA FasL; Ligand for FAS antigen; transduces apoptotic signals into cells |
| VEGF | vascular endothelial growth factor | cytokines-chemokines-growth factors | Producted by monocytes |
| IL5 | Interleukin 5 | Cytokines-chemokines-growth factors | Eosinophil stimulatory factor; stimulates late B cell differentiation to secretion of Ig |
| IFNA2 | Interferon alpha 2 | Cytokines-chemokines- | interferon produced by macrophages with antiviral effects |

What is claimed is:

1. A method, for evaluating a biological condition of a subject, based on a sample from the subject, the sample providing a source of RNAs, the method comprising:

using amplification for measuring the amount of RNA of at least two constituents from any one of Tables 1 through 12 from the sample of the subject, where a panel of constituents is selected so that measurement of the constituents enables evaluation of the biological condition and wherein the measures of all constituents in the panel form a first profile data set, using amplification for measuring the amount of RNA of all constituents in said panel wherein the measures of all constituents in the panel are from a relevant population of subjects and form a normative baseline profile data set; and producing a calibrated profile data set for said panel, wherein each member of the calibrated profile data set is a function of a member of the first profile data set and the corresponding member of the normative baseline profile data set, wherein the measures for each constituent are performed under measurement conditions that are substantially repeatable and the efficiencies of amplification for all constituents are substantially similar and the calibrated profile data set provides a measure of the biological condition of the subject.

2. A method according to claim 1, wherein efficiencies of amplification, expressed as a percent, for all constituents lie within a range of approximately 2 percent.

3. A method according to claim 1, wherein measurement conditions are repeatable so that such measure for each constituent has a coefficient of variation, on repeated derivation of such measure from the sample, that is less than approximately 3 percent.

4. A method according to claim 1, wherein efficiencies of amplification, expressed as a percent, for all constituents lie within a range of approximately 1 percent.

5. A method according to claim 2, wherein measurement conditions are repeatable so that such measure for each constituent has a coefficient of variation, on repeated derivation of such measure from the sample, that is less than approximately 3 percent.

6. A method according to claim 1, wherein measurement conditions are repeatable so that such measure for each constituent has a coefficient of variation, on repeated derivation of such measure from the sample, that is less than approximately 3 percent.

7. A method according to claim 1, wherein the panel includes at least three constituents.

8. A method according to claim 1, wherein the panel has fewer than approximately 500 constituents.

9. A method according claim 1, wherein the biological condition is inflammation and the panel of constituents includes at least two of the constituents of the Inflammation Gene Expression Panel of Table 1.

10. A method according to claim 1, wherein the biological condition is diabetes and the panel of constituents includes at least two of the constituents of the Diabetes Gene Expression Panel of Table 2.

11. A method according to claim 1, wherein the biological condition is prostate health or disease and the panel of constituents includes at least two of the constituents of the Prostate Gene Expression Panel of Table 3.

12. A method according to claim 1, wherein the biological condition is manifested in skin and the panel of constituents includes at least two of the constituents of the Skin Response Gene Expression Panel of Table 4.

13. A method according to claim 1, wherein the biological condition is liver metabolism and disease and the panel of constituents includes at least two of the constituents of the Liver Metabolism and Disease Gene Expression Panel of Table 5.

14. A method according to claim 1, wherein the biological condition is vascular and the panel of constituents includes at least two of the constituents of the Endothelial Gene Expression Panel of Table 6.

15. A method according to claim 1, wherein the biological condition is abnormal cell development and the panel of constituents includes at least two of the Cell Health and Apoptosis Gene Expression Panel of Table 7.

16. A method according to claim 1, wherein the biological condition is inflammation and the panel of constituents includes at least two of the constituents of the Cytokine Gene Expression Panel of Table 8.

17. A method according to claim 1, wherein the biological condition is inflammation and the panel of constituents includes at least two of the constituents of the TNF/IL1 Inhibition Gene Expression Panel of Table 9.

18. A method according to claim 1, wherein the biological condition is inflammation and the panel of constituents includes at least two, of the constituents of the Chemokine Gene Expression Panel of Table 10.

19. A method according to claim 1, wherein the biological condition is cancer and the panel of constituents includes at least two of the constituents of the Breast Cancer Gene Expression Panel of Table 11.

20. A method according to claim 1, wherein the biological condition is infectious disease and the panel of constituents includes at least two of the constituents of the Infectious Disease Gene Expression Panel of Table 12.

21. A method according to claim 1, wherein the relevant population is a population of healthy subjects.

22. A method according to claim 1, wherein the relevant population has in common a property that is at least one of age group, gender, ethnicity, geographic location, diet, medical disorder, clinical indicator, medication, physical activity, body mass, and environmental exposure.

23. A method, for evaluating a biological condition characterized by inflammation of a subject, based on a sample from the subject, the sample providing a source of RNAs, the method comprising:

using amplification for measuring the amount of RNA of constituents from the sample of the subject, where a panel of constituents is selected so that measurement of the constituents enables evaluation of the biological condition and wherein the measures of all constituents in the panel form a first profile data set, using amplification for measuring the amount of RNA of all constituents in said panel wherein the measures of all constituents in the panel are from a relevant population of subjects and form a normative baseline profile data set; and producing a calibrated profile data set for said panel, wherein each member of the calibrated profile data set is a function of a member of the first profile data set and the corresponding member of the normative baseline profile data set, wherein the measures for each constituent are performed under measurement conditions that are substantially repeatable and the efficiencies of amplification for all constituents are substantially similar and the calibrated profile data set provides a measure of the biological condition of the subject.

24. A method according to claim 23, the panel including at least three of the constituents of the Inflammation Gene Expression Panel of Table 1.

25. A method according to claim 23, the panel including at least four of the constituents of the Inflammation Gene Expression Panel of Table 1.

26. A method according to claim 23, the panel including at least five of the constituents of the Inflammation Gene Expression Panel of Table 1.

27. A method according to claim 23, the panel including at least six of the constituents of the Inflammation Gene Expression Panel of Table 1.

* * * * *